US005770363A

United States Patent [19]
Brown

[11] Patent Number: 5,770,363
[45] Date of Patent: *Jun. 23, 1998

[54] METHODS FOR DIAGNOSING HUMAN MALE INFERTILITY

[76] Inventor: David B. Brown, 1216 Pin Oak Dr., Dickinson, Tex. 77539

[*] Notice: The term of this patent shall not extend beyond the expiration date of Pat. No. 5,358,847.

[21] Appl. No.: 472,668

[22] Filed: Jun. 7, 1995

Related U.S. Application Data

[63] Continuation-in-part of Ser. No. 781,357, Oct. 24, 1991, Pat. No. 5,358,847, and Ser. No. 269,340, Jun. 30, 1994, abandoned.

[51] Int. Cl.$^6$ .............................. C12Q 1/68; C12Q 1/00; A01N 1/02; C12N 5/00
[52] U.S. Cl. ...................... 435/6; 435/2; 435/4; 435/325
[58] Field of Search ............................... 435/6, 806, 810, 435/240.2, 1, 2, 325

[56] References Cited

U.S. PATENT DOCUMENTS

| 4,683,212 | 7/1987 | Ax | 436/501 |
|---|---|---|---|
| 5,135,759 | 8/1992 | Johnson | 424/561 |
| 5,358,847 | 10/1994 | Brown | 435/6 |

FOREIGN PATENT DOCUMENTS

| 358291 | 3/1990 | European Pat. Off. . |
|---|---|---|
| 90-077026/11 | of 1988 | WIPO . |
| 90-206641/27 | of 1990 | WIPO . |
| 87-228385/32 | of 1995 | WIPO . |

OTHER PUBLICATIONS

Hutchison et al. EMBO J. (1987) 6(7):2003–2010.
Vanderlaan et al. Cytometry 7:449–507 (1986).
Brown, et al, "Some cases of human male infertility are explained by abnormal in vitro human sperm activation", Fertility and Sterility, 64(3):612–622, 1995.
Sawyer and Brown, "The Use of an In Vitro Sperm Activation Assay to Detect Chemically Induced Damage of Human Sperm Nuclei", Reproductive Toxicology, 9(4):351–357, 1995.
Brown et al., J. Exp. Zool., 258:263–272 (1991).
Ohsumi et al., Gamete Res. (USA), 20(1):1–9 (1988).
Brown, D., Press Release and Poster Presentation, Dec. 10, 1990 – 30th Annual Meeting of the American Society for Cell Biology in San Diego, CA.
Brown et al., J. Exp. Zool., 242(2):215–231 (1987).
Gordon et al., Exp. Cell. Res., 157(2):409–418 (1985).
Brown et al., J. Cell Biol., 111:115a (1990).
Longo, Biology of Fertilization, 3:250–298 (1985).
Vodyanoy et al., Science, 220:719–721 (1983).
Longo et al., Current Top. in Dev. Biol., 12(6):149–187 (1978).
Zirkin et al., Gamete Research, 11:349–365 (1985).
Perreault et al., Development Biology, 101:160–167 (1984).
Kasinsky et al., the Journal of Experimental Zoology, 234:33–46 (1985,.

Yanagimachi et al., Biology of Reproduction, 15:471–476 (1976).
Overstreet et al., Fertility and Sterility, 33(5):534–542 (1980).
Wolf et al., Journal of Andrology, 3:445–451 (1982).
Laskey et al., Science, 246:609–614 (1989).
Lohka, Journal of Cell Science, 952:131–135 (1989).
Fang et al., Cell, 66:731–742 (1991).
Kasinsky, "In: Histones and Other Basic Nuclear Proteins, Specificity and Distribution of Serum Basic Proteins," pp. 73–150, CRC Press, Boca Raton, Fla., eds. L. Hnilica, G. Stein and J. Stein (1989).
Webster et al., "In: The Handbook of the Laboratory Diagnosis and Treatment of Infertility, The Infertility Evaluation," pp. 1–9, CRC Press, eds. B. Keel and B. Webster (1990).
Wolgemuth, Mechanism and Control of Animal Fertilization, (9):415–452 (1983).
Ohsumi et al., Gamete Research, 20:P1–9 (1988).
Lohka et al., Experimental Cell Research, 179:303–309 (1988).
Bleil, et al., "Autoradiograph Visualization of a Localized Binding of Mouse Egg's Sperm Receptor to Sperm," J. Cell Biol., 101:263a (1985).
Brown and Nagamani, "Use of Xenopus laevis Frog Egg Extract in Diagnosing Human Male Unexplained Infertility," Yale J. Biol. Med., 65:29–38 (1992).
Brown, et al., "In vitro Activation of Human Sperm Nuclei Using Xenopus Laevis Egg Extract," J. Cell Biol., 99:396a (1984).

(List continued on next page.)

Primary Examiner—Lisa B. Arthur
Attorney, Agent, or Firm—Denise L. Mayfield, Esq.

[57] ABSTRACT

A method for determining the capacity of a human sperm to fertilize a human egg is described by assessing sperm activation events in an in vitro assay using a non-mammalian egg extract, particularly a Xenopus laevis frog egg extract. Fertilizing capacity is assessed as a comparison of sperm decondensation, DNA synthesis and/or sperm recondensation as between a test sperm sample sperm and fertile sperm, such as a sperm sample from a proven fertile human male. The method employs results from the in vitro assay to also determine relative sufficiency or insufficiency of a sperm sample for fertilizing a human egg in human couples with a history of a diagnosed unexplained infertility from standard infertility diagnostic tests. The method may also be used to screen human sperm donors in human artificial insemination programs. A fixed-slide cytoprep sperm analysis of decondensed sperm chromatin, as between a sperm test sample and a sperm sample from a proven fertile human male, may also be used to confirm in vitro decondensation results of the infertility or fertility of a particular human male. A kit is also provided for testing male sperm samples for human egg fertilizing capacity. A process for snap-freezing egg extract without loss of human sperm activation. Event supporting activity is also provided.

32 Claims, 15 Drawing Sheets

OTHER PUBLICATIONS

Collins and Crosginani, "Unexplained infertility: a review of diagnosis, prognosis, treatment efficacy and management," *Int. J. Gynecol. Obstet.*, 39:267–275 (1992).

Kruger, et al., "A new computer method of reading sperm morphology (strict criteria) is as efficient as technician reading," *Fertil. Steril.*, 59(1)202–209 (Jan. 1993).

Liu, et al., "The use of in vitro fertilization to evaluate putative tests of human sperm function," *Fertil. Steril.*, 48(2):272–277 (Feb. 1988).

Liu and Baker, "Tests of human sperm function and fertilization in vitro," *Fertil. Steril.* 58(3):465–483 (Sep. 1992).

Gordon, J., "Current Unresolved Controversies in Micromanipulation–Assisted Fertilization," *J. Asst. Reprod. Genet.*, 9(3):184–186 (1992).

Marmar, et al., "Insemination data on men with varicoceles," *Fertil. Steril.*, 57(5):1084–1090 (May 1992).

Ng, et al., "Controversies in Micro–Injection," *J. Asst. Reprod. Genet.*, 9(3):186–189 (1992).

Slott and Perreault, "Computer–Assisted Sperm Analysis of Rodent Epididymal Sperm Motility Using the Hamilton–Thorn Motility Analyzer," *Meth. Toxicol.*, 3A:319–333 (1993).

Takihara, et al., "The pathophysiology of varicocele in male infertility," *Fertil. Steril.*, 55(5):861–868 (May 1991).

Tennekoon and Karunanayake, "Serum FSH, LH, and Testosterone Concentrations in Presumably Fertile Men: Effect of Age," *Int. J. Fertil.*, 38(2):108–112 (1993).

Gordon et al., "Activation of human sperm nuclei using cell–free extracts from *Xenopus leavis* eggs," (Society for Development Biology, Abstract #63) (1984).

Atiee, et al., "A simple approach to intracytoplasmic sperm injection," *Fertil. Steril.*, 63(3):652–655 (1995).

Gordon, et al., "Activation of human sperm nuclei using cell–free extracts from *Xenopus laevis* eggs," *Society for Development Biology* (Jun. 18–20, 1984).

Griveau, et al., "Decondensation of Human Sperm Nuclei and HP1 Protamine Degradation From Normospermia and Asthenospermia in Xenopus Egg Extracts," *Archives of Andrology* 29:127–136 (1992).

Iwao, et al., "In Vitro Induction of Sperm Nucleus Decondensation by Cytosol From Mature Toad Eggs," *Jou. Exp. Zool.*, 230:115–124 (1984).

Kunkle, et al., "Analysis of Isolated Sea Urchin Nuclei Incubated in Egg Cytosol," *J. Exp. Zool.*, 203:381–390 (1978).

Lohka, et al., "Formation in vitro of Sperm Pronuclei and Mitotic Chromosomes Induced by Amphibian Ooplasmic Components," *Science*, vol. 220, pp. 719–721, (1983).

Lohka, et al., "Induction of Metaphase Chromosome Condensation in Human Sperm by Xenopus Egg Extracts," *Experimental Cell Research* 179 303–309 (1988).

Lohka, "Mitotic control by metaphase–promoting factor and cdc proteins," *Journal of Cell Science* 92, 131–135 (1989).

Murray and Kirschner, "Cyclin synthesis drives the early embryonic cell cycle," *Nature*, vol. 339, pp. 275–280 (25 May 1989).

Murray and Kirschner, "What Controls the Cell Cycle," *Scientific American*, pp. 56–63 (Mar. 1991,.

Newport, "Nuclear Reconstitution in Vitro: Stages of Assembly around Protein–Free DNA," *Cell*, vol. 48, 205–217 (Jan. 30, 1987).

Palermo, et al., "Intracytoplasmic sperm injection: a novel treatment for all forms of male factor infertility," *Fertil. Steril.*, vol. 63, No. 6, pp. 1231–1240 (Jun. 1995).

Palermo, et al., "Pregnancies after intracytoplasmic injection of single spermatozoon into an oocyte," *The Lancet*, vol. 340, pp. 17–18, (Jul. 4, 1992).

Pines and Hunter, "Human Cyclins A and B1 Are Differentially Located in the Cell and Undergo Cell Cycle–Dependent Nuclear Transport," *Jou. Cell Biol.*, vol. 115, No. 1, pp. 1–17, (Oct. 1991).

Reed, et al., $G_1$ Control in Yeast and Animal Cells, Cold Spring Harbor Symposia on Quantitative Biology, vol. 56, *Cold Spring Harbor Laboratory Press*, 0–87969, pp. 61–67 (May 1991).

(Sawyer, et al.) "Use of a Male Fertility Assay as a Toxicological Screen," 33rd Annual Meeting, Society of Toxicology, Dallas, TX, *Toxicologist* 14:208A, Mar. 13–17, 1994.

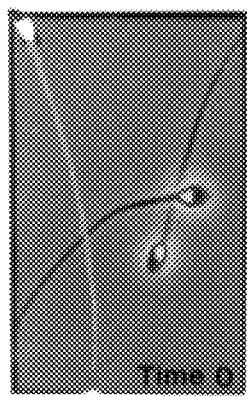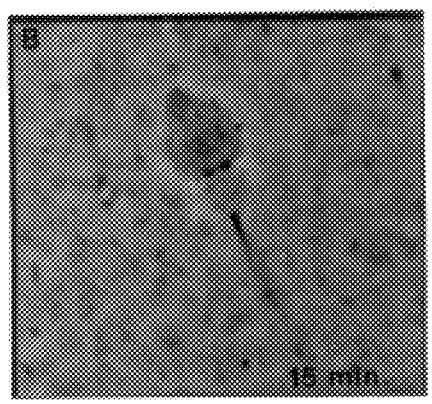
Fig. 1A        Fig. 1B
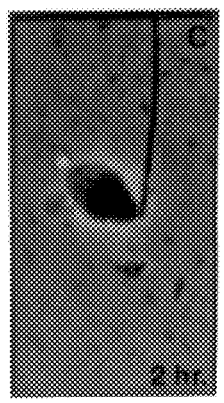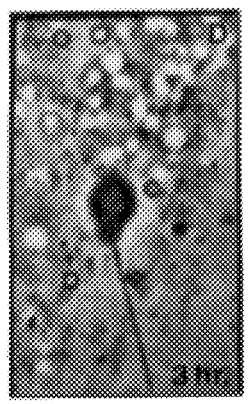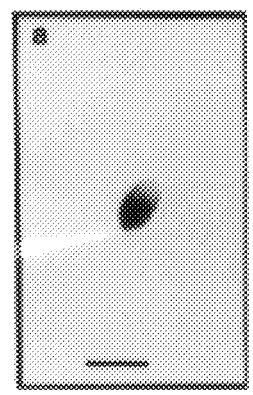
Fig. 1C        Fig. 1D        Fig. 1E
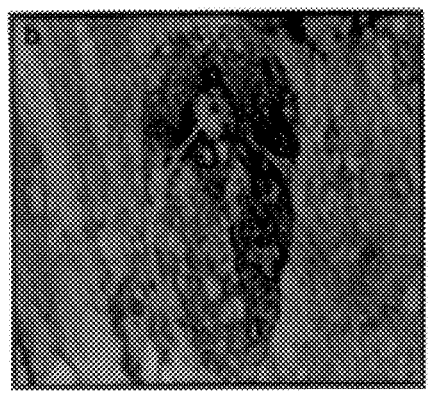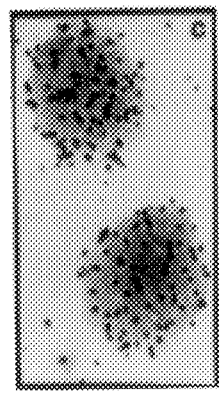
Fig. 1F        Fig. 1G        Fig. 1H

DECONDENSATION (% OF CONTROL)

DNA SYNTHESIS (% OF CONTROL)

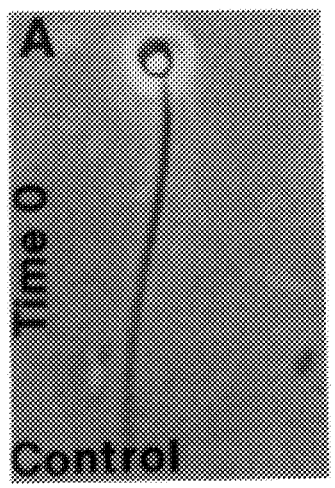
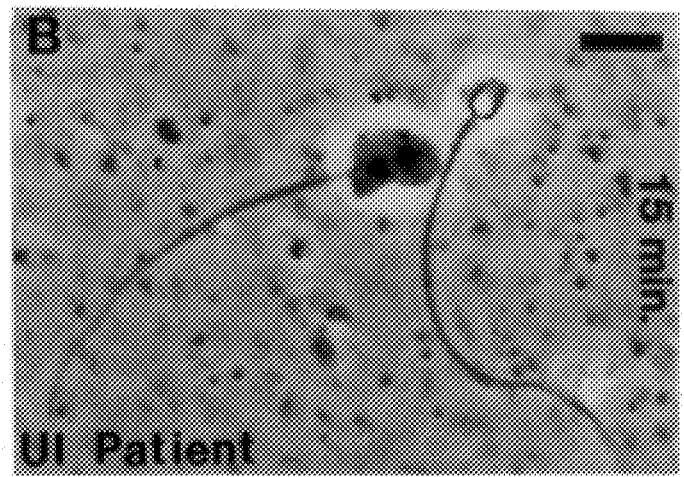
Fig. 10A    Fig. 10B
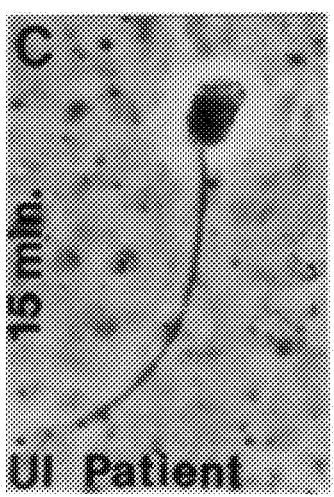
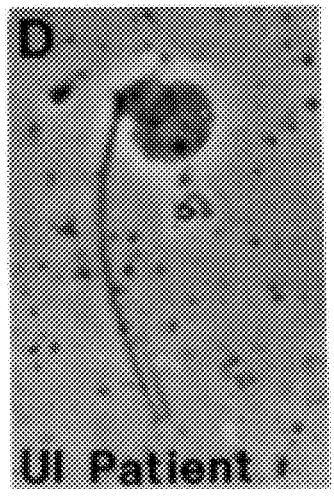
Fig. 10C    Fig. 10D    Fig. 10E

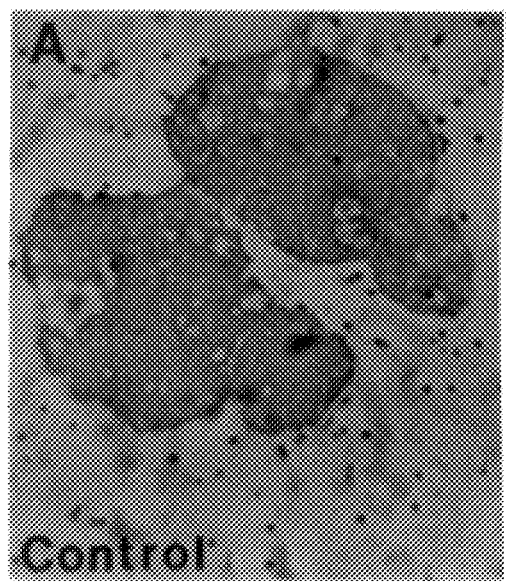
Fig. 11A
Fig. 11B
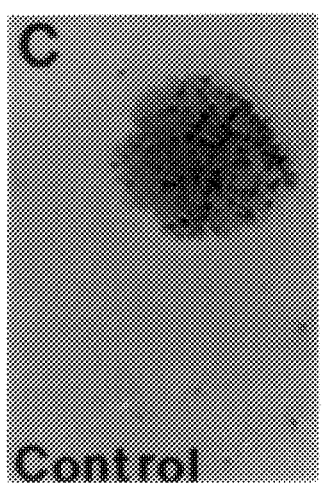
Fig. 11C
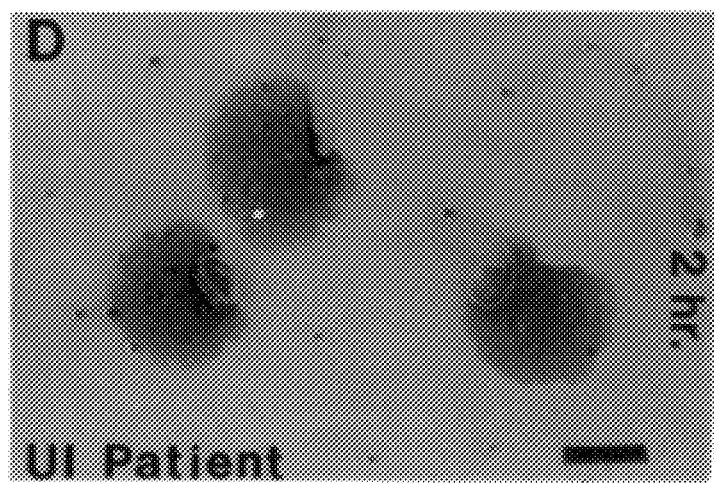
Fig. 11D

METHODS FOR DIAGNOSING HUMAN MALE INFERTILITY

This application is a continuation-in-part application of U.S. Ser. No. 07/781,357 filed on Oct. 24, 1991, now U.S. Pat. No. 5,358,847, and U.S. Ser. No. 08/269,340, filed Jun. 30, 1994 now abandoned.

BACKGROUND OF THE INVENTION

1. Field of the Invention

The present invention relates to the field of diagnostic tests for determining if a human male is infertile. More specifically, the present invention provides a method for identifying infertile males by assessing the ability of a particular human sperm sample to fertilize a human egg. The invention also relates to the field of screening protocols, as a method for screening human sperm samples for use in human fertilization is also provided. The invention also relates to the field of diagnostic kits, as a kit for detecting male infertility is also disclosed.

2. Description of the Related Art

Approximately one in six couples find themselves involuntarily infertile. This translates to between two and four million couples in the United States alone. Although numerous tests are available for diagnosing infertility problems, 16% of all couples that seek medical treatment are diagnosed with what is described clinically as "unexplained infertility".[2]

The term "unexplained infertility" is applied to virtually any clinically inexplicable failure of a male and female couple to conceive after extensive fertility testing of both partners reveals no identifiable cause for the couples infertility. When a couple is found to be "normal" in their standard fertility evaluation (i.e., female post-coital tests, timed endometrial biopsy, hysterosalpingogram, laparoscopy, male, "normal" sperm analysis, with sperm counts greater than 20 million/ml on at least two occasions, total sperm numbers of 40 million or more, sperm motility greater than 60%, and normal morphology in more than 60% of the sperm[4]), and the couple has had a history of involuntary infertility for at least 2 years, a human couple is diagnosed unsatisfactorily as "unexplainably infertile." Such couples historically undergo numerous invasive, protracted and expensive assisted reproductive technology attempts in their pursuit of pregnancy.

Although numerous tests are available for diagnosing infertility problems, 16% of all couples who seek medical treatment are diagnosed with unexplained infertility. Male members of inexplicably infertile couples produce sperm that appear normal in standard semen analyses that include assessment of sperm density, progressive motility, sperm morphology and semen volume. Since these methods have limited capacity for evaluating male fertility, other tests have been developed including: quantitative ultramorphology (QUM) using transmission and scanning electron microscopy[109]; in vitro nuclear chromatin decondensation (NCD) analysis[110]; and the sperm chromatin structure assay (SCSA; [111]). Tests of human sperm function have also been developed, including: videomicrographic assessment of motility (straight line and curvilinear velocity, and amplitude of lateral head displacement); analysis of membrane integrity; tests for sperm nuclear maturity; measurements of acrosomal status; acrosome reaction and acrosin activity; and the analysis of sperm penetration of hamster zona-free ova (sperm penetration assay; SPA); and zona binding. However, except for the SPA, none of these tests directly assay sperm activation events that occur after the sperm nucleus enters into the egg, a series of events critical for the entry of the zygote into the developmental program.

Tests of human sperm function have been developed in recognition that standard semen analysis provides a limited evaluation of the male's fertility potential. In fact, males having unexplained infertility are found to be normal in standard semen analysis. One such fertility test for human males is the sperm penetration assay (SPA).[39-4,71,72,83] The SPA tests the activation of a human sperm nucleus following entry into a fertilized egg by determining the percentage of eggs penetrated by the sperm (as determined by counting the eggs that contain decondensed or activated sperm nuclei). In general, this assay is designed to test the sperm's ability to get its nucleus into the egg. However, this protocol is not used nor may it be used to indicate the efficiency of the sperm decondensation process. During the SPA, the egg (for example, the commonly used hamster egg) routinely becomes bound with a large number of sperm that do not enter the egg and thus do not decondense. Thus, using this assay, one cannot tell a non-decondensed sperm (because it has become bound to the egg) apart from a sperm that has entered the egg and not decondensed as a result of not responding to the egg "activation" signals.

In some cases, the present inventor have observed a zero SPA score may not be reflecting the penetration capabilities of a particular sperm, but instead may reflect the sperm's inability to decondense.

Various techniques have been devised by researchers for using permeabilized sperm incubated in frog egg extracts to study sperm activation events. For example, using *Xenopus laevis* frog sperm incubated in Rana pipiens frog egg extract[1] and using human sperm incubated in *Xenopus laevis* frog egg extract.[15-19] It has been observed that a normal (i.e., of proven human egg fertilizing capacity) human sperm nucleus becomes "activated" upon entry into a frog egg cytoplasm experimentally.[15-19]

The "activation" of a normal human sperm has been reported in preparations of *Xenopus laevis* frog egg extract, which is reportedly attributable to the presence of "factors" in the frog egg extract itself.[15-19] These activation "factors" in *Xenopus laevis* frog egg extract have been the focus of much investigation by the present inventor and others, and have facilitated the general characterization of "activation" events of normal human sperm (such as the events of the sperm nuclear chromatin decondensation-recondensation cycle and DNA synthesis),[5-19] as well as some insight into the molecular mechanisms of the activation events.

While the experimental model of *Xenopus Laevis* egg extract has been described which relates in general to the events of "normal" human sperm chromatin decondensation after activation,[15-19] the efficiency of the decondensation process has not been described as pertinent to the sperm's fertilizing capacity. Nor is a diagnostic tool for determining or elucidating a particular cause of "unexplained" human male infertility using relative sperm "activation" events been characterized.

Additionally, analysis of the particular onset or duration of, for example, sperm decondensation or sperm recondensation, or the amount of, for example, DNA synthesis, indicators of human male infertility or human sperm capacity to fertilize a human egg, has not been described or suggested in any of the literature. The use of mammalian eggs as a means to obtain extract to follow the sperm activation events has not been possible because it is difficult, if not impossible, to obtain enough extract to examine mammalian fertilization.[44,45]

Biological models for assessing human male fertility have not been established which employ sperm decondensation, recondensation and DNA synthesis events as a diagnostic tool. Moreover, the failure of currently available experimental and clinically accepted tests to examine the relative rate and degree of activity during sperm "activation events", as between "normal" human sperm and sperm with unknown fertilizing capacity, prevents the discovery of the differences which the present inventor have found definitive of the cause of some couples inability to successfully conceive. Even more, this approach has also been shown to be highly predictive of successful assisted reproductive technology (ART) attempts at pregnancy. For example, while all sample that have responded normally in the assay have resulted in pregnancy, sperm samples that provide abnormal responses have not.

An alternative method for diagnosing some cases of "unexplained infertility" through a system which was relatively non-invasive, and which provided for a rapid and accurate prognostic indicator of a human sperm samples' fertilizing capacity for a human egg, would save many currently "unexplained infertile" couples continued expense and invasive, and sometimes uncomfortable, attempts at pregnancy using assisted reproductive technologies.

Varicocele has been recognized as one of the leading causes of male infertility, and is frequently associated with abnormal sperm characteristics that include low values of sperm density, motility, and/or abnormal morphology, some also having abnormal SPA results. Steeno et al. recognizes three degrees of varicocele (grades I–III) and an additional group of clinically suspect cases[51] Here, tortuous dilations of the testicular veins result in stagnation of veinous blood in the pampiniform plex. Several causes are suggested to explain the negative effects of varicocele on spermatogenesis; these include: (a) hyperthermia; (b) reflux of renal and adrenal veinous blood into the testes; (c) altered testicular steroidogenesis; (d) hypoxia; and (e) mechanical compression.[63] However, none of these hypotheses are accepted unequivocally, as the mechanism of the pathophysiology associated with varicocele is still not well understood. A noninvasive technique for screening varicocele patients for the cause of their infertility would also provide a technique for screening potential candidates for varicocelectomy as a corrective measure for enhancing the fertility of the patient, as well as a technique for measuring the success of such surgeries in patients having undergone an elected varicocelectomy.

Several studies have shown that human semen quality has been decreasing over the last 60 years[121] having been attributed to environmental, rather than genetic causes, due to the relatively short time period of occurrence and the rapid influx into our environment of man-made chemicals, many of which are known to affect male fertility adversely. However, these studies reported changes in traditional semen parameters that have a limited capacity for evaluating mechanisms of male infertility. In addition, it has recently been observed that human sperm nuclear stability is highly variable relative to other species[122]. Whether this variability has persisted throughout human evolution or has been only recently manifested is unknown. This, coupled with the fact that standard semen analyses (sperm count, morphology, etc.) correlate poorly with human fertility[97], demands that new assays be developed to assess sperm quality and functionality.

During mammalian spermatogenesis, histones are progressively replaced by a series of intermediate basic proteins, and ultimately by protamines[124]. As a result, the chromatin is highly condensed, with its DNA in a genetically quiescent state. During fertilization, the sperm nucleus is deposited into the ovum cytoplasm; the sperm chromatin is then remodeled by ovum-derived cytoplasmic factors into a genetically active state, capable of DNA replication. Among these factors are: nucleoplasmin, which directs the protamine-to-histone exchange (chromatin decondensation;[113]; cyclins and cyclin-dependent kinases, which direct the cell-cycle traverse[9,11,61,62]; and all components needed for the formation of pronuclei and DNA synthesis[48,49,54-60]. This process of sperm chromatin remodeling and pronucleus formation, collectively known as sperm activation, is essential for successful development of the zygote, and thus for fertility.

Male reproductive system toxicants exist that have been shown in animals to reduce fertility without affecting such semen parameters as sperm count and concentration, motility, and morphology. These compounds may be causing infertility by adversely affecting the sperm nucleus, and thus, sperm nuclear activation. For example, 1,3-dinitrobenzene given at low chronic doses to rats (1.5 mg/kg/day for 10 weeks) does not significantly inhibit spermatogenesis (normal sperm counts), yet fertility in rats is still diminished[125]. Vaginal smears taken from female rats mated to males treated with 1,3-dinitrobenzene were found to be sperm-positive, yet no implantation sites were found. As another example, cyclophosphamide affects fertility in rats by increasing pre- and postimplantation loss[126-129]. In addition, rats treated with cyclophosphamide for six weeks produce sperm that do not decondense[130].

Methods for evaluating the potential antifertility effects of toxic agents to which human males are routinely exposed are also needed in the overall management of fertility problems associated with human sperm malfunction. Such methods have not as yet been proposed in the medical arts.

SUMMARY OF THE INVENTION

The present inventor has defined a prognostic indicator for human male fertility which effectively assesses the ability of a particular human sperm sample to fertilize a human egg. Specifically, the inventor describes a method wherein a sperm sample's capacity for fertilizing a human egg is determined through the analysis and comparison of sperm molecular "activation" events (i.e., decondensation, DNA synthesis and recondensation) as between sperm samples obtained from a human male of unproven fertility/infertility and a human male of proven fertility. Special application of the present invention is disclosed by the inventor as a method whereby a percentage of even the most exhaustively and undefinitively diagnosed "infertile couples" may discover the cause of their infertility.

In one particular aspect, the present invention provides a method for determining the capacity of a human sperm sample to fertilize a human egg. The method requires a comparative analysis of particular sperm "activation" events as between a human patient sperm sample and sperm sample from a human male of proven fertility.

In one particular embodiment of the present invention, an in vitro method for accessing fertilizing capacity of human sperm for a human egg is provided. One particular embodiment of the method comprises obtaining a human sperm sample and isolating a number of sperm therefrom to provide a test sample having a sperm count, obtaining a human sperm sample from a male of proven fertility and isolating an equal number of sperm to provide a control sample having a sperm count, permeabilizing the sperm of the test sample and the control sample to provide a permeabilized sperm test sample and a permeabilized sperm control sample, chemically reducing the permeabilized sperm test sample and the permeabilized sperm control sample to provide a reduced sperm nuclei test sample and a reduced sperm nuclei control sample, incubating a volume of the reduced sperm nuclei test sample and an equal volume of the reduced sperm nuclei control sample in a *Xenopus laevis* frog egg extract, quantifying the sperm nuclei test sample and sperm nuclei control sample activation events for chromatin decondensation and DNA synthesis in the presence of a detectable labeling compound, and determining differences between the test sample and the control sample activation events to assess the fertilizing capacity of the test sperm sample. According to this particular embodiment, a test sample demonstrating decreased efficiency of chromatin decondensation (preferably 80% or less decondensed sperm nuclei) relative to the control sperm sample identifies abnormal human sperm. Such a sperm sample may be further defined as having a reduced capacity for fertilizing a human egg.

In a second embodiment of the method, the steps for assessing human sperm fertilizing capacity comprise obtaining a human sperm sample and isolating a number of sperm therefrom to provide a test sample, incubating the test sample in a non-mammalian egg extract capable of supporting sperm decondensation, DNA synthesis and sperm recondensation, monitoring the test sample for sperm decondensation; and comparing the sperm decondensation in the test sample to sperm decondensation of a human sperm sample from a proven fertile male in the non-mammalian egg extract, wherein a test sample demonstrating about 80% or less decondensed sperm relative to the control sample identifies abnormal human sperm. Optionally, the method may further include examination of relative DNA synthesis and chromatin recondensation of a test sperm sample as compared to sperm sample obtained from a proven fertile male. In some embodiments, a test sample demonstrating less than about 80% or about 85% or even about 90% decondensed sperm, relative to a control sperm sample, is used to identify abnormal human sperm in the patient being screened. In other applications of the method, sperm DNA synthesis is also to be monitored and compared to control sperm DNA over a defined incubation period (e.g., about 2 hours).

In a most particularly preferred embodiment, the onset of chromatin decondensation or chromatin recondensation are also parameters within which differences relative to a control sample are assessed. In this embodiment, the onset of chromatin decondensation after the onset of chromatin decondensation of the control sample, or an onset of chromatin recondensation after the onset of chromatin recondensation of the control sample defines a human sperm having a reduced capacity for fertilizing a human egg.

In another aspect of the present invention, a method for screening for abnormal human sperm as part of a regimen for diagnosing infertility in a human male of unexplained infertility is provided. This method comprises obtaining a sperm sample from a human male of unexplained infertility to provide a test sample having a sperm count, obtaining a sperm sample from a human male of proven fertility to provide a control sample having a sperm count, isolating a number of sperm from the test sample and an equal number of sperm from the control sample to provide an assay test sample and an assay control sample, permeabilizing an equal number of the sperm in the assay test sample and the assay control sample in a lysolecithin-containing medium to provide a permeabilized test sperm sample and a permeabilized control sperm sample, chemically reducing a number of the permeabilized test sperm and an equal number of control sperm sufficient to provide an amount of sperm chromatin sufficient to assess sperm chromatin decondensation in a *Xenopus laevis* extract isolation medium (XEIM) containing dithiothreitol to provide a reduced sperm nuclei test sample and a reduced sperm nuclei control sample in a volume of *Xenopus laevis* frog egg extract which includes a detectable labeling compound, quantifying the nuclei of the test reduced sperm nuclei sample and the control reduced sperm nuclei sample for chromatin decondensation, and comparing the test chromatin decondensation in the reduced sperm nuclei test sample to the chromatin decondensation in the sperm control sample, wherein a sperm test sample demonstrating 80% or less decondensed sperm nuclei as compared to the sperm control sample is characteristic of abnormal human sperm as part of a screening regimen of a human male having unexplained infertility.

According to this method, a test sample demonstrating 20%(++) or less decondensed sperm nuclei (i.e., less than about 80% of the control) relative to the control sample after about a 15 minute, or preferably a 5 or 10 minute, incubation period, is diagnostic of infertility in the human male of previously unexplained infertility. The specific incubation period, in first application of the method will depend primarily upon the incubation time period in which the control sample sperm demonstrate 90% or greater decondensation in the egg extract. This approach will control for variability in control decondensation related to differences in egg extract, and will thus even further normalize the results. It is in the experience of the inventor that 90% decondensation will occur relatively consistently within an about 5 to about 15 minute incubation period. A reduced amount of sperm decondensation in a test sperm sample is thus indicative of a human sperm inadequacy as the cause of infertility in the human male.

A method for diagnosing infertility in a human male of unexplained infertility may also be provided according to a method comprising isolating a number of sperm from the human male of unexplained infertility to provide a test sample, incubating the test sample in a non-mammalian egg extract capable of supporting human sperm decondensation, DNA synthesis and/or chromatin recondensation, and comparing the amount of chromatin decondensation of the test sample to the amount of chromatin decondensation of a control sample from a human male of known fertility, wherein a sperm test sample demonstrating 80% or less decondensed sperm nuclei as compared to the sperm control sample is diagnostic of infertility in the human male of unexplained infertility.

Most preferably, the non-mammalian egg extract is a frog egg extract, such as *Xenopus laevis* frog egg extract, *Rana pipiens* frog egg extract and *Bufo japonicum* frog egg extract. In such embodiments where the non-mammalian egg extract is a frog egg extract, the steps of incubating the test sample in the frog egg extract may be further defined as comprising the steps of permeabilizing a number of the sperm in the test sample in a lysolecithin-containing medium to provide a permeabilized test sperm, chemically reducing a number of the permeabilized test sperm in a XEIM containing dithiothreitol to provide reduced sperm nuclei, incubating an amount of the reduced sperm nuclei in a volume of *Xenopus laevis* frog egg extract which includes a detectable labeling compound (preferably for between about 5 to about 15 minutes), and comparing the decondensation of the test sperm as a percentage to a percentage of condensed nuclei from sperm of a human male of proven fertility incubated in the frog egg extract. In a preferred embodiment of the method, a test sample demonstrating 80% or less decondensed sperm nuclei as compared to the control sample is diagnostic of infertility in the human male patient.

In the practice of the described methods, the amount of test (and control) sperm chromatin sample incubated in the *Xenopus laevis* frog egg extract is most preferably about 200,000 sperm/100 μl of the *Xenopus laevis* egg extract. Use of this concentration has been found to significantly improve ease and speed by which 50 decondensed sperm nuclei may be scored without significant risk of titrating away essential sperm activation factors. Most preferably, the reduced sperm nuclei test sample and the reduced sperm nuclei control sample are to be first incubated with a detectable labeling compound, such as $^3$H-TTP. For example, the sperm are most preferably to be incubated at about 19° C. in 200 μl of the *Xenopus laevis* frog egg extract which contains, for example, $^3$H-TTP, with the labeled $^3$H-TTP being included at a concentration of about 80 μCi/ml of the *Xenopus laevis* frog egg extract. Most preferably, an incubation of the sperm nuclei test sample and sperm nuclei control sample with the $^3$H-TTP is conducted for about 2 hours at about 19° C. The term about 19° C. is defined for purpose of the present invention as between about 18° C. to about 24° C.

A 20% (i.e., 80% of control) or more decrease in test sperm DNA synthesis as compared to a control sample is indicative of a human sperm inadequacy as the cause of infertility in the human male.

In a most preferred aspect of the methods described above, the permeabilized test sperm and the permeabilized control sperm are reduced in XEIM containing about 50 mM dithiothreitol for about 45 minutes at a temperature of between about 0° C. to 4° C., otherwise described as "on ice."

A patient having "unexplained infertility" for purposes of the presently disclosed methods are male patients whose sperm sample demonstrated normal total sperm count, sperm volume, sperm concentration and sperm morphology, as outlined for "normality" by W. H. O.,[4] standards, for a proven fertile human male.

Specific control sperm characteristics defined from proven fertile males include a sperm concentration of at least 20 million/ml and a total sperm number of at least 40 million. Thus, for purposes of the present description of the invention, the test sperm sample will have been evaluated and determined to demonstrate a concentration of at least 20 million/ml and a total sperm number of at least 40 million.

Where control sperm is obtained immediately after ejaculation, the additional parameter of sperm motility may be examined, with a comparison therein being made to test sperm sample, again where the test sperm sample is obtained immediately after ejaculation. Where sperm motility is an available evaluating criteria, a sperm motility as described below would be characteristic of the human sperm test sample from a patient of unexplained infertility (i.e., within "normal" parameters). Criteria of semen sample "normality" as set forth in the World Health Organization (1987)[4] include the following.

| CRITERIA | |
|---|---|
| Volume | 2.0 ml or more |
| Ph | 7.2–7.8 |
| Sperm Concentration | 20 × 10$^6$ or more |
| Total Sperm Count | 40 × 10$^6$ spermatozoa or more |
| Motility | 60% or more with forward progression or 25% or more with rapid linear progression within 60 minutes after collection |
| Morphology | 60% or more with normal morphology (oval-shaped head with regular outline and acrosomal cap covering more than ⅓ of the head surface; midpiece about 7–8 μm standard; and tail uncoiled, at least 45 μm in length |
| White Blood Cells | Fewer than 1 × 10$^6$/ml |
| Zinc (total) | 2.4 micromolar or more/ejaculate |
| Citric Acid (total) | 52 μmol (10 mg) or more/ejaculate |
| Fructose (total) | 13 micromolar or more/ejaculate |
| MAR Test | Fewer than 10% spermatozoa with adherent particles |
| Immunobead Test | Fewer than 10% spermatozoa with adherent beads |

Most preferably, chromatin decondensation as part of the described method is monitored closely for about 5 to about 15 minutes, with close attention being drawn to the time of test sample chromatin decondensation onset, as well as the relative percentage of sperm nuclei showing chromatin decondensation observed in the test sample relative to that observed in the control sample.

The control samples are stored as semen from proven fertile males obtained fresh on the day of assay. Stored sperm samples may be refrigerated at about 4° C. without significant loss of activity. The present inventor has found that control semen samples and sperm isolated therefrom, refrigerated at 4° C. may be stored without significant loss of sperm activation capacity for up to 30 days and sperm isolated therefrom for use in the present method. Non-permeabilized sperm samples may also be stored frozen and then thawed sperm assayed in the presently described methods have no significant change of sperm activation capacity as measured with previously non-frozen samples. Semen and sperm samples from unproven males may similarly be stored at 4° C., or frozen, for future testing purposes. Semen and sperm samples may be stored frozen for up to 1 year without significant loss of sperm activation capacity. The inventor has found that DNA damage occurs with some frequency when permeabilized sperm are frozen, as evidenced in changed response for DNA synthesis in the HSAA.

In an even more preferred embodiment of the claimed method, prior to permeabilizing the test and control sperm samples, the test semen sample and control semen sample are to be washed in a nuclear isolation medium consisting of about 200 mM sucrose, about 2.4 mM MgCl$_2$, about 10 mM Tris HCl and about 5 mM maleic acid and a pH of about 7.4. All test and control semen samples must be washed at least once to obtain an at least partially isolated sperm sample.

Cytoprep analysis of the test sample has also been found to be confirmatory of the results obtained in the present methods. Cytoprep analysis may be prepared from an aliquot of the test and control "incubation" of sperm at any time point. Most preferably, the cytoprep analysis is to be prepared from an aliquot obtained at 15 minutes incubation (for "smear" of sperm nuclei analysis, a measure of decondensation relative to control).

A test sperm sample which demonstrates about 80% or less the total number of smeared sperm nuclei of the control (described in the examples), (prepared from sperm sample obtained after an about 15 minute incubation period), is diagnostic of a infertile human male. A cytoprep analysis of the number of smeared sperm nuclei after an about 15 minute incubation period may therefore be used either alone as an independent diagnostic test for human male infertility or as a confirmatory test to confirm assay results determined on the basis of the percentage of chromatin decondensation relative to a control sample after an about 15 minute incubation period. A volume of the original test and control sperm incubation sample is obtained and used to prepare the cytoprep analysis. A cytoprep analysis provides a permanent record of the decondensation events observed.

Permeabilization of the test sample and control sample sperm most preferably is accomplished by incubating an equal number of the sperm test sample and the sperm control sample in a medium containing about 0.05% lysolecithin and about 1 µg/ml soybean trypsin inhibitor for about 5 minutes at about 22° C.

In still another aspect of the present invention, a method for screening human sperm as part of a regimen for selecting prospective human sperm donors for in vitro fertilization of a human egg is provided. This screening method comprises obtaining a sperm sample from the prospective human sperm donor to provide a test sample, obtaining a sperm sample from a proven fertile human male to provide a control sample, permeabilizing a number of test sample sperm and an equal number of control sample sperm in a medium containing lysolecithin (preferably about 0.05%) and a serine protease inhibitor, such as about 1 µg/ml soybean trypsin inhibitor (a protease inhibitor which will inactivate proteases in the preparation) to provide permeabilized human test sperm and permeabilized human control sperm, chemically reducing a number of the permeabilized test sperm and an equal number of the permeabilized control sperm sufficient to assess sperm chromatin decondensation in a *Xenopus laevis* extract isolation medium containing dithiothreitol to provide a reduced test sperm sample and a reduced control sperm sample, incubating the chemically reduced test sperm sample and the reduced control sperm sample in a *Xenopus laevis* frog egg extract containing a detectable labelling compound, quantifying sperm decondensation and DNA synthesis of the test sample and the control sample (preferably for at least about 3 hours in a volume of *Xenopus laevis* frog egg extract), comparing the sperm decondensation, and DNA synthesis demonstrated in the reduced control sperm sample to the reduced test sperm sample, and selecting a prospective human sperm donor from a donor whose sperm test sample demonstrates an amount of sperm decondensation or DNA synthesis greater than 80% of the decondensation, recondensation or DNA synthesis of the control sperm sample.

In an alternative embodiment of the method for screening prospective human sperm donors, the present invention comprises obtaining a sperm sample from the prospective human sperm donor to provide a test sample, incubating the test sperm sample in a non-mammalian egg extract containing a detectable labeling compound, monitoring sperm decondensation of the test sample, comparing the sperm chromatin decondensation of the test sample to chromatin decondensation of the sperm sample from a human male of proven fertility, and selecting a sperm test sample that demonstrates an amount of sperm chromatin decondensation of at least 80% of controlled sperm chromatin decondensation as prospective donor sperm for in vitro fertilization of a human egg. Most preferably, the non-mammalian egg extract is used in the claimed method is a frog egg extract, such as *Xenopus laevis, Bufo japonicum* or *Rana pipiens* frog egg extract. Sperm chromatin decondensation is to be monitored for preferably 15 minutes.

In a most preferred aspect of the methods for selecting a prospective sperm donor, the test sperm and the control sperm sample are reduced in a volume of XEIM containing about 50 mM dithiothreitol for about 45 minutes at about 0° C. to 4° C. Most preferably, the detectable labelling compound used is $^3$H-TTP bromodeoxyuridine or tritiated thymidine.

The present invention also provides a method for screening for abnormal sperm as part of a regimen for diagnosing infertility in a human male partner of an unexplained infertile human couple. This method comprises preparing a modified *Xenopus laevis* frog egg extract capable of sequentially inducing at least three sperm activation events, said human sperm activation events including sperm chromatin decondensation and DNA synthesis, obtaining and preparing a sperm sample from the human male partner of the unexplained infertile human couple to provide a test sperm sample, obtaining and preparing a human sperm sample from a proven fertile human male to provide a control sperm sample, permeabilizing a number of the test sperm sample and an equal number of the control sperm sample in a nuclear isolation medium containing about 0.05% lysolecithin and about 1 µg/ml soybean trypsin inhibitor for about 5 minutes at about 22° C., washing the permeabilized test sperm sample and the control sperm sample in a volume of nuclear isolation medium containing about 3% bovine serum albumin, pelleting and washing a second time the permeabilized test human sperm sample and the control sperm sample in a volume of nuclear isolation medium containing about 0.4% bovine serum albumin, reducing a number of the washed test sperm sample and an equal number of the control sperm sample in a volume of XEIM. The XEIM most preferably contains about 10 mM Tris-HCl, about 1.5 mM $MgCl_2$, about 100 mM Kcl and about 50 mM dithiothreitol, wherein the concentration of control sperm and test sperm, respectively, in the medium is about 25,000 sperm/ml, for about 45 minutes at between about 0° C. to about 4° C.

Next, the method includes labeling the permeabilized (and reduced) test sperm sample and the control sperm sample in the presence of a detectable labeling compound contained within a volume of *Xenopus laevis* frog egg extract, wherein a concentration of about 200,000 sperm is combined with about 100 µl of *Xenopus laevis* frog egg extract containing the detectable labeling compound at a concentration of about 80 µCi/ml, monitoring sperm decondensation (preferably for about 5 to about 15 minutes) and DNA synthesis (preferably for about 2–3 hours) of the test sperm sample and the control sperm sample in a volume of *Xenopus laevis* frog egg extract, comparing the sperm decondensation and DNA synthesis of the test sperm sample to the control sperm sample, and determining the presence of abnormal sperm wherein abnormal sperm in the reduced test sperm sample demonstrate 80% or less sperm chromatin decondensation and 80% or less DNA synthesis as compared to sperm chromatin decondensation and DNA synthesis in reduced control sperm, as part of a screening regimen for diagnosing infertility in the human male partner of the unexplained infertile human couple.

An alternative method for diagnosing infertility according to the present method is also provided. This method for diagnosing infertility in a human male partner of an unexplained infertile human couple comprises the steps of preparing a modified *Xenopus laevis* frog egg extract capable of inducing human sperm chromatin decondensation, DNA synthesis and sperm chromatin recondensation, obtaining a sperm sample from the human male partner of an unexplained infertile human couple to provide a test sample, preparing the test sample for analysis of sperm chromatin decondensation, monitoring sperm chromatin decondensation in a volume of a non-mammalian egg extract for at least about 5 minutes, comparing the sperm chromatin decondensation of the test sperm sample to the control sperm sample sperm decondensation, and diagnosing infertility in a human male partner of the unexplained infertile human couple where the test sample demonstrates 80% or less of the chromatin decondensation demonstrated in a controlled sperm sample from a proven fertile human male. Preferably, the non-mammalian egg extract is a *Xenopus laevis, Rana pipiens*, or *Bufo jabanicus* egg extract. However, any species that produces eggs such that enough sperm activation factors can be obtained to perform the in vitro HSAA may be used as a source of non-mammalian egg extracts in the practice of the present invention. For example, such includes extracts and preparations from sea urchin eggs or clam eggs.

Preparing the test sample from an unexplained infertile human male may be further defined as comprising the steps of permeabilizing the test sperm sample in a nuclear isolation medium containing about 0.05 % lysolecithin and about 1 $\mu$g/ml soybean trypsin inhibitor for about 5 minutes at about 22° C. to provide a permeabilized test sperm sample, washing the permeabilized test sperm sample in a volume of nuclear isolation medium containing about 3% bovine serum albumin, pelleting and washing a second time the permeabilized test human sperm sample in a volume of nuclear isolation medium containing about 0.04% bovine serum albumin, reducing a number of the washed test sperm sample in a volume of XEIM including about 50 mM dithiothreitol for about 45 minutes at about between 0° C. to about 4° C., and labeling the permeabilized reduced test sperm sample in the presence of a detectable labeling compound contained within a volume of *Xenopus laevis* frog egg extract. The detectable labeling compound is most preferably $^3$H-TTP, this labeling compound contained at a concentration of about 80 $\mu$Ci/ml within a *Xenopus laevis* frog egg extract.

The present inventive methods also provide a toxicological screen for human sperm damage, the method comprising in one aspect obtaining a sample of human sperm from a patient exposed to a toxic agent to provide a test sample, preparing the test sample for analysis of sperm decondensation in a non-mammalian egg extract, and determining the percent of decondensed nuclei in the test sample present at a time point where at least 80% of sperm nuclei in fertile human sperm have decondensed in the non-mammalian egg extract. According to this method, sperm damage in the test sample will be identified where a percentage of test sample decondensation less than 80% of the percent of fertile sperm decondensation in the non-mammalian egg extract is observed. Even more preferably, where test sperm decondensation is observed to be less than about 85% or about 90% of fertile human sperm decondensation, a positive test for the identification of sperm damage in the test sample may be identified.

Turning now to still another aspect of the claimed invention, a method for screening varicocele human male patients as part of a regimen for screening patients for the need for varicocelectomy is defined. This screening method comprises preparing a sperm sample from the varicocele male for analysis of chromatin decondensation in a non-mammalian egg extract, determining the percent of decondensed nuclei in the test sample present at a time point where at least 80% of the sperm nuclei in fertile human sperm have decondensed in the non-mammalian egg extract, and comparing the amount of sperm decondensation observed in the test sample and in the known fertile sample. A percentage of test sample sperm decondensation less than 80% of the percentage of fertile sperm decondensation according to the claimed method will identify a potential candidate for varicocelectomy. Varicocelectomy in such patients has been observed as a potential therapeutic regimen for enhancing the fertility of varicocele patients. In most preferred aspects of practicing the present method, a percentage of test sample sperm decondensation less than about 80% or about 85% or about 90% of the percentage of fertile sperm decondensation is used to identify a potential candidate for varicocelectomy. Of course, because such patients typically have relatively lower sperm counts, the assay will be scaled down so as to accommodate the use of the assay with a sperm sample containing about 400,000 or 1 million sperm and 5 or about 10 million sperm and, in any event, less that the typical 20 million sperm, in conducting the assay. The HSAA may also be used to examine samples from males that are oligozoospermic, but who otherwise have normal sperm counts. While any non-mammalian egg extract is expected to be potentially useful in the method, a *Xenopus laevis* frog egg extract is most preferred.

A "reduced" chromatin decondensation, DNA synthesis or recondensation level is defined as less than 80% or less of the decondensation, DNA synthesis or recondensation demonstrated in the control sperm sample from sperm of a proven fertile human male over an equal incubation period and under the same sperm in vitro conditions.

A diagnostic kit for screening human males for infertility is also disclosed. In a preferred embodiment of the diagnostic kit comprises a carrier means adapted to receive at least four container means therein, a first container means containing a volume of dithiothreitol, a second container means containing a volume of lysolecithin, a third container means containing a *Xenopus laevis* frog egg extract, a fourth container means containing a control sample having a capacity for human sperm activation from a proven fertile human male, and at least two container means suitable for including therein a volume of up to 1 ml of a human sperm sample. The kit also most preferably includes a written instruction sheet defining the diagnostic test steps to be employed for screening human males for infertility using the kit.

The *Xenopus laevis* frog egg extract of the kit in some embodiments is to be prepared fresh, and in this embodiment will remain stable and sufficiently active for use in the screening assay for, in some cases, about 2 days stored at about 0° C. to about 4° C. ("on ice") (unfrozen). Alternatively, the frog egg extract may be frozen, or simply shipped frozen with the kit. In still another embodiment, the kit may be shipped without the *Xenopus laevis* frog egg extract, with the *Xenopus laevis* egg extract provided upon a proposed date of assay to assure maximum activity. Activity of the egg extract may be enhanced by including protease inhibitors in the egg extract, as discussed below.

The *Xenopus laevis* frog egg extract may most preferably also be treated with a protease inhibiting substance(s) effective for reducing loss of sperm activation potential of the extract. Such will enhance the shelf life of the kit and the assay in general as described in all of the embodiments disclosed herein.

In still another embodiment of the described kit, reagents and materials for the preparation of fixed cytoprep slides of both a test sperm sample and a control sperm sample is provided. For such an embodiment, the kit would also comprise at least two glass slides and at least two filter cards. Even more preferably, the kit includes at least 6 glass slides and at least 6 filter cards. Thus, cytoprep analysis may be performed for the test sperm sample and control sperm sample at the 15 minute incubation time (for smeared sperm nuclei analysis), at the 2 hour incubation time (to determine and compare relative DNA synthesis), and at the 3 hour incubation time (to determine and compare recondensation).

The kit in still another embodiment may comprise an autoradiography emulsion, an autoradiography developer, an autoradiography fixer and a Giemsa blood staining solution. The kit may also optionally comprise a container means including a volume of bovine serum albumin.

These results provided by the present inventor also demonstrate that human sperm chemically damaged in vitro respond abnormally in the HSAA; sperm treated with the crosslinking agent do not decondense. The damage was shown to be due, at least in some aspects, to covalent crosslinks, as hydroxylamine treatment reversed the damage. These results demonstrate that the HSAA also provides for a screening method for detecting sperm chemically damaged in vivo by toxicant exposure, such as for example, damage due to covalent crosslinking agents.

The invention also provides preparations of frozen *Xenopus laevis* frog egg extract, and a process for obtaining same, that has retained activity for monitoring the various human sperm activation events detailed herein. In some embodiments, this process comprises preparing a *Xenopus laevis* frog egg extract as described herein, filtering an amount of the *Xenopus laevis* extract, such as through a 0.45 micron filter, and adding the filtered *Xenopus laevis* frog egg extract dropwise to a volume of liquid nitrogen to provide frozen drops of the *Xenopus laevis* frog egg extract; and frozen drops of the egg extract may then be stored until time of use suspended in liquid nitrogen. When needed for use in the assay, or any other procedure, the extract will be thawed. As shown in the data provided herewith, the frozen and thawed egg extract maintains substantially all its activity for supporting the human sperm activation events of chromatin decondensation, DNA synthesis, and chromatin recondensation characteristic of proven fertile human sperm and test sperm samples (see Example 28).

As used in the description of the present invention, a human male of "proven" fertility is defined as a male whose sperm is known to be capable of fertilizing a human egg, for example, a sperm sample from a human male who has sired a child (a "proven breeder"). Even more fully defined, a proven fertile human male for purposes of describing the present invention is defined as a human male who has recently achieved a pregnancy within 12 months of their partner ceasing contraception.

The term "unexplained infertility" as used in the description of the present invention as pertains to a male partner of an "undiagnosed infertile" couple, is defined as a human male whose sperm sample demonstrates normal sperm concentration (count), sperm mobility, sperm morphology, characteristic of a proven fertile human male[4] and having been involuntarily infertile for at least 2 years.

The proven fertile male sperm samples need not necessarily be tested for sperm motility following ejaculation as stored sperm may be used in the assay with equal efficacy. However, the control samples are examined for normal sperm count and sperm morphology.

Abbreviations used throughout the description of the present invention include:

NIM=Nuclear Isolation Medium
XEIM=Xenopus extract isolation medium
TTP=Methyl-$^3$H thymidine 5'-triphosphate
SPA=Sperm Penetration Assay
HSAA=Human Sperm Activation Assay
GIFT=Gamete Intrafallopian Transfer
DTT=Dithiothreitol
IVF-ET=In vitro fertilization—embryo transfer
ART=Assisted reproductive technology
IUI=intrauterine insemination

BRIEF DESCRIPTION OF THE DRAWINGS

FIGS. 1A–1H FIGS. 1A–1B are phase contrast micrographs. FIGS. 1E–1H are bright field micrographs of Giemsa-stained nuclei. FIG. 1G is a Giemsa-stained autoradiograph. 1A and 1E: Time zero. 1B; and 1F: 15 minutes incubation. 1C and 1G: 2 hour incubation. 1D and 1H: 3 hour incubation. Bar, 10 μm.

FIGS. 4B–4F show examples of the variable decondensation and labelling observed in Patient #15 sperm nuclei. 4B. Nuclei neither decondensed, nor labelled (41%). 4C. Nucleus decondensed and labelled (14%). 4D. Nucleus decondensed and unlabelled (8%). 4E. Nucleus decondensed, smeared and unlabelled (7%). 4F. Nucleus decondensed, smeared and labelled (30%). Bar, 10 μm. Micrographs were photographed at 800×magnification using a Zeiss Photomicroscope III.

FIGS. 7B and 7C demonstrate a sperm that did not decondense alongside a partially decondensed sperm. Fully decondensed sperm are shown in FIGS. 7D and 7E.

FIGS. 10A–10E. Phase contrast photographs of nuclei having normal and abnormal decondensation in the HSAA, taken using a 40X objective. Bar, 10 μm. (A) Time Zero. Permeabilized sperm from a fertile male with no extract treatment. (B, C, D) Permeabilized sperm from a male with unexplained infertility (UI) incubated 15 minutes in egg extract. In B is shown an example of a sperm that did not decondense, near a partially decondensed sperm. Another partially decondensed sperm is shown in C. A fully decondensed sperm is shown in D. The idiopathic infertile male whose sperm are shown in B-D had a decondensation score that was 57% of the control. (E) A fully decondensed sperm from a fertile male incubated 15 minutes in egg extract.

FIGS. 11A–11D. Photographs of Giemsa-stained cytopreps (A,B) and autoradiographs (C,D) of nuclei having normal and abnormal decondensation and DNA synthesis in the HSAA; a 63X oil emersion objective was used. Bar=10 μm. For A and B, sperm were incubated 20 minutes in egg extract before cytopreps were made. (A) Examples of typical smeared nuclei seen in cytopreps of sperm from fertile males. (B) Examples of the smeared nuclei observed in cytopreps of sperm from males with unexplained infertility (UI); this sperm had a decondensation score that was 50% of the control. The single arrow points to a nondecondensed sperm nucleus that did not smear, and the double arrows point to a partially decondensed and smeared sperm nucleus. Both of these sperm nuclei are next to a sperm nucleus smeared equivalent to that observed in A. For C and D, sperm were incubated 2 hours in extract containing tritiated thymidine before preparation of cytopreps and autoradiography. (C) Example of a labelled sperm nucleus from a fertile male. (D) Example of unlabelled sperm nuclei from a male with unexplained infertility (UI) whose sperm had an abnormal DNA synthesis response in the HSAA (15% of the control).

DETAILED DESCRIPTION OF THE PREFERRED EMBODIMENTS

Figure 2A:
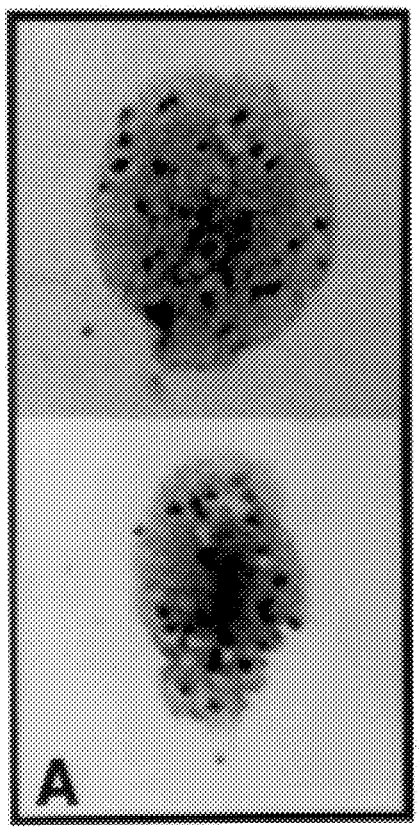
FIGS. 2A–2B Bright field photographs of Giemsa-stained autoradiographs of sperm nuclei following 2 hours of incubation in frog egg extract. 2A. Fertile control labelled nuclei. 2B. Patient #6 unlabelled nuclei. Bar, 10 μm. Micrographs were photographed at 800×magnification using a Zeiss Photomicroscope III.

The present invention provides a unique method for assessing the fertilizing capacity of a sample of human sperm. A method for using such a method as a diagnostic screening test for human couples having an undiagnosed inability to conceive despite exhaustive standard fertility screening procedures, is also provided.

The development of an in vitro human sperm activation assay (HSAA) now makes it possible to study the molecular mechanisms of human sperm activation, and also provides the basis for a new diagnostic tool to study idiopathic male infertility.

The HSAA uses Xenopus egg extract from unfertilized eggs arrested at the second meiotic metaphase. The frogs can be induced every two months to produce substantial numbers of relatively large eggs (1.2 mm diameter) at all times of the year, thus providing milliliter amounts of egg extract; 1 ml is sufficient for 10 assays. The extract contains all the factors necessary for sperm activation, including nucleoplasmin that is required for decondensation and protamine/histone exchange, cyclins and cyclin-dependent kinases that direct the cell cycle traverse, and the components needed for pronuclear assembly and DNA synthesis.

In the HSAA, the human sperm activation events occur in a time frame determined by factors in the frog egg. After fertilization, a Xenopus frog sperm takes 1.5 hours for complete activation in vivo, a process which, as with human sperm, requires 3 hours upon incubating with frog egg extract in vitro.

The "fertilizing" capacity of a sample of human sperm obtained from any particular male has been shown by the inventor to, on some occasions, change from incapable of supporting fertilization to fully capable of fertilizing the egg sufficient to allow the development of the fertilized egg to a two cell stage embryo, using the present methods. Therefore, the present invention also provides for a system of evaluating a potential sperm donor's sperm sample for fertilizing capacity prior to the use of the sperm for use in assisted reproductive technologies (zoned drilling, hatching, IVF, GIFT, ZIFT, direct injection of sperm nuclei, IUI, etc.).

A diagnostic kit for evaluating the fertilizing capacity of a human sperm sample for a human egg is also provided.

Lysolecithin employed in permeabilizing sperm samples was obtained from Sigma Chemical Company (L-α-Lysophosphatidylcholine, Sigma No. L-4129, from egg yolk, type 1, approximate purity 99%). Bovine serum albumin was also obtained from Sigma (BSA, Sigma No. A-7906, 98–99% albumin). Soybean trypsin inhibitor was obtained from Boehringer Mannheim, No. 109 886. Dithiothreitol, DTT, (also called Cleland's reagent) was obtained from Calbiochem, No. 233155.

For cytoprep analysis, filter cards were obtained from Shandon Inc., (SCA-0005). Giemsa stain was obtained from Baker (Catalog No. M,708-01). For autoradiography, the Kodak NTB2 autoradiography emulsion was obtained from International Biotechnologies, Inc. (IBI, No. 1654433). Kodak developer was obtained from International Biotechnologies, Inc. as well (D-19, CAT 146-4593). Kodak fixer was also obtained from this source (CAT No. 197-1746).

The detectable labeled compound $^3$H-TTP was obtained from I.C.N. (Catalog No. 24044H, Irvine, Calif.).

Various chemicals employed in preparing the nuclear isolation medium, XEIM and Barth's Medium, such as $MgCl_2$, KCl, $MgSO_4$, $Ca(NO_3)_2$, $CaCl_2$, Tris-HCl. Penicillin and streptomycin were obtained from Gibco. Cysteine-HCl, maleic acid and sucrose were obtained from Sigma Chemical Company.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are presented to describe preferred embodiments and utilities and to satisfy "best mode" requirements of the present invention, but should not be construed as limiting the claims thereof.

EXAMPLE 1

Preparation of *Xenopus laevis* Frog Egg Extract

The present example is provided to define the most preferred embodiment of the particular *Xenopus laevis* frog egg extract found to provide the enhanced method of determining/detecting the cause of unexplained infertility in a human male. The herein described optimal method for isolating the egg extract provides for the sequential potent and definitively observable inducement of the three events characteristic of sperm activation, which are 1) sperm nuclear chromatin decondensation, 2) DNA synthesis and 3) sperm nuclear chromatin recondensation.

Pretreatment of permeabilized human sperm at a concentration of about 25,000 sperm/μl in the XEIM described herein, containing 50 mM DTT for about 45 minutes on ice, before mixing with the *Xenopus laevis* frog egg extract was found to enhance the decondensation and DNA synthesis events.

To promote oocyte maturation, ovulation and egg laying, adult female *Xenopus laevis* frogs were injected with 500IU of human chorionic gonadotropin in the morning and evening of the day preceding the experiment. Mature eggs were collected and dejellied with 2% cysteine-HCl, pH 7.6. The eggs were then rinsed and incubated for about between 30 minutes to 1 hour at room temperature (22° C.) in Barth's medium comprised of 88 mM NaCl, 1.0 mM µg/ml penicillin, 10 µg/ml streptomycin and 2.4 mM $Na(CO_3)_2$. The eggs were washed three times in XEIM. Excess buffer was removed and the eggs lysed by centrifugation at 10,000 g, 4° C., for 15 minutes in a swinging bucket rotor. The resulting middle layer between the lipids and the egg pellet was removed from the centrifuge tube, recentrifuged, and the resulting middle layer used as the stock extract solution. The extract was stored on ice until used for the HSAA.

EXAMPLE 2

Method for Diagnosing Unexplained Infertility as a Dysfunction of Human Sperm Preparation The present example is provided to demonstrate a most preferred method for diagnosing unexplained infertility from a sperm sample.

All semen donors whose samples will be employed as "control" samples (proven fertile males as determined from the successful conception of at least 1 child) will have abstained from ejaculation for at least 2 days prior to the collection of the semen samples. Semen samples will be obtained by masturbation and stored in a refrigerator at about 4° C. until the date of assay. Such refrigerated sperm samples stored at 4° C. from proven fertile males for up to month (30 days) were found to respond the same as did sperm freshly collected from the same male on the date of testing in the human sperm activation assay described herein.

Semen samples from unexplained infertility patients will be obtained from various infertility clinics throughout the country and the HSAA will be performed as described below. We will purchase normal, control semen samples from fertile males. Fresh samples are not needed for the HSAA, as stored semen samples from a fertile male were found to respond the same in the human sperm activation assays as did sperm collected from the same fertile male on the day the assay was performed, even after a 4° C. storage of up to a month (data not shown).

On the day that the diagnostic method is to be performed, the samples are incubated for 30 minutes at 37° C.; each sample is then suspended in 10 ml of nuclear isolation medium (NIM, 200 mM sucrose, 2.4 mM $MgCl_2$, 10 mM Tris-Hcl and 5 mM maleic acid, pH 7.4). A sperm count is taken and an aliquot (containing 20 million sperm) is pelleted in a centrifuge for 10 minutes at 400×g, then resuspended in 10 ml of NIM containing 0.05% lysolecithin and 1 µg/ml soybean trypsin inhibitor. The mixture is kept at room temperature for 5 minutes and the sperm repelleted as before, then washed, first in NIM with 3% BSA and then with NIM containing 0.4% BSA, as described by Lohka and Masui[1]. Sperm will finally be suspended in Xenopus Extract Isolation Medium (XEIM, 10 mM Tris-HCL, pH 7.5, 1.5 mM $MgCl_2$, 100 mM KCl and 50 mM DTT) at a concentration of 25,000 sperm/µl and kept on ice (between 0° C. and 4° C.) for 45 minutes before mixing with the frog egg extract. This XEIM (DTT) pretreatment was found to enhance the decondensation and DNA synthesis events. Such may be the result of reducing the protamines that in mammalian sperm are cross-linked by intermolecular disulfide bonds.[6,7]

Sperm contain "intermediate" protaextract lacks the reducing factor(so the frog egg extract lacks the reducing factor(s) found in mammalian eggs that are required for reducing the disulfide bridges of the human sperm.[5,6] The disulfide bonds were therefore reduced experimentally by including DTT in a pretreatment incubation medium described as a XEIM. The preincubation of the test sperm sample and the control sperm sample also was found by the present inventor to enhance the decondensation and DNA synthesis "activation" events.

The sperm permeabilization is required in order for the sperm nuclear chromatin to be in direct contact with the sperm factors in the egg extract, thus inducing sperm activation.

Egg Extract Isolation

To promote oocyte maturation, ovulation and egg laying, adult female *Xenopus laevis* frogs are injected with 500IU (in a volume of 500 µl) of human chorionic gonadotropin in the morning and evening of the day preceding the experiment. Alternatively, adult female frogs are injected once on the afternoon preceding the day of the experiment, i.e., egg harvesting, without any significant decrease. Mature eggs are then collected and dejellied with 2% cysteine-HCl, pH 7.6. Ovulated eggs harvested directly from the frogs on the day of the assay are employed, rather than eggs spontaneously released by a frog into a tank at undetermined times following injection of hCG. For example, such eggs are preferably collected by squeezing the injected female frogs to obtain mature ovulated eggs, i.e., fresh-squeezed eggs. The eggs are then rinsed and incubated for one hour at room temperature in Barth's medium comprised of 88 mM NaCl, 1.0 mM KCl, 0.83 mM $MgSO_4$, 0.34 mM Ca $(NO_3)_2$, 0.41 mM $CaCl_2$, 7.5 mM Tris-HCl, pH 7.6, 10 µg/ml penicillin, 10 µg/ml streptomycin and 2.4 mM $Na(CO_3)_2$. The eggs are washed three times in Xenopus Extract Isolation Medium (XEIM, 10 mM Tris-HCL, pH 7.5, 1.5 mM $MgCl_2$, 100 mM KCl and 50 mM DTT). Excess buffer is removed and the eggs lysed by centrifugation at 10,000 g, 4° C., for 15 minutes in a swinging bucket rotor. The resulting middle layer between the lipids and the egg pellet is removed from the centrifuge tube, recentrifuged, and the resulting middle layer used as the stock extract solution. The extract is stored on ice until used for the HSAA.

The procedure described by Lohka and Masui for the preparation of the egg extract was modified, as the *Rana pipiens* egg extract prepared and used therein employed an isolation medium included 250 mM sucrose (not needed in the claimed system), 200 mM KCl (the present assay uses 100 mM for optimal results), 1.5 mM $MgCl_2$, 2.0 mM Beta-mercaptoethanol (the present assay uses a much higher concentration of a different reducing agent called dithiothreitol or DTT, for the same reasons that were discussed above for the DTT pretreatment of the sperm) and 10 mM tris-HCl at pH 7.5 (the same concentration is used).

Human Sperm Activation Assay (HSAA)

Permeabilized, reduced sperm from the normal control and infertility patients are mixed separately with *Xenopus laevis* frog egg extract at a concentration of 200,000 sperm/ 100 µl of extract. The permeabilized reduced sperm is incubated at about 19° C. (i.e., about 18° C. to about 24°) in 100 µl of extract containing $^3$H-TTP at a concentration of 80 µCi/ml. Chromatin decondensation, DNA synthesis and chromatin recondensation is then evaluated.

Phase-contrast microscopy is used to assess chromatin decondensation and recondensation. Aliquots (5 µl) are taken, placed on glass slides, and covered with glass coverslips at 5 and 10 minutes and at 3 hours following the addition of the sperm to the frog egg extract. At the 5 and 10 minute time point, the percentage of sperm that have decondensed is determined (50 sperm per sample are scored during the assay at both the 5 and 10 minute time points). Between 95–100% of the control sperm have normally decondensed within 5–10 minutes.

Recondensation of chromatin of the sperm nuclei is determined at the 3 hour time point (again, 50 sperm will be scored per sample). Recondensation is typically observed in 95–100% of the control sperm. DNA synthesis in the sperm nuclei is assessed using a 25-$\mu$l aliquot taken at the 2 hour time point and diluted with 75 $\mu$l of phosphate-buffered saline. The sperm is then affixed to glass slides by centrifugation, dried, and fixed for 5 minutes in Carnoy's fixative (three parts ice-cold methanol to one part glacial acetic acid). These fixed cytopreps are then dipped in 42° C. Kodak nuclear track emulsion (NTB-2), stored at 4° C. for two weeks, and then following development (2 minutes in Kodak D-19 developer followed by 2 minutes in Kodak Fixer) are Giemsa stained through the emulsion (45 minutes in 2.5% Giemsa stain in phosphate buffer). Approximately 200 nuclei were scored for labelling and the results with control sperm (% of the nuclei showing label above background) compared to those with the patients' sperm.

Cytopreps of the sample sperm specimens (and the corresponding control sperm specimens) were also prepared at the 15 minute time point, and the relative amount of chromatin smearing assessed (an indicator of the extent of chromatin decondensation). Cytopreps prepared at the three hour time point were prepared as a measure of chromatin recondensation. The cytopreps were prepared and fixed as previously described followed by Giemsa staining without autoradiography. All microscopy is done using a Leitz Orthoplan microscope.

All samples from the infertility patients that are found to respond normally in the HSAA are reported as normal to the infertility clinic that sent the sample. Any abnormal responses will also be reported to the infertility clinic that sent the sample.

EXAMPLE 3

Clinical Testing For Unexplained Infertile Male Sperm Samples

The present example provides a clinical study wherein 20% of sperm samples obtained from the male partners of couples previously diagnosed as inexplicably infertile, were diagnosed as relating to sperm inadequacy for sperm activation events, particularly sperm decondensation and DNA synthesis.

MATERIALS AND METHODS

Unexplained Infertility Patients

For the inventor's clinical studies, a couple was diagnosed as having unexplained infertility, when the following conventional tests have been completed without finding a cause for the couple's infertility; the female partner will have undergone complete infertility evaluations including postcoital tests (to rule out sperm motility loss in cervical mucus); a timed endometrial biopsy (to exclude luteal phase defect); a hysterosalpingogram (to establish tubal patency,) and laparoscopy (to rule out pelvic pathology); in the male partner, semen analysis would have been normal on two occasions with sperm concentrations greater than 20 million/ml, total sperm numbers of 40 million or more, sperm motility greater than 60% and normal morphology in more than 60% of the sperm.[4] The inexplicably infertile couples must also have been involuntarily infertile for over two years.

In this study, sperm was obtained from 15 unexplained infertility patients that have been involuntarily infertile for more than 5 years (average of 7.3 years, range of 5 to 10 years). All of the semen samples from the unexplained infertility patients that were analyzed in this study had normal sperm concentrations, total sperm counts, and morphology.

Human Sperm Preparation

All semen donors abstained from ejaculation for 2 days prior to the collection of the semen samples that were obtained by masturbation.

Semen samples from 15 unexplained infertility patients were obtained at the time of the regularly scheduled procedures at an interfertility clinic (e.g., SPA; IVF-ET; and GIFT). A portion of the sample not used for these procedures was used for the HSAA. These samples were kept in a 4° C. refrigerator for up to 7 days for parallel weekly assays on samples collected throughout the week. Semen samples from 15 fertile males were stored from 1–7 days mimicking the storage conditions of the semen samples from the unexplained infertility patients. Fresh samples are not needed for the HSAA, as stored semen samples from a fertile male were found to respond the same in the human sperm activation assays as did sperm collected from the same fertile male on the day the assay was performed, even after 4° C. storage of up to a month.

On the day of the diagnostic test, semen samples were incubated for 30 minutes at 37° C.; each sample was then suspended in 10 ml of nuclear isolation medium (NIM, 200 mM sucrose, 2.4 mM $MgCl_2$, 10 mM Tris-HCl and 5 mM maleic acid, pH 7.4). A sperm count was taken and an aliquot (containing 20 million sperm) was pelleted in a centrifuge for 10 minutes at 400×g, then resuspended in 10 ml of NIM containing 0.05% lysolecithin and 1 $\mu$g/ml soybean trypsin inhibitor.

The mixture was kept at room temperature for 5 minutes and the sperm repelleted as before, then washed, first in NIM with 3% BSA and then with NIM containing 0.4% BSA, substantially as described by Lohka and Masui.[1] Sperm were finally suspended in Xenopus Extract Isolation Medium (XEIM, 10 mM Tris-HCL, pH 7.5, 1.5 mM $MgCl_2$, 100 mM KCl and 50 mM DTT) at a concentration of 25,000 sperm/$\mu$l and kept on ice for 45 minutes before mixing with the frog egg extract. This XEIM (DTT) pretreatment was found to enhance the decondensation and DNA synthesis events, presumably by reducing the protamines that in mammalian sperm are cross-linked by intermolecular disulfide bonds.[6,7]

Xenopus laevis sperm contain "intermediate" protamines that are not cysteine rich, so the frog egg extract lacks the reducing factor(s) found in mammalian eggs that are required for reducing the disulfide bridges of the human sperm; the disulfide bonds will thus be reduced experimentally.[5,6]

Xenopus laevis Egg Extract Isolation

To promote oocyte maturation, ovulation and egg laying, adult female Xenopus laevis frogs were injected with 500IU of human chorionic gonadotropin in the morning and evening of the day preceding the experiment. Mature eggs were collected and dejellied with 2% cysteine-HCl, pH 7.6. The eggs were then rinsed and incubated for one hour at room temperature in Barth's medium comprised of 88 mM NaCl, 1.0 mM KCl, 0.83 mM $MgSO_4$, 0.34 mM Ca $(NO_3)_2$, 0.41 mM $CaCl_2$, 7.5 mM Tris-HCl, pH 7.6, 10 $\mu$g/ml penicillin, 10 $\mu$g/ml streptomycin and 2.4 mM $Na(CO_3)_2$. The eggs were washed three times in XEIM. Excess buffer was removed and the eggs lysed by centrifugation at 10,000 g, 4° C., for 15 minutes in a swinging bucket rotor. The resulting middle layer between the lipids and the egg pellet was removed from the centrifuge tube, recentrifuged, and the resulting middle layer used as the stock extract solution. The extract was stored on ice until used for the HSAA.

Human Sperm Activation Assay (HSAA)

Permeabilized sperm from the normal control and infertility patients were mixed separately with frog egg extract at a concentration of 150,000 sperm/150 µl of extract. The permeabilized sperm were incubated at 19° C. in extracts containing $^3$H-TTP at a concentration of 80 µCi/ml. Chromatin decondensation, DNA synthesis and chromatin recondensation were evaluated. Phase-contrast microscopy was used to assess chromatin decondensation and recondensation. Aliquots (5 µl) were taken, placed on glass slides, and covered with glass coverslips at 5 and 10 minutes and at 3 hours following the addition of the sperm to the frog egg extract.

a. Sperm Decondensation

At time intervals of 5 and 10 minutes, the percentage of sperm that had decondensed (FIG. 1B) was determined. Between 95–100% of the control sperm were normally decondensed within 5 minutes. At the 10 minute time point, between 95–100% normally have the appearance of the nucleus shown in FIG. 1B. At the 3 hour time point, it was determined if the sperm nuclei had recondensed their chromatin as is seen by the smaller nucleus shown in FIG. 1D when compared to the nucleus shown in FIG. 1B. Recondensation was typically observed in 95–100% of the control sperm.

b. DNA Synthesis

DNA synthesis in the sperm nuclei was assessed using 20 µl aliquots taken at the 2 hour time point and diluted with 50 µl of phosphate-buffered saline. The sperm were then affixed to glass slides by centrifugation, dried, and fixed for 5 minutes in Carnoy's fixative (three parts ice-cold methanol to one part glacial acetic acid). These fixed cytopreps were then dipped in 42° C. Kodak nuclear track emulsion (NTB-2), stored at 4° C. for two weeks, and then following development were Giemsa stained through the emulsion.

C. Sperm Recondensation

Cytopreps were also prepared at the three hour time point to see if the chromatin had recondensed to the level shown in FIG. 1G.

The cytopreps were prepared and fixed as previously described followed by Giemsa staining without autoradiography. All microscopy was done using a Leitz Orthoplan microscope. The micrographs in FIGS. 1–4 were photographed at 800×magnification using a Zeiss Photomicroscope III. Two hundred nuclei were scored for labelling and the results with control sperm (% of the nuclei showing label above background) compared to those with the patients' sperm.

RESULTS

Normal Sperm (Control) Response in the HSAA

A pictorial representation of a normal response of permeabilized human sperm to the frog egg extract is shown in FIGS. 12A–14A. The sperm nuclei shown in FIGS. 1A–D and 1E–1H were photographed (800×magnification) and printed at the same magnification, with the bar representing 10 µm. Phase contrast microscopy was used when photographing the nuclei shown in FIGS. 1A–D, while FIGS. 1E–H are bright field photographs of Giemsa-stained cytopreps, with the nuclei shown in FIG. 1G being Giemsa-stained autoradiographs. Permeabilized sperm without extract treatment are shown in FIGS. 1A and 1E. Following a 5 minute incubation in the frog egg extract, greater than 90% of the sperm are decondensing. After a 10–15 minute incubation in the extract, greater than 95% of the sperm have completely decondensed nuclei. A typical completely decondensed sperm nucleus is shown in FIG. 1B. We have observed that at the 15 minute time point, the sperm nuclei do not remain intact during the cytocentrifugation procedure used when making cytopreps; the nuclei become smeared onto the glass slide (FIG. 1F). Following a 2 hour incubation in the frog egg extract, the sperm nuclei have begun to recondense their chromatin. Notice the decrease in size of the sperm nucleus shown in FIG. 1C as compared to the nucleus shown in 1B. The recondensed sperm nuclei also withstand the cytocentrifugation procedure, (note intact nuclei in FIG. 1G). The labelling of these nuclei indicates that they have undergone DNA synthesis. Typically, >95% of the control nuclei are labelled following a 2 hour incubation in frog egg extract containing $^3$H-TTP, while >95% are fully recondensed following a 3 hour incubation. Examples of recondensed nuclei are shown in FIGS. 1D and 1H.

Use of the HSAA in the Analysis of the Sperm Obtained From Fertile Males and Unexplained Infertility Patients In this study, sperm samples were obtained from 15 unexplained infertility patients and 15 fertile males and prepared for use in the HSAA as described in the Methods. In each HSAA, sperm from a fertile male (previously shown to produce sperm that has a normal response in the (HSAA) was also assayed as a parallel control. A rating system (Table 1) was developed to compare the HSAA responses of the control sperm sample to the sperm samples obtained from 15 unexplained infertility patients and 15 fertile males.

TABLE 1

Human Sperm Activation Assay Rating Scheme

| | % of Control | | | |
|---|---|---|---|---|
| | <40 | 40–60 | 60–80 | 80–100 |
| % Decondensing at 5 Minutes | – | + | ++ | +++ |
| % Decondensing at 10 Minutes | – | + | ++ | +++ |
| % Synthesizing DNA at 2 Hours | – | + | ++ | +++ |
| % Recondensing at 3 Hours | – | + | ++ | +++ |

A range of about 60–80% (or less) was considered an "abnormal" response.

The results of the pilot study are shown in Table 2. The data summarized in Table 2 demonstrates that three of the sperm samples from the infertility patients responded abnormally in the HSAA, whereas all sperm from known fertile men using conventional fertility measuring responded normally in the assay.

TABLE 2

Human Sperm Activation Assay Pilot Study Results

| | Decondensation (5 Minutes) | Decondensation (10 Minutes) | DNA Synthesis (2 Hours) | Recondensation (3 Hours) |
|---|---|---|---|---|
| Fertile males 1–15 | +++ | +++ | +++ | +++ |
| Infertility Patients 1–3, 5, 7–14 | +++ | +++ | +++ | +++ |
| Infertility Patient 4 | + | ++ | +++ | +++ |
| Infertility Patient 6 | +++ | +++ | – | +++ |
| Infertility Patient 15 | + | + | + | ? |

EXAMPLE 4

Diagnosis of Male Infertility and Delayed Sperm Decondensation

The present example is presented to demonstrate the use of the herein disclosed method for tracing a couple's infertility to a particular insufficiency of the male sperm decondensation process after entry into the egg cytoplasm. These data demonstrate that less than about 53 % of the patient sperm nuclei had decondensed relative to control sperm nuclei (after a 5-minute incubation) was characteristic of sperm obtained from the male partner of an "unexplained infertile" couple.

Sperm from patient number 4 sperm was obtained as described in example 2 and processed as described in example 3. Although scoring normal (60%) in the sperm penetration assay (SPA), this sperm sample had a diminished decondensation response (50% decondensed after 5 minutes of incubation in extract), by which normal human sperm demonstrated a 95% decondensation. After a 10-minute incubation, only 80% of the patient's number 4 sperm had decondensed. The HSAA for patient number 4's was repeated using the excess sperm from an unsuccessful GIFT attempt (4 eggs transferred), which resulted in a finding that 60% of these sperm decondensed after 5 minutes of incubation in the extract. After the same incubation period with normal (i.e., known fertile) sperm, 98% sperm decondensation was observed. Following a 10-minute incubation in the egg extract, 90% of the patient's sperm had decondensed, with 98% of the control sperm being decondensed.

When new samples of patient number 4's sperm were obtained for use in the HSAA at 4, 11, and 13 months following the initial analyses, this patient's sperm responded normally in the HSAA when compared to the control (fertile). During the time period where the patient's sperm was responding normally in the HSAA, an IVF-ET attempt resulted in a successful pregnancy, however, the pregnancy ended with a spontaneous miscarriage at six weeks of pregnancy. The sperm is from the male member of a couple that has been trying to conceive for 10 years; at present, with the exception of the present assay, the couple has been found to be normal in every test performed.

The five different semen samples (two showing abnormal HSAA responses, three responding normally) as obtained from patient 4 resulted in three normal HSAA results for reasons which are unknown at the present time.

HSAA may thus also be used to predict sperm efficacy when used in assisted reproductive technology attempts at pregnancy.

The sperm from the particular male No. 4 in this study is a member of a couple that had been trying to conceive for ten years and at the present, with the exception of the presently disclosed method, had presently been determined to be normal in every test performed.

EXAMPLE 5

Diagnosis of Male Infertility and Reduced Labeled Sperm Nuclei

The present example is provided to demonstrate the observance of a reduced number of labeled sperm nuclei following a 2 hour incubation in a *Xenopus laevis* frog egg extract as an indicator of infertility in a male partner of an "unexplained infertile" human couple.

Figure 2B:
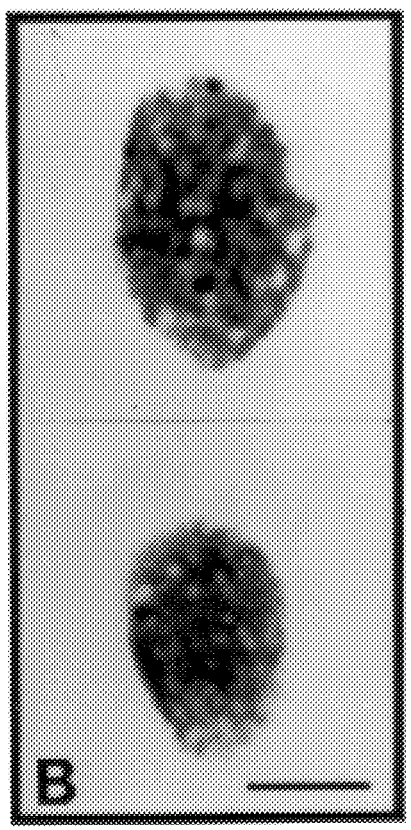

A sperm sample was obtained from patient No. 6 and processed as described in example 2. Patient No. 6 was the male partner in an "unexplained infertile" categorized human couple who had a history of attempting to achieve conception for 8 years. The sample was run in the HSAA as described in example 3. This particular sperm sample was found to decondense and recondense in a normal fashion. However, only 27% of the sperm nuclei were found to be labeled following autoradiography, while 100% of the control sperm nuclei were found to be labeled. Autoradiographies of typical labeled controlled nuclei and unlabeled patient nuclei are shown in FIGS. 2A and 2B, respectively.

The present example demonstrates that a reduction in the percentage of labeled sperm nuclei of at least 73% (i.e., 27% labelled nuclei relative to control (100%)) provides a positive diagnosis of human male infertility according to the presently disclosed methods. However, the estimate of what will be the "indicator" cutoff as <80% of the DNA synthesis observed in control nuclei is also considered a positive indication of male infertility.

EXAMPLE 6

Sperm Nuclei Smearing After Cytocentrifugation and Sperm Decondensation

The present example is provided to demonstrate the diagnosis of a previously unknown cause of infertility in a human male through observation of the percentage of decondensed sperm nuclei percentage of sperm nuclei "smearing" after cytocentrifugation of a sample observed with phase contrast microscopy at 5 and 10 minute intervals, and level of DNA synthesis with sperm of the patient, as compared to fertile control sperm levels.

A sample of sperm was obtained from a patient No. 15 and processed substantially as described in example 2. The sperm sample from patient No. 15 responded variably in the rate and extent of decondensation and DNA synthesis. Only 50% of the sperm had decondensed at both the 5- and 10-minute time point with 45% showing partial decondensation and 5% showing full decondensation. The cytopreps from the 15 minute time point are shown in FIGS. 3A–3B.

Figure 3A:
FIGS. 3A–3B. Bright field photographs of Giemsa-stained sperm nuclei following 15 minute incubations in frog egg extract. 3A. Fertile control, decondensed and smeared nuclei 3B. Patient #15, 3 nuclei that are neither smeared nor decondensed by a decondensed smeared nucleus. Bar, 10 μm. Micrographs were photographed at 800×magnification using a Zeiss Photomicroscope III.
Figure 3B:
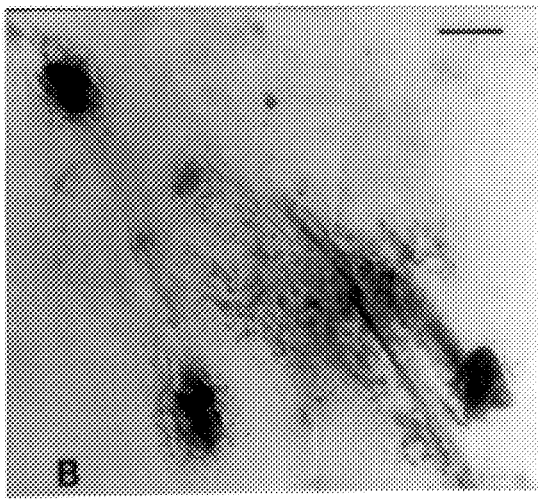

In FIGS. 3A, is shown the typical smearing of the sperm nuclei seen from control normal (known fertile) sperm in the HSAA. In FIG. 3B are shown sperm nuclei from patient No. 15, with three intact sperm nuclei and one smeared nucleus. Sperm nuclei that are not decondensing maintain their nuclear structure during cytocentrifigation, while decondensing sperms smear on the glass slide.

Figure 4A:
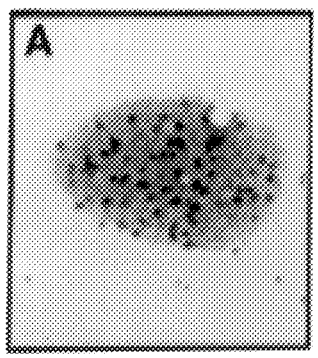
FIGS. 4A–4F. Bright field photographs of Giemsa-stained autoradiographs of sperm nuclei following 2 hours of incubation in frog egg extract. 4A. Fertile control, decondensed labelled sperm nucleus (96%).
Figure 4B:
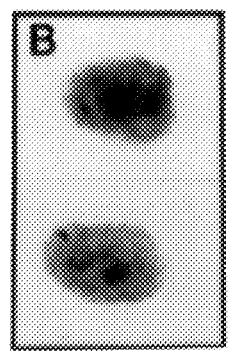
Figure 4C:
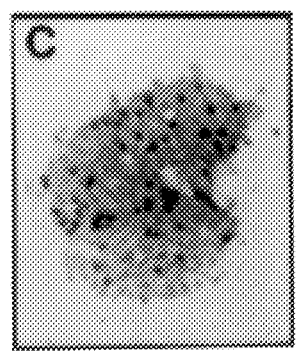
Figure 4D:
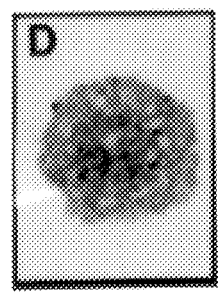
Figure 4E:
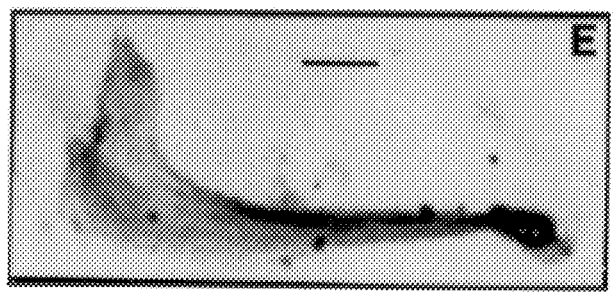
Figure 4F:
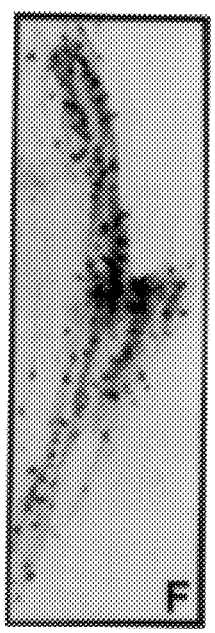
Figure 5A:
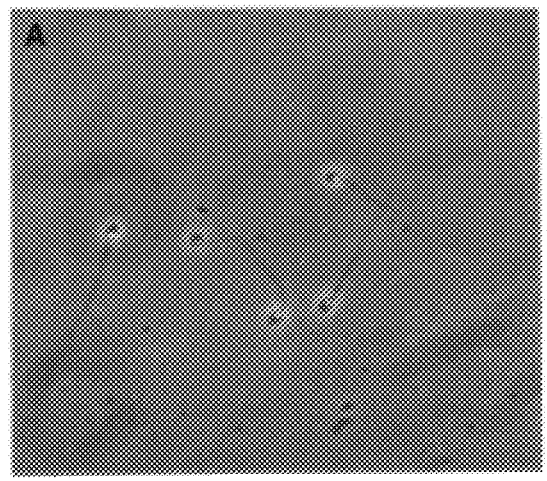
FIG. 5A–5B provides a pictorial representation of normal sperm both before (FIG. 5A) and after (FIG. 5B) a 15 minute incubation in the *Xenopus laevis* frog egg extract. These photographs were taken with lower magnification (200×) so that more sperm could be seen in the viewing field.
Figure 5B:
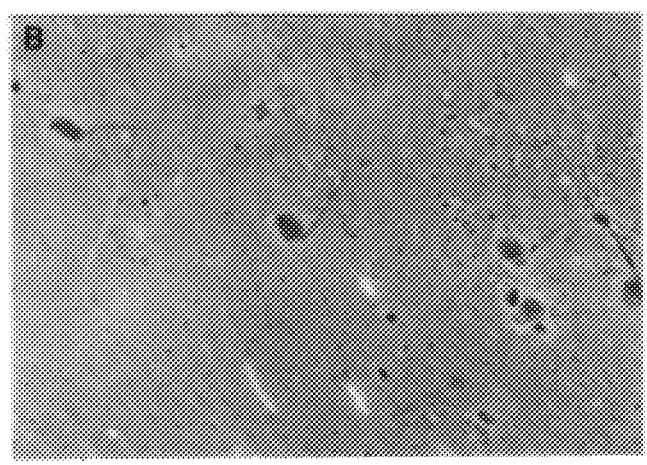

In FIGS. 4A–4F, it is shown the cytoprep-autoradiographies of sperm nuclei from a control fertile male (FIG. 4A) and from patients No. 15 (FIGS. 4B–F) that had been incubated in egg extract containing tritiated thymidine for 2 hrs. In the control labeled nuclei, 96% were found to be labeled. Nuclei from patient No. 15 demonstrated variable levels of decondensation, with 44% of the nuclei being labeled. 41% of the nuclei were neither decondensed nor labeled (FIG. 4B), 14% were decondensed and labeled (FIG. 4C), 8% were decondensed and unlabeled (FIG. 4D), 7% were smeared and unlabeled (FIG. 4E) and 30% were smeared and labeled (FIG. 4F).

The male and female counterpart of this couple had a history of failure to conceive for a period of seven years. The sperm penetration assay score obtained using patient No. 15 sperm sample was zero. When using donor sperm, the first attempt at artificial insemination of the female of this couple resulted in a pregnancy, indicating that the infertility experienced by the couple was linked to male sperm defect in function, specifically to the poor rate of sperm nuclei decondensation and lower amount of DNA synthesis after fertilization.

EXAMPLE 7

Diagnostic Human Sperm Testing Kit

The present prophetic example is provided to demonstrate a preferred embodiment of the proposed diagnostic kit to be used in the clinic or private laboratory to test sperm samples for possible infertility.

The following reagents will be employed in various embodiments of the claimed diagnostic kit.

For Sperm Permeabilization:
1. Nuclear Isolation Medium (NIM) 200 mM sucrose, 2.4 mM $MgCl_2$, 10 mM Tris-HCl, and 5 mM maleic acid, pH 7.4.
2. Lysolecithin (L-α-Lysophosphatidylcholine, Sigma, No. L-4129) from egg yolk, Type I, Approx. 99%.
3. Bovine Serum Albumin (BSA) from Sigma, No. A-7906, 98–99% albumin.
4. Soybean Trypsin Inhibitor from Boehringer Mannheim, #109 886.
5. Xenopus Extract Isolation Medium without DTT (DTT added to XEIM less than 24 hours, most preferably less than 1 hour prior to using for the permeabilized sperm pretreatment before adding the sperm to the frog egg extract). 1.5 mM $MgCl_2$, 100 mM KCl, and 10 mM Tris-HCl, pH 7.5.
6. Dithiothreitol, DTT, also called Cleland's Reagent, from Calbiochem, 233155.

For Cytopreps
1. Glass Slides.
2. Filter Cards, Shandon Inc., SCA-0005.
3. Giemsa Blood Staining Solution, Baker (#M708-01)

For Autoradiography
1. Kodak NTB2 autoradiography emulsion, International Biotechnologies, Inc. (IBI), #165443.
2. Kodak developer D-19, Cat 146-4593.
3. Kodak fixer, Cat 197-1746.

Frog Egg Extract

*Xenopus laevis* egg extract may be prepared as described in Example 1. The frog extract may be included as part of the diagnostic kit where the diagnostic kit is used within 1 to 2 days of the date on which the egg extract was prepared. Alternatively, the *Xenopus laevis* frog egg extract will be prepared fresh on the date of assay, and not transmitted as part of the kit itself, or frozen egg extract (frozen in liquid nitrogen) may be shipped with the kit or as a separate component. The frozen extract may alternatively be provided on dry ice. For example, the extract may be packed in dry ice within a container, and said container packed within second boxing of dry ice for shipping. Either a detailed printed description of the protocol for preparing the extract will be provided in the assay kit, or the clinician/physician may obtain a fresh or frozen preparation of the frog egg extract. Other types of egg extract, such as *Rana pipiens* frog egg and others, may also be used as part of the kit.

The egg extract may also include one or more protease inhibitors, such as leupeptin, PMSF, soybean trypsin inhibitor, and the like, to further improve the stability of the extracts activity when shipped as fresh, non-frozen form, or on dry ice.

A cytocentrifuge, table top centrifuge and a light microscope equipped with phase contrast objectives will be required as standard laboratory or clinic equipment in order to conduct the sperm fertility assay. The sperm fertility assay most preferable will be conducted under Biosafety Level 2 conditions as is standard for the analysis of human tissues and body fluids.

The kit may contain, alternatively, an empty container sufficiently large to hold a volume of about 2 mls. semen. These smaller containers are particularly suitable for small volumes of sperm, such as that typically obtainable from oligozoospermic human males.

EXAMPLE 8

Method for Screening Prospective Sperm Donors for In Vitro Human Fertilization

The present example is provided to outline a method for use in screening human male sperm samples as prospective sperm donors for the in vitro fertilization of human females.

All human samples must be handled according to those laboratory criteria known to those in the art as "Biosafety level 2." Possible test sample and control sample contamination of laboratory personnel with, for example, hepatitis and human immunodeficiency virus will thus be avoided. All samples should be screened for HIV prior to use in an in vitro fertilization attempt, and the sample discarded even if it is demonstrated to have potential human egg fertilizing capacity.

For the described method, a semen sample from a prospective human sperm donor, or from a "panel" (more than one) of prospective human sperm donors, will be obtained and washed to isolate test sperm samples. A control sperm sample will also be prepared from a semen sample obtained from a human male who is of "proven" fertility (sired one or more children). A number of sperm from the test sperm sample(s) and an equal number of the control sperm sample will then be permeabilized in a medium containing lysolecithin and soybean trypsin inhibitor, most preferably at a concentration of about 0.05% lysolecithin and 1 μg/ml soybean trypsin inhibitor in an NIM medium. The permeabilized test and control sperm sample will then be reduced in a medium containing dithiothreitol (DTT), most preferably at a concentration of 50 mM DTT as part of the XEIM medium described in Example 1.

The reduced test sperm sample(s) and control sperm sample in equal number are then to be incubated in a volume of egg extract containing a detectable labeling compound, such as $^3$H-TTP, for about 2 hours at 19° C. Most particularly, the concentration of $^3$H-TTP is about 80 μCi/ml.

After incubation in the detectable labeling compound, a number of the sperm in the test sperm sample(s) and an equal number of the sperm in the control sperm sample are to be incubated in a volume of *Xenopus laevis* frog egg extract (egg extract defined in Example 1). The sperm activation events of sperm chromatin decondensation, sperm chromatin recondensation and DNA synthesis are then to be monitored in all samples for at least an incubation period of about 3 hours.

A prospective human sperm donor for in vitro fertilization of a human egg will be identified in donors whose sperm samples do not demonstrate any abnormality in sperm decondensation, DNA synthesis and sperm recondensation, as compared to the control human sperm sample. A test sperm sample should demonstrate at least 80% the sperm decondensation of a control sample.

Cytoprep analysis of a small volume of sperm incubate from test samples and control samples may be performed to confirm acceptable sperm decondensation rates, DNA synthesis and sperm recondensation rates employing a 15 minute, 2 hour and 3 hour sperm aliquot from the respective incubates.

The method for screening prospective human sperm donors may be used on a large scale inexpensively and using only a small volume of the patient obtained sample, and would be relatively inexpensive and rapid as part of a battery of standard clinical sperm screening routine.

EXAMPLE 9

Comparison of Assay Results for Sperm Decondensation of Infertile Human Male Sperm and Fertile Human Male Sperm in HSAA The following protocol for conducting the HSAA assay, (i.e., assessing chromatin decondensation, DNA syntheses and chromatin recondensation) is used as a preferred technique to the one outlined in Example 3. 59 patients were analyzed according to the following technique. The main difference with the technique described in Example 3 is that in evaluating sperm decondensation, only one calculated percentage value of the control value for decondensation for each patient is used, rather than multiple control calculations at the 5 minute and 10 minute time points, as described in example 3. The same abnormal responders in the HSAA were detected with either approach. The improvement in the presently outlined protocol is that only one measurement of the percent (%) decondensed sperm per patient is required, cutting in half the microscopy time required to perform the assay. The cumulative data from that patient is plotted at FIGS. 9A–9B.

MATERIALS AND METHODS

1. Control Assay Mix (CAM) will be prepared by adding 8 $\mu$l of sperm suspension from the fertile male (200,000 sperm) to 100 $\mu$l of extract containing 8 $\mu$Ci of TTP (8 $\mu$l) having a final volume of 116 $\mu$l. Phase contrast microscopy will be used to observe wet mounts prepared by placing 5 $\mu$l aliquots of the CAM on glass slides onto which a coverslip will be applied. The percentage of nuclei that are fully decondensed at 5, 10 and 15 minute time intervals after the addition of the sperm to the extract will be determined (about 50 nuclei per time point), and determine the time point where >90% of the sperm have fully decondensed. Any extract preparation that does not induce >90% of the control sperm into the fully decondensed state after a 15 minute incubation in the extract will not be used for the analysis of patient samples.

2. The Sperm Assay Mix (SAM) for the patient will be prepared as described for the Control Assay Mix (CAM). At the point at which greater than 90% of the sperm in the CAM are found to be fully decondensed, 5 $\mu$l of SAM will be removed for use in preparing a wet mount. Again, about 50 nuclei will be scored for decondensation and the % of fully decondensed nuclei will be determined. The SAM % decondensation will then be compared with the CAM % decondensation results and the % of the control that have fully decondensed will be determined. Examples of what would be scored as fully decondensed sperm as shown in FIGS. 7A–7E.

3. After a 20 minute incubation of the sperm in the extract, 25 $\mu$l of suspension will be removed and mixed with 75 $\mu$l of PBS (Phosphate Buffered Saline). Two cytoprep slides will then be made, putting 50 $\mu$l of specimen-PBS mix into each cytocentrifuge chamber. The specimen will then be centrifuged at about 2,000 rpm in a Shandon Cytocentrifuge for 3 minutes selecting the high acceleration setting. Any sperm that have not decondensed will not smear onto the glass slide (See FIG. 4B). The cytoprep slides will be fixed for 5 minutes in 1:3 Glacial Acetic Acid-Methanol and then Giemsa stained. The 20 minute Giemsa stained cytopreps will be used to further verify abnormal decondensation in that such SAM cytopreps will have less smearing than control cytopreps.

4. At 2 hours, the assay mixture was mixed and 25 $\mu$l of the suspension removed to mix with 75 $\mu$l of PBS. Cytopreps were prepared using 50 $\mu$l of specimen-PBS mix/slide in a centrifuge at 1500 rpm for five minutes selecting the medium acceleration setting (Shandon Cytospin III® centrifuge). The cytoprep slides will be fixed for 5 minutes as in #3. The fixed cytopreps will then be dipped in Kodak nuclear track emulsion (NTB-2), (an autoradiography emulsion) stored at 4° C. for two weeks, and then following development, be Giemsa stained through the emulsion. All microscopy will be done using a Leitz Orthoplan microscope (i.e., a standard light microscope set up for phase contrast microscopy with a 25x phase contrast lens, suitable for scoring decondensed and recondensed sperm nuclei and an oil emulsion objective for scoring labeled nuclei). For both the CAM and SAM slides, 200 nuclei will be scored for labelling and the results with CAM (% of the nuclei showing a label above background) compared to those with the patient's sperm to determine the % of Control being labelled.

5. At 3 hours, the suspension will be mixed and 25 $\mu$l of the suspension will be removed and mixed with 75 $\mu$l of PBS. Two cytopreps using 50 $\mu$l of specimen-PBS mix will then be made. These cytropreps will then be centrifuged at 1500 rpm for five minutes with medium acceleration. A 5 $\mu$l, aliquot of the sample will also be removed for use in making a wet mount slide and, again using phase contrast microscopy, the % recondensed nuclei for both CAM and SAM will be determined, as well as a determination of the % of the Control that have recondensed. The 3 hour Giemsa stained cytopreps will be used to verify that recondensation of the chromatin was the same in the CAM and SAM cytopreps.

HSAA Normal/Abnormal Response Values

A normal response is any value greater than or equal to 80%, preferably at least 90%, of the normal control value for decondensation, recondensation and/or DNA synthesis. An abnormal response is any value less than 80% of the normal control value for decondensation, recondensation and/or DNA synthesis.

Patient #22 was an unexplained infertile male that had been screened as infertile according to the criteria outlined herein. The results obtained in the HSAA sperm chromatin decondensation for patient #22 sperm is provided at FIGS. 7B–7D. The control sperm from a fertile male is provided at FIGS. 7A and 7E.

Figure 6A:
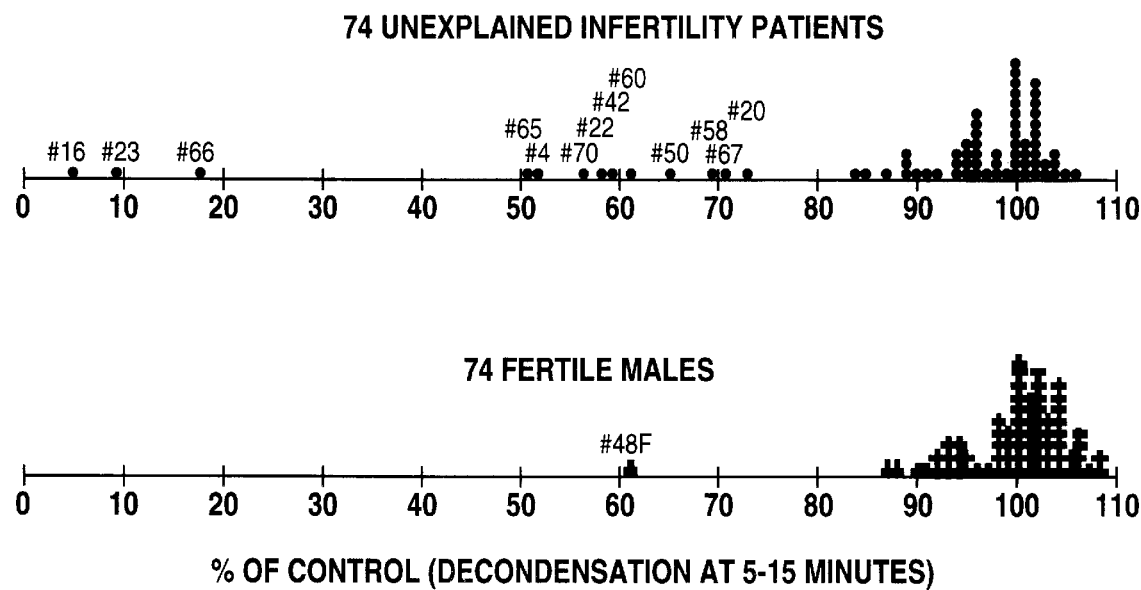
FIGS. 6A and 6B provide a scatterplot of data collected from 74 known fertile and 74 unexplained infertile human males. Sperm chromatin decondensation (FIG. 6A) and DNA synthesis (FIG. 6B) data are provided for each of the groups.
Figure 6B:
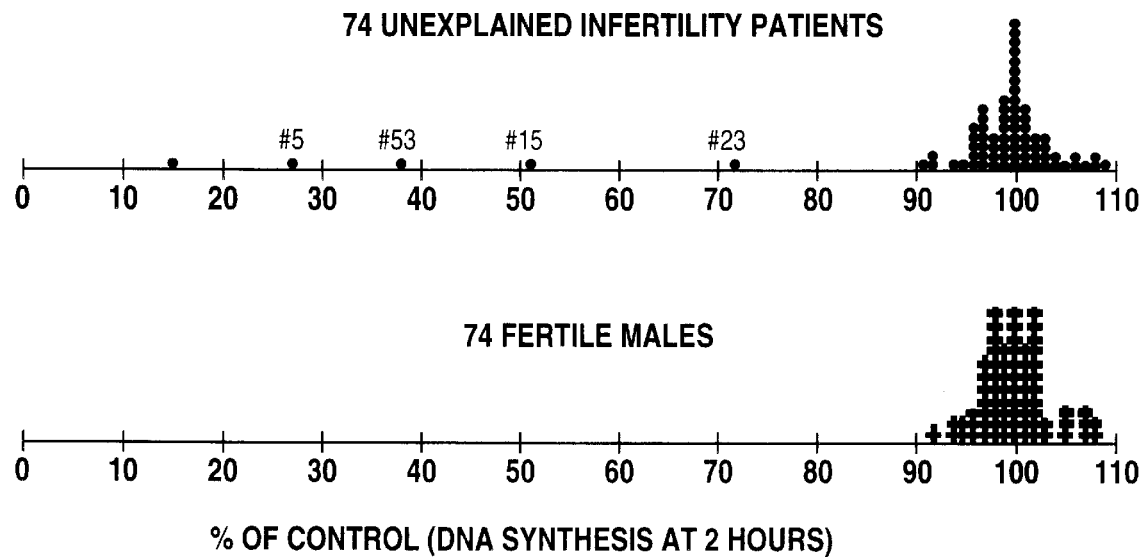
Figure 7A:
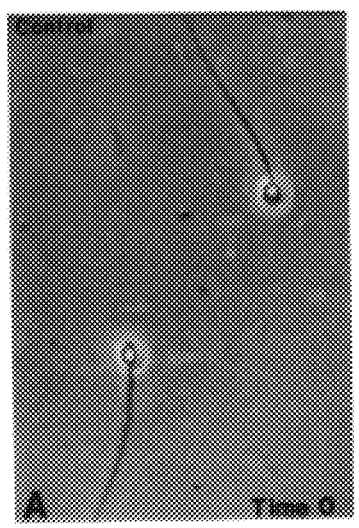
FIGS. 7A–7E provide micrographs taken from a human sperm sample of human patient #22, diagnosed with unexplained infertility (FIGS. 7B, 7C and 7D), and from a fertile male (FIGS. 7A and 7B). Patient #22 had an HSAA decondensation score that was 57% of the control, i.e., an abnormal response.
Figure 7B:
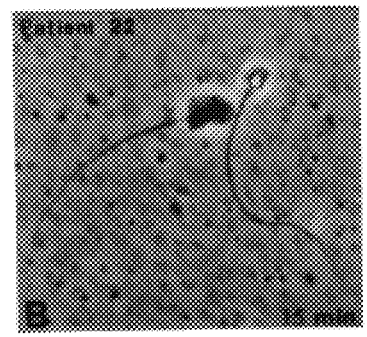
Figure 7C:
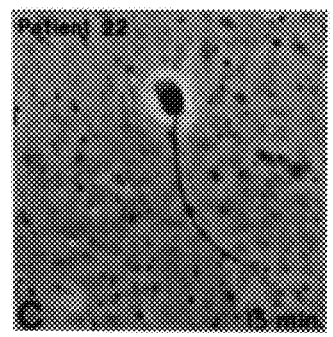
Figure 7D:
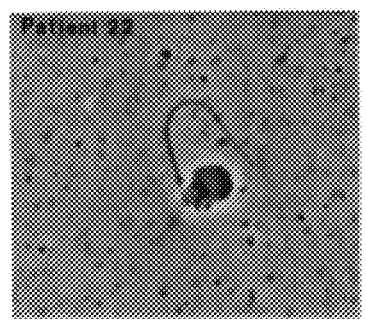
Figure 7E:
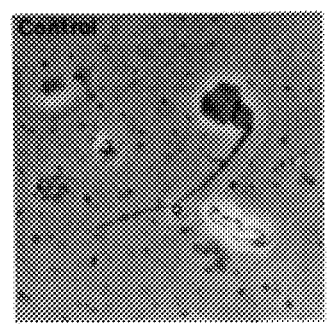
Figure 8A:
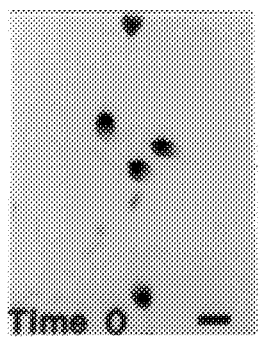
FIGS. 8A–8J. A pictorial representation of a normal response of permeabilized human sperm incubated in frog egg extract during a 3 hour time course. The sperm nuclei shown in 8A–8H were photographed using a 40X objective. Panels 8I and 8J were photographed using a 25X objective in order to include more sperm nuclei in the field of view. Bar=10 μm. Bright field microscopy was used to photograph Giemsa-stained cytopreps of nuclei shown in 8A–8D, while 8E–8H are nuclei photographed using phase contrast microscopy, and C shows autoradiographs of Giemsa-stained nuclei. (8A,8E,8I) Time Zero. Permeabilized sperm with no extract treatment. (8B,8F,8J) 15 minutes in egg extract. Panel B shows sperm nuclei that did not remain intact during the centrifugation procedure used when making cytopreps; the nuclei became smeared onto the glass slide. After 5–15 minutes in the frog egg extract, >95% of the sperm have completely decondensed nuclei. A typical completely decondensed sperm nucleus is shown in 8F; all nuclei shown in J are fully decondensed. 8C, 8G 2 hours in egg extract. The sperm nuclei have begun to recondense their chromatin. Notice the decreased size of the sperm nucleus in 8F compared to that in 8G. Recondensed sperm nuclei again withstand the cytocentrifugation procedure (note intact nuclei in 8C). The labelling of the nuclei in 8C (black grains over the nuclei) indicates that they have undergone DNA synthesis. Typically, >95% of control nuclei are labelled after 2 hours in frog egg extract containing tritiated thymidine. 8D, 8H 3 hours in egg extract. Examples of recondensed nuclei are shown in 8D and 8H. In 8D are shown nuclei that have recondensed their chromatin to the late G2 to early prophase chromosome level. Ten photographs of permeabilized sperm, decondensed sperm nuclei at the 15 minute time point and recondensed sperm nuclei at the 3 hour time point were cut out and weighed separately using an analytical balance. The average weight of the nondecondensed cut-outs was 0.0015 g±0.0002 g; of the fully decondensed cut-outs, 0.010016 g±0.0006 g; and of the fully recondensed cut-outs, 0.00296 g±0.0002 g. These values translate to a 7-fold increase in size as sperm decondense, and a 3-fold decrease in size as they recondense. The recondensed chromatin in the nucleus shown in 8H is no longer contained within a nuclear membrane, as the periphery of the nucleus is rough and appears to be delineated by recondensed chromatin. The outline of the nucleus is smooth when the nuclear membrane is intact (8F and 8G).
Figure 8B:
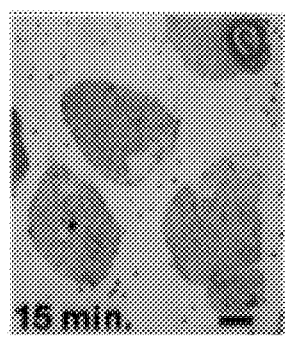
Figure 8C:
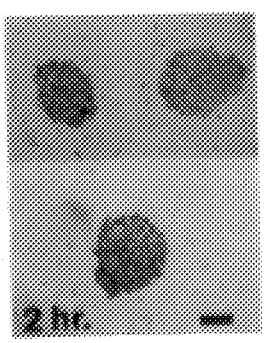
Figure 8D:
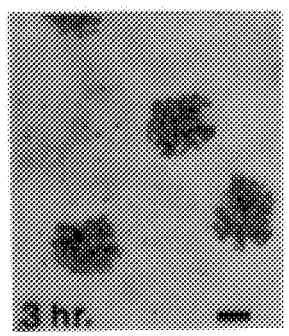
Figure 8E:
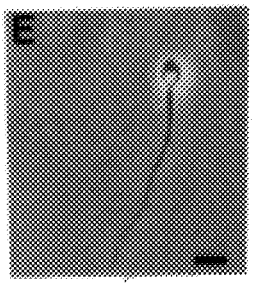
Figure 8F:
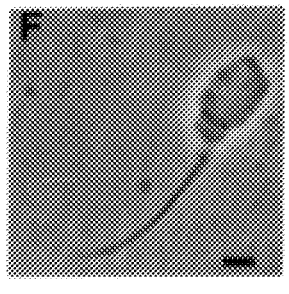
Figure 8G:
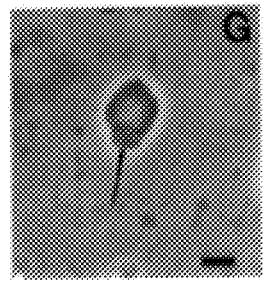
Figure 8H:
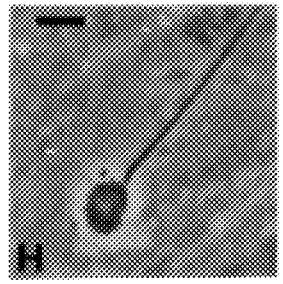
Figure 8I:
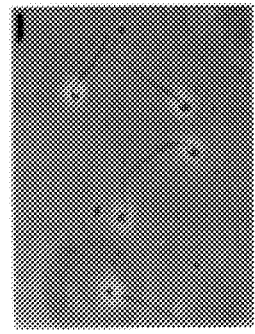
Figure 8J:
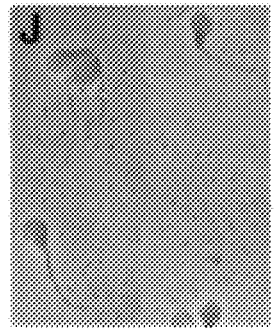

After 15 minutes of incubation in the egg extract, Patient #22 had a HSAA Decondensation score that was 57% of the control, i.e., an abnormal response. In FIG. 7B is shown an example of a sperm that did not decondense alongside a partially decondensed sperm. Another partially decondensed sperm is shown in FIG. 7C. Fully decondensed sperm are shown in FIGS. 7D and 7E. From here to the end of the assay, the CAM and SAM will be treated as follows:

It was found that of the 74 patients analyzed using the HSAA (See FIG. 6A–6B; combined data of examples 3 and 4 (N=15) and Example 9 (N=59)), 16 (21.6%) of the males from inexplicably infertile couples produced sperm that responded abnormally in the assay (95% confidence interval of 13.2%–33%), while sperm samples from a control group of 74 fertile males showed only 1 (1.4%) abnormal response (95% confidence interval of 0%–8.3%). (See FIG. 6.) The percentage of abnormal responders in the unexplained infertility patient group was significantly higher than that found for the fertile male group (p=0.001, Chi-Square Test). The HSAA is thus established as a useful tool for diagnosing a subgroup of human male infertility patients.

EXAMPLE 10

Sperm Decondensation and Human Male Infertility

In FIGS. 6A and 6B are shown the combined data from the study described at example 3 and Example 9, above. It was found that 16 of the 74 inexplicably infertile patients analyzed to date produce sperm that respond abnormally in the assay, while sperm samples from a control group of 74 fertile males showed only 1 abnormal response (p=0.001).

STATISTICAL ANALYSIS

Chi Square analysis was used to calculate p values. The 95% confidence interval of the true percentage of inexplicably infertile males diagnosed by the HSAA (13.2%–33%) was determined as described by Fleiss.[43] In the studies described herein, any response less than 80% of the control in either chromatin decondensation, DNA synthesis or chromatin recondensation is considered to be an abnormal response in the HSAA. Gaussian distribution approximation was used to determine the probability of a sperm sample from a normal individual having a human sperm activation assay (HSAA) response of less than about 80% of the control (p<0.00001).

RESULTS

The decondensation data collected from the 74 unexplained human patients reveals that a significant number of the samples demonstrated less than about 85% or about 90% decondensation at 5–15 minutes, while only 1 of the known fertile males demonstrated less than 90% (i.e., 62%) of control decondensation at 5–15 minutes (See FIG. 6A). The data in FIG. 6B illustrates that all 74 fertile men demonstrated 90% of the control or greater DNA synthesis at 2 hours, while 6% of the infertile males tested demonstrated less than 75% of the control DNA synthesis at 2 hours.

The recondensation data was not plotted, as no patients have been found to have sperm that recondense abnormally in the HSAA (less than 80% of the control).

Using this data, abnormal responses in the HSAA are divided into three categories.

Category 1: abnormally low number of decondensed sperm nuclei/normal DNA synthesis (Patient #'s 4,22, 35,36,47,51,55,63,65,70 and 71);

Category 2: abnormally low number of decondensed sperm nuclei/abnormally low number of sperm nuclei synthesizing DNA (Patient #'s 15 and 23); and Category 3: normal decondensation/abnormally low number of sperm synthesizing DNA (patient #'s 6,40 and 58).

It is clear from the graph shown in FIG. 6A and 6B, that by drawing the line for abnormal response in the HSAA at values less than 80%, only those patients with a dramatic negative response in the HSAA are included. No false positive result has been observed in the assay (a patient sample used for IUI, IVF-ET or GIFT and the HSAA, responding abnormally in the HSAA but resulting in a successful pregnancy).

Figure 9A:
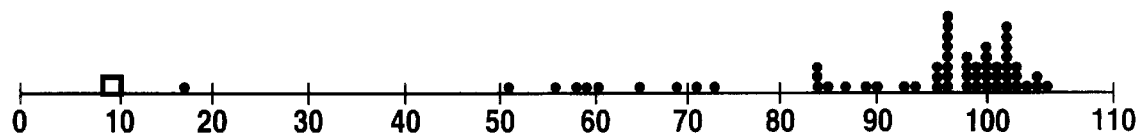
FIGS. 9A and 9B. Scatter plots of responses of sperm from 59 inexplicably infertile and 59 fertile males in the HSAA for (9A) decondensation, and (9B) DNA synthesis. The open box denotes the patient who had both abnormal decondensation and abnormal DNA synthesis responses in the HSAA. Of the 59 males having unexplained infertility (UI) whose sperm were analyzed in the HSAA, 13 had abnormal responses that were <80% of the control.
Figure 9A:
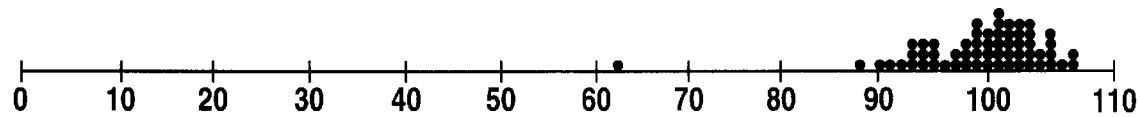
Figure 9B:
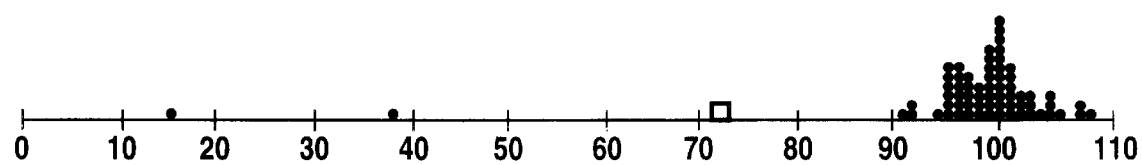
Figure 9B:
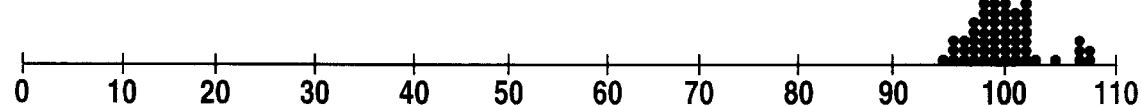

FIGS. 9A–9B shows the decondensation and DNA synthesis results expressed as the percent of control values. The distribution of the decondensation and DNA synthesis response of the 59 fertile males had the two responses clustered in the range of 85% to 110% (except for one male) and 90% to 110%, respectively. By contrast, the distribution of decondensation responses of the idiopathic infertile males showed two different populations: one clustered in the range of 84% to 107%, another with a range of 9% to 73%. The distribution of DNA synthesis also showed two different populations: one clustered in the range of 90% to 110%, the other in the range of 15% to 72%. Abnormal and normal populations have been defined as <80% and >80%, respectively, based on the wide gap observed near the 80% value, separating the patients (but not the fertile controls) into two groups (FIG. 4). This biphasic distribution was observed for both decondensation at 5–15 minutes and DNA synthesis at 2 hours (FIGS. 4A–4F). Also, there was a low probability that sperm from a normal individual would respond with a value of <80% of the control when analyzed in the human sperm activation assay. Of the 59 fertile males whose sperm samples were analyzed in the human sperm activation assay in this study, the percent of the control values for decondensation and DNA synthesis were distributed around a mean ±4.69% and 3.06%, respectively. Based on these data, the probability of sperm from a normal individual having a human sperm activation assay response of <80% of the control was <0.000001 (Gaussian distribution approximation) for both decondensation and DNA synthesis. For these reasons, any sperm samples having human sperm activation assay response values <80% of the control were considered abnormal. Significant differences were not observed in the recondensation of sperm from the idiopathic infertile and fertile males.

EXAMPLE 11

Comparison of HSAA and SPA Results

Several tests are presently available to diagnose male infertility; these assay sperm number, morphology, motility, and the ability to fuse with and then enter a zona-free hamster egg as occurs during the SPA. None of the standard procedures, with the exception of the SPA, test the activation of the sperm nucleus after entry into the fertilized egg. The SPA score is determined by the percentage of eggs that are penetrated by the sperm, as determined by counting the eggs that contain decondensed or activated sperm nuclei. However, one cannot use the SPA to study the efficiency of the decondensation process.

During the SPA, the hamster egg routinely becomes bound with a large number of sperm that do not enter the egg and thus do not decondense. One cannot tell a nondecondensed sperm that is bound to the egg from a sperm that has entered the egg and not decondensed as a result of not responding to the egg activation signals. Interestingly, a zero SPA score may in some cases reflect the sperm's inability to decondense instead of its penetration capabilities as is presently assumed. As for using fertilized hamster eggs to follow DNA synthesis and recondensation, the labor and expense that would be required to obtain enough eggs to analyze one patient would prohibit using the SPA to study sperm activation as a routine clinical procedure. Conversely, the HSAA allows for routine comparison of hundreds of a patient's activated sperm nuclei with those from a normal, fertile male, and easily detects any abnormal response. The HSAA is thus the assay of choice for sperm activation analysis.

Eight of the 16 abnormal responders detected using the HSAA were also evaluated using the SPA. Five of the patients had penetration scores of less than 10% (all 0%), and 3 had scores greater than 10% (a score of less than or equal to 10% is considered abnormal) in the SPA.

SPA results were obtained from 24 of the 58 unexplained infertility patients whose sperm responded normally in the HSAA. Nine of the 24 samples assayed had abnormal SPA scores of less than 10% (three 0% scores). In a study analyzing the sperm samples from 443 men having 0% SPA scores, and 0–3 abnormal sperm parameters, 16.3% of these males had no readily detectable sperm abnormalities, i.e., unexplained infertility.[72] The 0% SPA scores may be a result of the sperm not penetrating the egg, not decondensing in the penetrated egg, or a combination of both.

EXAMPLE 12

Advancing Age and Sperm Efficacy of Fertilization Using HSAA

Age-related male infertility problems generally begin at around 60 years of age when testosterone, dihydrotestosterone receptor and semen fructose levels decrease, and sperm motility and normal sperm morphology scores are declining[77,78]. The present HSAA assay may be used to determine if a correlation exists between age and infertility as a measure of abnormal response in the HSAA assay, as well as a specific method for screening human males of advancing age for abnormal sperm as a cause of infertility. As used in the description of the invention, the term advancing age is defined as at least about 50 years of age, or most particularly between 55 to 70 years of age.

The average age of both the fertile and inexplicably infertile males in the present study was 34 with a range of 22–52 years and 23–50 years, respectively. The average age of the abnormal responders was 34.1. Further statistical analysis of the data demonstrated that there was not a correlation between age and abnormal sperm nuclear decondensation ($r=0.11$, $p=0.34$) or DNA synthesis ($r=0.03$, $p=0.76$).

A correlation of abnormal responses in the HSAA with advancing age was not expected because the sample population examined did not include any males older than 52 years of age. It is anticipated that any age-related changes in fertility will be detectable by comparison of relative sperm decondensation of a patient sperm sample and/or DNA synthesis of sperm samples from fertile males 20 to 50 years of age and fertile males 50 to 70 years of age (fertility defined as having fathered offspring).

EXAMPLE 13

Sperm Efficacy and HSAA

The present example is provided to demonstrate the utility of the presently described methods for screening human sperm samples for changes in fertilizing capacity of a particular patient over time using the HSAA. It has been found that changes in a patient's fertilization efficacy over time may be detected using the HSAA as a function of an analysis of sperm activation events.

Two of the patients producing sperm that initially responded abnormally in the HSAA have, at later times, provided a different ejaculate that responded normally in the HSAA. This change in response detected with the HSAA assay is correlated with a change in the fertilization efficacy of the patient, as sperm obtained from these patients responded normally in the HSAA, and resulted in pregnancies when the remaining portions of their sperm samples were used in assisted reproductive technology attempts.

CLINICAL DATA

Patient #4 provided a sample 4 months after the initial HSAA test date that responded normally in the HSAA (52% of the Control Decondensation Score in initial assay, 100% of the Control in later assay). This sample resulted in a pregnancy when used in the IVF-ET procedure; however, the pregnancy ended with a spontaneous miscarriage at six weeks of pregnancy (See Example 4).

Patient #66 provided a sample 18 days after the initial HSAA test date that responded normally in the HSAA (17% of the Control Decondensation Score in initial assay, SPA score of 0%; 111% of the Control in later assay, SPA score of 11%). This sample resulted in a pregnancy when used in the GIFT procedure and the pregnancy went the full term, with the woman delivering a normal child.

Repeat samples were obtained from 7 of the patients whose sperm initially responded abnormally in the HSAA. Except for the 2 previously discussed patients #4 and #66, their sperm again responded abnormally. Sperm from these patients continued to be incapable of producing a pregnancy. Samples from 15 fertile patients whose sperm initially responded normally in the HSAA were also obtained. All these repeat samples again responded normally in the HSAA.

To date, only one false negative (a "fertile" male ((sired one child)) with an abnormal HSAA score) assay result has been observed. A repeat sperm sample was obtained from the patient that again responded abnormally in the HSAA. This male had only one child that was thirteen years old at the time of the HSAA testing; for the preceding 12 years this man has worked on several chemical spill clean-ups during which he has had potential exposure to toxic agents known to affect male fertility adversely. This particular male may no longer be a fertile male.

At present, no false positive results have been observed (when the same patient's sample was used for IUI, IVF-ET or GIFT and the HSAA, responding abnormally in the HSAA but resulting in a successful pregnancy). Note that 2 of the 16 patients with abnormal HSAA response did later produce normally responding sperm that proved fertile in assisted reproductive technologies.

These data illustrate that the HSAA can be used to determine a sperm sample's efficacy for fertilization.

EXAMPLE 14

Reproducibility of the HSAA with Frozen Semen Samples

The present example is provided to demonstrate the reproducibility of the presently described methods in testing human sperm samples that have been frozen prior to assay in the HSAA.

Non-permeabilized sperm samples from sperm specimens having more than 20 million sperm were stored frozen. These samples were collected as a portion of a sample not used in assisted reproductive technologies and/or the SPA analysis as part of a clinical regimen for fertility screening for repeat assays in the HSAA.

Using thawed sperm (that is, permeabilized after thawing), the HSAA analysis was repeated with 7 of the patient sperm samples that in the initial HSAA responded abnormally (Patent # 29, 42, 53, 58, 60, 65, 70). All 7 samples again responded abnormally in the HSAA. Six patients demonstrated reduced chromatin decondensation while 1 sample demonstrated reduced DNA synthesis. The HSAA analysis of 5 patient sperm samples that in the initial HSAA responded normally were also repeated from frozen permeabilized sperm samples. All 4 samples again responded normally in the HSAA.

EXAMPLE 15

Analysis of Varicocele Patients' Semen Samples in the HSAA

The present example is provided to illustrate the utility of the present invention for analyzing sperm from varicocele infertile males to identify potential candidates for varicocelectomy, as well as a screening method to identify patients for which varicocelectomy is a treatment of the patient's infertility.

Some varicocele males may be infertile because their sperm cannot activate properly once inside of the egg, and that in order for these males to become fertile, they must undergo a varicocelectomy. The present techniques may be used to screen human males for the need for this surgical procedure as part of a regimen for treating a couple's infertility.

The sperm samples from 3 males with palpable varicoceles and sperm counts of 2 million/ml (Patient A), 28 million/ml (Patient B) and 3.2 million/ml (Patient C) were analyzed in the HSAA as described in Example 9. They had SPA and HSAA (Decondensation) scores of 8%, 0% and 0%, and 85.1%, 73% and 10%, respectively. Patient B opted for a varicocelectomy. Ten months after the surgery, the patient provided a sperm sample that had SPA and HSAA (Decondensation) scores of 7% and 82.6% respectively. This sample resulted in a pregnancy when used in the GIFT procedure.

Grade II to Grade III varicocele males, as these terms are described in Steeno et al. (1976)(Andrologia, 8:47), which reference is specifically incorporated herein by reference, will be examined using the HSAA as described in Example 9.

Males with Grade II and III varicocele have a 62% overall success rate when treated for their condition, unlike the low 0–12% success rate seen for Grade I varicocele males (60). Therefore, while males with any of the three forms of varicocele may be screened according to the present methods, it is anticipated that the assay will be most particularly indicated for the screening of patients with Type II and III varicocele. The lower limit of sperm concentration to perform HSAA is being explored; samples containing at least about 400,000 sperm may be examined in the HSAA at present.

Upon determination of lowest values for number of sperm needed, semen samples from varicocele males will be analyzed in the HSAA and SPA. These males will be Grade II to III with motile sperm counts of 400,000 million or more. A number of the varicocele patients that have undergone unsuccessful ART attempt at pregnancy will undergo a high ligation varicocelectomy. Patients will be monitored for 6 months following their surgery for pregnancies by coitus. Semen samples from such individuals will be analyzed in both the SPA and the HSAA. For those patients who do not have coitus that results in pregnancy, another sperm sample will be obtained 6 months after their surgery for use in the SPA and HSAA.

EXAMPLE 16

Automated Semen Analytical Technique for Monitoring Sperm Activation Events

The present example outlines an automated approach to analysis of the sperm activation events as it relates to the screening and assessment of human sperm, such as in the analysis of causes of male infertility and presence of sperm abnormalities as described in the present invention.

Strategy 1

The sperm from 100 unexplained infertile males will be analyzed in the HSAA as described in Example 9. When an aliquot is taken from the assay mixture to be manually scored for decondensation or recondensation, an additional 6 $\mu$l aliquot will be taken and placed on a cell view slide that will be placed in the semen analyzer. The 'SORT' function (programmed to determine the head size of 125 sperm nuclei in approximately 5 minutes, values given as $\mu m^2$) will be activated.

When scoring decondensation, the analyzer will be programmed to determine the % of sperm that have not decondensed, have partially decondensed (between 25–50%) and have fully decondensed all based on measured sperm head size. For recondensation, the % of sperm that have not recondensed, have partially recondensed (between 25–50%) and have fully recondensed (based on measured head size) will be determined. The values will then be compared with the values obtained with a fertile male's sperm. Any patient having values less than 80% of the control will be considered abnormal responders.

The Hamilton-Thorne semen analyzer HTM-IVOS, is one particular automated device that is expected to be useful for this analysis. However, other machinery is expected to be equally as useful in the practice of the invention. Software available from Hamilton-Thorne Research (Beverly, Mass. 01915), known as Hamilton-Thorne Semen Analyzer Software, will be used in the automated application of the present methods.

Ten separate nondecondensed, decondensed and recondensed nuclei (30 total) were photographed and printed at the same magnification and then were weighed, each sperm individually. The sperm head dramatically increased in size as it decondensed and recondensed (see FIGS. 1A–1D). The average weight of the nondecondensed cut-outs (FIG. 1A) was 0.0015 g±0.0002 g, the fully decondensed cut-outs (FIG. 1B) was 0.010016 g±0.0006 g, and the fully recondensed cut-outs being 0.00296 g±0.0002 g. This translates to a 7 fold increase in size as the sperm decondenses and a 3 fold decrease in size as it recondenses.

Less than 2-fold increases may be detected using available instrumentation. Therefore, the dramatic changes observed according to the present techniques allow monitoring of the sperm activation events of sperm decondensation and recondensation in real time the kinetics (FIGS. 1A–1D).

Statistical Analysis

Responses as measured by the semen analyzer will be expressed in dichotomy (e.g., normal or abnormal). Agreement between both approaches in the dichotomous responses will be assessed using kappa statistical analysis (Fleiss, J. L. (1981), Statistical Methods for Rates and Proportions, 2nd ed., N.Y., John Wiley and Sons, Inc., pp. 13–15). A 100% agreement is expected, i.e., kappa=1.0. Meanwhile, if the agreements are completely independent of each other, then kappa=0.00.

In the case of the varicocele samples, which are expected to have low sperm counts, all of the sperm will be permeabilized, and in order to have a comparable control, an equal number of the normal control sperm from a fertile male will also be permeabilized.

Strategy 2

Permeabilized sperm from a normal fertile male will be used as control. Permeabilized sperm treated with ethylene glycolbis (sulfosuccinimidylsuccinate), a homobifunctional cross-linker that inhibits decondensation to levels as low as 20% of the control, will also be prepared. The sperm will be kept on ice during transport to the testing laboratory. After addition of control and chemically treated sperm to the egg extract, 6 $\mu$l aliquots will be removed at 5 minute intervals for 30 minutes for analysis manually scoring the decondensed sperm nuclei using a phase contrast microscope. After 3 hours, aliquots will be taken and sperm nuclei scored for recondensation. The % of the Control decondensation and recondensation values that will be 20–30% and 100% of the Control based on previous studies will be determined (28). The study will then be repeated, this time taking 6 $\mu$l aliquots that will be placed on a cell view slide that will be placed in the semen analyzer. The 'SORT' function (programmed to determine the head size of 125 sperm nuclei in ~5 minutes, values given as $\mu m^2$) will be activated. When scoring decondensation, the analyzer will be programmed to determine the % of sperm that have not recondensed, have partially recondensed (between 22–50%) and have fully recondensed (based on measured head size). The % of Control decondensation and recondensation values will be determined. These results will then be correlated with those from manually scoring the sperm nuclei.

Strategy 3

The Hamilton Thorn Semen Nalyzer HTM-IVOS, also has an integrated fluorescent illumination system that provides us with an alternative way to measure the decondensation and recondensation. It will be determined if sperm in 6 $\mu$l aliquots can be stained with Hoechst 33342. Then, using fluorescent strobe illumination, the increase in fluorescence associated with increased surface area of the decondensing sperm nuclei will be measured, and the decrease in fluorescence associated with the decreased surface area of the recondensing sperm nuclei measured. Again, the % of Control decondensation and recondensation values will be determined to discern if they reflect those from manually scoring the sperm nuclei.

EXAMPLE 17

Recondensation of Sperm in the HSAA using Automated Analysis

EXAMPLE

To date, no abnormal recondensation response in the HSAA has been detected in the 74 male patient sperm samples examined in the unexplained infertile males examined. Between 95–100% of all sperm nuclei examined to date, after a 3 hour incubation in the extract, have the recondensed appearance shown in FIG. 1D. However, by using the Semen Analyzer as described herein, subtle differences in recondensation will be detectable not consistently detectable by conventional microscopic analyses. Because of this, sperm nuclear recondensation may be an important distinguishing criteria in evaluating fertility upon the use of more sensitive analytical equipment. Chromatin recondensation will be a more significant diagnostic indicator of sperm (human) abnormalities where the sperm analyzer is employed in screening human sperm samples.

EXAMPLE 18

Protocol for Assisted Reproductive Technologies Use of Sperm Selected With HSAA

The present example is provided to demonstrate the utility of the present invention as part of a regimen for selecting human sperm samples for use in assisted reproductive technologies in pregnancy attempts, examples including IVF, GIFT and IUI procedures.

Methods

HSAA

The HSAA assay as described in Example 9 is to be conducted on all samples as part of the presently described screening procedure. To promote oocyte maturation, adult female *Xenopus laevis* frogs will be injected with 500 units of human chorionic gonadotropin in the afternoon/evening of the day preceding the experiment. Mature eggs will be collected and prepared as described in Example 3.

Sperm samples that demonstrate at least a score of 80% sperm decondensation, recondensation and DNA synthesis in the HSAA as defined herein are selected for use in the GIFT, IUI or IVF procedures. Since 99% of patients undergoing the GIFT procedure have extra eggs which may be fertilized in vitro and frozen, data on fertilization and cleavage rates on all GIFT patients may also be collected.

Hormonal Regimen for Female Patients

Women undergoing IVF/GIFT procedures are routinely started on GnRH analogue (Synarel nasal spray or Lupron subcutaneous injections) starting on 23 or 24th day of the cycle. When estradiol (E2) level is <60 pg/ml ovarian stimulation is initiated by injecting 225 IU of Metrodin for 2 days followed by 225 IU of Pergonal daily. An ultrasound scan and $E_2$ level is performed on the 5th day of injection. Higher doses are chosen if follicular sizes at this time are <1 cm. Daily $E_2$ levels and pelvic ultrasound examinations are continued until at least three follicles reached a diameter of 1.5 to 1.6 cm and 10,000 units of HCG was given IM that evening. Laparoscopy and GIFT procedure, or ultrasound aspiration is performed 35 hours later. Oocytes are identified by pouring the follicular fluid into Petri dishes and microscopic screening. After evaluation, the eggs are transferred into 2 ml of incubation medium (HAMS-F 10 with 15% maternal serum) in organ culture dishes. Cover and set in incubator until the time of insemination.

Sperm selected according to the criteria outlined herein that are obtained from the top layer of incubation medium after swim up procedure is used for insemination. About 200,000 motile sperm are added to each oocyte.

The occurrence of fertilization is examined 16–18 hours after insemination. If there are two pronuclei, the egg is transferred into a dish containing growth medium (HAMS F-10+20% MS). On the following day, about 40–44 hours post insemination, the embryos are examined for cleavage. Up to 4 embryos are transferred and the excess embryos are cryopreserved. The IVF program has a fertilization rate of 80% for mature oocytes and a 86% cleavage rate.

GIFT PROCEDURE

Semen samples meeting the criteria outlined herein in both HSAA and SPA, and prepared according to the swim-up technique (top layer sperm) is obtained 2–2.5 hours before aspiration of eggs. Three oocytes with 100,000 sperm per egg are loaded into the gamete transfer catheter and released into the ampullary portion of the tube through the laparoscope. The pregnancy rate observed using the GIFT procedure is 35%.

Modified HAMS F-10 medium is made up weekly. Each batch is tested with 2 cell mouse embryos and it is used only if it supports development of 85% of embryos to blastocyst over 72 hours. Throughout the culture, 15% of maternal serum (MS) is used as serum supplement. After fertilization, 20% maternal serum is used in the growth medium. Culture is carried out in a humidified atmosphere of 5% $CO_2$ in air.

IUI PROCEDURE Preparation of the sperm for intrauterine insemination using Swim up Technique A semen sample, obtained in a sterile container, is incubated at 37° for 30 minutes to allow the sample to liquify. About 3 ml of medium (HAMS F-10 with 10% MS or HSA) is added to sterile tubes containing 1 ml of semen. It is centrifuged at 500×g for 10 minutes; discard the supernatant and resuspend each pellet in 3 ml medium. It is again centrifuged at 500×g for 10 minutes and the supernatant discarded. One ml of medium is layered over the pellet and incubated at slant for 1 hour. The top layer is collected from all the tubes and used for intrauterine insemination.

Human Sperm Preparation

All semen donors will abstain from ejaculation for at least 2 days, preferably 2–4 days, prior to the collection of the semen sample by masturbation.

Semen samples from the varicocele and inexplicable infertile males used as part of a screening regimen will be the aliquot of the sample not used in IVF, the SPA and/or assisted reproductive technique elected. These samples will be kept in a 4° C. refrigerator for up to 7 days before parallel assays on samples collected throughout the week, or stored frozen. Fresh samples are not needed for the HSAA, as stored semen samples from a fertile male respond the same in the HSAA as do sperm collected from the same fertile male on the day the assay is performed, even after 4° C. storage of up to a month. A semen sample from a fertile male will be obtained once a week and stored in a 4° C. refrigerator (preferably no more than 4 weeks) until used in the HSAA.

On the day of the assay, the semen samples from the fertile male and the unexplained infertile male patients will be incubated for 30 minutes at 37° C. Each sample will then be suspended in 10 ml of nuclear isolation medium (NIM, 200 mM sucrose, 2.4 mM $MgCl_2$, 10 mM Tris-HCl and 5 mM maleic acid, pH 7.4). A sperm count will be taken and 20 million sperm allocated for use in the assay. The remainder of the sperm will be pelleted by centrifugation (10 minutes, 400 g) and resuspended in 0.5 ml of phosphate buffered saline (PBS) with 15% glycerol. The mixture will be frozen in a –20° C. freezer, then transferred into liquid nitrogen. These sperm can be thawed and analyzed again in the HSAA if a repeat of the assay is desired.

EXAMPLE 19

Protocol for Assisted Reproductive Technologies Use of Human Sperm Selected with Human Sperm Penetration Assay (SPA) and HSAA The present example outlines a screening regimen for human sperm that includes both the HSAA and the SPA.

HAMSTER OOCYTE PENETRATION TEST (SPA)

Female hamsters are injected with 30 IU PMS (Pregnant Mare's Serum), followed 48 hours later by 30 IU hCG (human Chorionic Gonadotropin). Sixteen to 18 hours after hCG injection, the hamsters are sacrificed by cervical dislocation or with ether under a fume hood. Using sterile instruments, each ovary with attached oviduct containing the distal portion of uterus is removed and placed in a sterile petri dish containing sterile mineral oil. Using a dissecting scope, the segment of oviduct containing oocytes is located and punctured with a pasteur pipette and oocytes retrieved into a drop of incubation medium. Oocytes from the medium are transferred into a drop of 0. 1% hyaluronidase and wait 3–5 minutes or until cumulus mass is digested. Oocytes are washed 5 times by transferring them from one drop of medium into another. Washed oocytes are placed in a drop of 0.1% trypsin for about 2 minutes or until zona-pellucida is digested. Oocytes are washed 5 times and then incubated with sperm.

About 1 million washed human sperm (swim up procedure) are placed with 25–30 oocytes in 200 ml. of medium, covered with sterile mineral oil and incubated at 37° C. in 5% CO2 for 4 hours. At the end of the incubation, oocytes are washed 5 times and placed on a slide containing a drop of 3% qluteraldehyde. Siliconetorease or petroleum jelly is applied to the edge of a glass cover slip and this is placed over the drop of glutaraldehyde. Slide is stained with aceto-lacmoid stain, and examined under microscope for sperm penetrated oocytes. A 100×phase contrast objective is used. Calculate percent penetrated and penetration index. (Penetration index=# of sperm on eggs/total # of eggs). A penetration of 10% or more is considered normal.

The HSAA sperm preparation, Hormonal regimen for females, GIFT, IUI and other assisted reproductive technologies will be conducted and described in example 18. Results achieved using sperm selected by screening by both HSAA and SPA are to be collected to determine a comparison of successful pregnancies when both screening protocols are used instead of an HSAA screen alone.

EXAMPLE 20

Image analysis system and the Flow cytometer Approaches in the Analysis of Sperm Activation Events in Assessing Male Infertility The most time-consuming aspect of the HSAA is assaying DNA synthesis by autoradiography. The autoradiographic approach requires a two week exposure of the labelled nuclei to the emulsion. An alternative approach that could be performed in one day would use a quantitative fluorescence microscopy.

The general technique of quantitative fluorescent microscopy is routinely applied to determining the amount of DNA in the nucleus of a cell (Rost, F. W. D. Quantitative Fluorescence Microscopy. Cambridge University Press, Cambridge, England (1991). The present example outlines the application of this general technique to the disclosed methods of fertility evaluation in the analysis of DNA synthesis.

The first consideration in using microfluorometry is the choice of fluorescent probe. Most fluorescent probes stain for total DNA (e.g.; 4',6-diamidine-2-henylindole, DAPI; propidium iodine, PI; Hoechst 33342). However, for the present application, the primary interest is in detecting newly synthesized DNA in the control sperm from a fertile male and comparing this amount of "normal" DNA synthesis to that of the unexplained infertility patients' sperm. Therefore, probes that stain total DNA will not be used in the present studies, as these probes would require that the newly synthesized DNA be detectable over the background of the basal sperm DNA. Instead, focus for the present uses will be in the use of halogenated nucleosides, such as bromodeoxyuridine (BrdUrd), to label newly synthesized DNA, followed by staining with Anti-BrdUrd monoclonal mouse IgG and rhodamine conjugated Goat anti-Mouse antibodies followed by quantitative fluorescence microscopy. Vanderlaan et al. (1986) (Cytometry, 7:499–507) provides a description of monoclonal antibodies that may be used for this purpose.

The second consideration is what image analysis system to use for the project, specifically what type of camera to use to collect the data for transfer to the computer containing the image analysis software. This choice is determined by the intensity of the fluorescent signal. The egg extract contains a large amount of thymidine that will compete with the BrdUrd for incorporation into the newly synthesized DNA. As the signal from the labelled nucleus is not expected to be as intense as if for example, total DNA with DAPI or PI were stained (that is an alternative approach, as outlined herein), the Peltier-Cooled video camera that can be used for capturing an image in both dim and bright light applications is most preferred. A Macintosh IIci computer that can be used with the Scion LG3 frame grabber and Macintosh computer compatible software to complete the image analysis system is to be used as part of this technique.

STUDY 1

A HSAA will be set up using normal control sperm. After addition of the sperm to the egg extract containing BrdUrd (10 μM, 92) in place of $^3$H-TTP, aliquots will be taken at 15 minute time intervals throughout the 3 hours of the HSAA, with cytopreps made as previously described. However, instead of performing autoradiography, the BrdUrd staining protocol of Royere et al (1988)[131], which reference is specifically incorporated herein by reference for this purpose, will be used. The cytopreps will be fixed in cold methanol-acetic acid (3:1 v/v) followed by an RNase treatment.

The procedure requires that the DNA be partially denatured to expose incorporated BrdUrd to the specific antibody. The anti-BrdUrd antibodies that have been developed so far only bind BrdUrd in single-stranded DNA. The DNA-denaturing step will be done by placing the cytoprep slides in Copeland jars containing distilled water at 95° C. for 10 minutes. The slides will then be transferred into Copeland jars containing ice cold distilled water for 2 minutes and the sperm nuclei stained using anti-BrdUrd antibody (Boehringer Mannheim, mouse IgG) in PBS as the manufacturer's recommended dilution, followed by rhodamine-conjugated Goat anti-mouse IgG. The stained nuclei will be analyzed individually in our image analysis system.

The number of stained nuclei that will be analyzed per time point will be decided based on the variability of the observed intensities of fluorescence. In a microspectrophotometric study of Feulgen stained human sperm nuclei, as few as 15 nuclei were scored per time point because only minor variability was observed in the measured fluorescence.[131] The image analysis measurements will be relative measurements with a base line of zero determined by measuring the background fluorescent intensity of decondensed control sperm nuclei (of similar size to the nuclei that will be analyzed at the later time points) after a 15 minute incubation in frog egg extract. There should have been little or no new DNA synthesized during this time, as the inventor has determined that DNA synthesis begins about 1.5 hours of incubation.

Based on the inventor's autoradiographic results, a steady increase in fluorescence intensity for the first 2 hours that will level off during the 2 to 3 hour interval of the assay is expected. This will demonstrate that the quantitative fluorescence microscopy approach detects the same trend in labelling as that shown when using the autoradiographic approach.

Study 2

A HSAA will be performed as described in study 1 using frog egg extract ± aphidicolin (10 μg/ml), a known inhibitor of DNA polymerase alpha. Aphidicolin is described in Ikegami et al (1978)[101]. This study will use sperm from a fertile male shown previously to respond normally in the HSAA. The present inventor has found that when human sperm were incubated in frog egg extract containing aphidicolin, decondensation and recondensation of the sperm nuclei was normal, but DNA synthesis was blocked.

Fluorescence intensities will be determined as previously described and plotted as fluorescence units above background fluorescence. A decrease in fluorescent intensity to base-line (the base-line defined when using sperm incubated in extract for 15 minutes) in the sperm incubated in frog egg extract containing aphidicolin is expected. Such will demonstrate that the quantitative fluorescence microscopy approach provides the same results as those obtained when using the autoradiographic approach.

EXAMPLE 21

Use of HSAA Assay as a Toxicological Screen of Human Sperm

Abnormal response of human sperm has been observed in at least one male patient that had a history of exposure to toxicological substances (See Example 13, fertile male (sired at least one child). This patient has not sired a child since the abnormal HSAA assay. Based on this observation, and the proposed anti-fertility effect of various toxicological agents, the present HSAA assay is proposed as an assay useful for evaluating toxic agents that affect human sperm nuclear decondensation, DNA synthesis and recondensation, as well as a method for screening patients exposed to toxic substances for sperm defects.

As a first step in using the HSAA as a toxicological screen, a cleavable cross-linker, SULFO-EGS (Pierce) was used to crosslink the sperm protamines and thereby block decondensation. Hydroxylamine was then used to chemically cleave the crosslinker and restore normal decondensation. This demonstrates that the HSAA can be used to detect chemically damaged sperm.

A representative list of environmental and other types of male reproductive toxins are listed below:[108]

Busulfan (fertility control in males)

alkylating agent that kills reserve and differentiating operamatogonia and reserve stem cell populations in the testis.

Procarbazine (alkylating anticancer drug used in treating Hodgkin disease)

affects the same cells low sperm count not reversible in some cases.

Methyl Chloride (chemical intermediate in multiple industrial applications)

halogenated hydrocarbon effects spermatid maturation 1,3-Dinitrobenzene (DNB) (nitroaromatic compound used widely as an intermediate in the synthesis of dyes and various plastics)

affects Sertoli cells testosterone responsive needed for final maturation of sperm high doses render permanently fertile low sperm count Sulfasalazine (treatment of inflammatory bowel disease)

reduced sperm count and fertilizing capability affected in treated patients.

antifertility effect may be mediated through a direct effect of sulfasalazine or its metabolite sulfapyridine on spermatozoa stored in the epididymis, hence compromising some processes vital for fertilization, specifically motility.

Dibromochloropropane (DBCP)

fungicide that when produced in 1977 male workers exposed by inhaling or through the skin in handling had noted fertility problems.

spermatogonia

Ethylene Dibromide (EDB)

motility, targets epididymis soil and grain fumigant and used in a tetraethyl lead mixture in gasoline.

low birth number in plant where produced.

EXAMPLE 22

Analysis of DNA Synthesis in Activated Sperm: Comparing the Quantitative Fluorescence Microscopy Approach With the Autoradiographic Approach Sperm from 100 unexplained infertile males in the HSAA as described above will be examined in the present example to provide the autoradiography data for comparison with the data obtained using quantitative fluorescence microscopy. The quantitative fluorescence microscopy data will be obtained by analyzing sperm from a fertile male and patients' sperm in parallel assays using aphidicolin treated extract. These samples will be imaged, and their average fluorescence determined in order to set the base-line. The sperm incubated in nontreated extract will be imaged and the average fluorescence over base-line determined.

The values obtained for each patient will be compared to the value obtained using control sperm from a fertile male, and recorded as % of the Control.

Statistical Analysis

Responses of both automated and manual approaches will be expressed in dichotomy (e.g., normal or abnormal). Agreement between both approaches in the dichotomous responses will be assessed using kappa statistical analysis[43]. 100% agreement is expected, i.e., kappa=1.0. Meanwhile, if the agreements are completely independent of each other, then kappa=0.00.

DAPI Staining and Flow Cytometry

Sperm from each of these patients and from a fertile male will be incubated for 2 hours in parallel assays (each containing 200,000 permeabilized sperm in 100 $\mu$l of egg extract); the sperm will then be washed in PBS and fixed with 70% ethanol. The sperm will be centrifuged and the fixative removed. The sperm will be resuspended in one volume of the pretreatment solution consisting of 0.2M citric acid and 0.5% Tween 20 and incubated at RT for 20 minutes with gentle shaking. Subsequently, 9 volumes of the staining solution containing 0.4M sodiumhydrogen phosphate and 5 $\mu$M DAPI will be added to raise the pH to ~7.0 and to stain the DNA. The stained cells are stable for 24–48 hours. The EPICS Profile flow cytometer will be used. Flow cytometric histograms of the DNA content of the sperm nuclei will be obtained. The nuclear content of the control sperm will then be compared with that of the patient sperm. The coefficients of variation in the range of 1% can be obtained in most specimens routinely. This allows for detection of small changes in DNA content when comparing the control sperm DNA content with that of the patients. Again, we will record the values as % of the Control and will consider the 80% of Control value to be indicative of an abnormal response in the HSAA.

Statistical Analysis

Responses of all three approaches (the quantitative fluorescence microscopy, the flow cytometer and the autoradiographic) are expressed in dichotomy. Agreement between the quantitative fluorescence microscopy and the autoradiographic approaches and also agreement between the flow cytometric and autoradiographic approaches in the dichotomous responses will be assessed using kappa statistics.

Alternative Approaches

Another approach for the staining of newly synthesized DNA with incorporated BrdUrd involves the use of the avidin-biotin system. This approach involves the use of antibodies and rhodamine-conjugated avidin, that can be obtained from Boehringer Mannheim. Other commercial sources of this standard reagent can also be used. The BrdUrd labelled nuclei will first be incubated with a mouse monoclonal Ig, followed by an incubation with biotin-conjugated goat anti-mouse IgG. The nuclei will then be stained with rhodamine-conjugated avidin and fluorescence intensities measured as previously described. Another possibility would be to use the Cy3 conjugated Goat Anti-mouse IgG (Chemicon). The Cy3 fluorophore is one of a new generation of fluorophores purported by the manufacturer to have a high fluorescence, low background and photostability that gives less background than rhodamine.

Several other staining procedures that stain total DNA may also be used as an alternative staining protocol. Staining approaches that can be followed by quantitative fluorescence microscopy include the use of Hoechst 33342, Feulgen stain, PI and DAPI. If we do not find the DPI staining-flow cytometry approach to be useful for the analysis of HSAA activated sperm, we will explore the use of the above mentioned stains as well as acridine orange.

Proposed Study

A standard HSAA will be set up using frog egg extract±aphidicolin (10 $\mu$g/ml), a known inhibitor of DNA polymerase alpha (29), and a fertile male's sperm shown previously to respond normally in the HSAA. We previously demonstrated that when human sperm were incubated in frog egg extract containing aphidicolin, decondensation and recondensation of the sperm nuclei was normal, but DNA synthesis was blocked (17). Sperm from the fertile male will be incubated for 2 hours in parallel assays (each containing 200,000 permeabilized sperm in 100 $\mu$l of egg extract with tritiated thymidine triphosphate); the standard autoradiographic approach will be used to determine the extent blockage (% labelled nuclei incubated in extract containing aphidicolin/% labelled nuclei incubated in extract without aphidicolin ×100), expected to be 20–30%. We will run a duplicate HSAA±aphidicolin (10 $\mu$g/ml), except minus tritiated thymidine triphosphate. After incubation, the sperm will be washed in PBS, fixed with 70% ethanol, centrifuged, and the fixative removed. The sperm will be resuspended in one volume of pretreatment solution (0.2M citric acid and 0.5% Tween 20) and incubated at RT for 20 minutes with gentle shaking. Subsequently, 9 volumes of the staining solution containing 0.4 sodium hydrogen phosphate and 5 $\mu$M 4', 6-diamidino-2-phenylindole (DAPI) will be added to raise the pH to ~7.0 and stain the DNA. The stained cells are stable for 24–48 hours, so can be shipped and/or transported by PI to Dr. Manimekalai's Laboratory where we will obtain flow cytometric histograms of the DNA content of the sperm nuclei. The nuclear content of the sperm nuclei that have synthesized their DNA with that of the sperm that had their DNA synthesis blocked. The coefficients of variations in the range of 1% can be obtained in most specimens routinely. Estimated DNA synthesis for the sperm nuclei incubated in extract containing aphidicolin will be determined, and determine if it is in the 20–30% range (observed using the autoradiographic approach) when compared to the estimated DNA synthesis for the sperm nuclei incubated in extract without aphidicolin. Several other staining procedures that stain total DNA may also be used. Staining approaches that can be followed by quantitative flow cytometry include the use of Hoechst 33342 (64) and acridine orange (96).

EXAMPLE 23

Method for Enhancing Chromosome Recondensation Analysis through Combination Interphase and Metaphase Incubation Media Protocol The egg extract used in the HSAA (see Example 3) is an interphase extract. It is described as such because permeabilized sperm incubated in this type of extract induces interphase-like sperm activation events including decondensation, DNA synthesis and the initial chromatin recondensation that precedes the recondensation of sperm chromatin to the metaphase chromosome level. Recondensation to the metaphase chromosome level must occur before cell division can take place.

Lohka and Maller[107] relate to a frog egg extract that is described as a metaphase extract. A metaphase extract, as used in this context, is an extract that allows for the formation of metaphase chromosomes upon addition of permeabilized sperm. The present invention proposes a method for assessing human sperm abnormalities using a combination technique, wherein permeabilized sperm from inexplicably infertile human males is first incubated (preferably for about 3 hours) in an interphase egg extract, such as the *Xenopus laevis* frog egg extract of Example 3, the sperm then being removed from the interphase extract (such as by slow speed centrifugation), and then resuspended in a metaphase egg extract, such as a *Xenopus laevis* or *Rana pipiens* frog extract. Once resuspended in the metaphase extract, the sperm will recondense to metaphase chromosomes. At this point, the percent of sperm that recondense to metaphase chromosomes can be determined at a set time interval, for example, after 3 hours. Patients that have <80% of the control nuclei that recondense to the chromosome level may be identified as having a sperm abnormality. This abnormality in chromosome recondensation may in some cases be diagnostic of the patient's infertility or suitability as a sperm donor for assisted reproductive techniques.

The metaphase-inducing extract is prepared from crude egg cytoplasmic extracts in such a way as to retain recondensation activity. The metaphase extract is isolated as previously described by Lohka[107]: An extract isolation buffer containing 80 mM β-glycerophosphate, 15 mM $MgCl_2$, 20 mM EGTA, 20 mM Hepes (pH 7.5), 1 mM DTT, 0.3 mM phenylmethysulfonyl fluoride and 3 μg/ml leupeptin. Extracts will then be centrifuged at 250,000 g for 4 hours in a ultracentrifuge before use as a metaphase extract according to the present invention.

EXAMPLE 24

DNA Synthesis and Frozen/Thawed Sperm

Permeabilized sperm can be stored frozen and then thawed for analysis in the HSAA without significant change in sperm decondensation activity. However, when permeabilized sperm is frozen and then thawed and reanalyzed for DNA synthesis in the HSAA, sperm with a pre-frozen/thaw abnormal DNA synthesis score display normal DNA synthesis by HSAA. This may be due to DNA damage that occurred during the freezing process. Nuclei containing such damaged nuclei when analyzed in the HSAA would demonstrate a normal DNA synthesis score. All of the nuclei would be labelled because DNA damaged by the freeze/thaw process would be repaired in the assay, thus incorporating the label used to detect DNA synthesis. Therefore, DNA synthesis scores of permeabilized sperm previously frozen would not be used alone as a diagnostic indicator of the normality or abnormality of a particular patient sample.

Figure 16B:
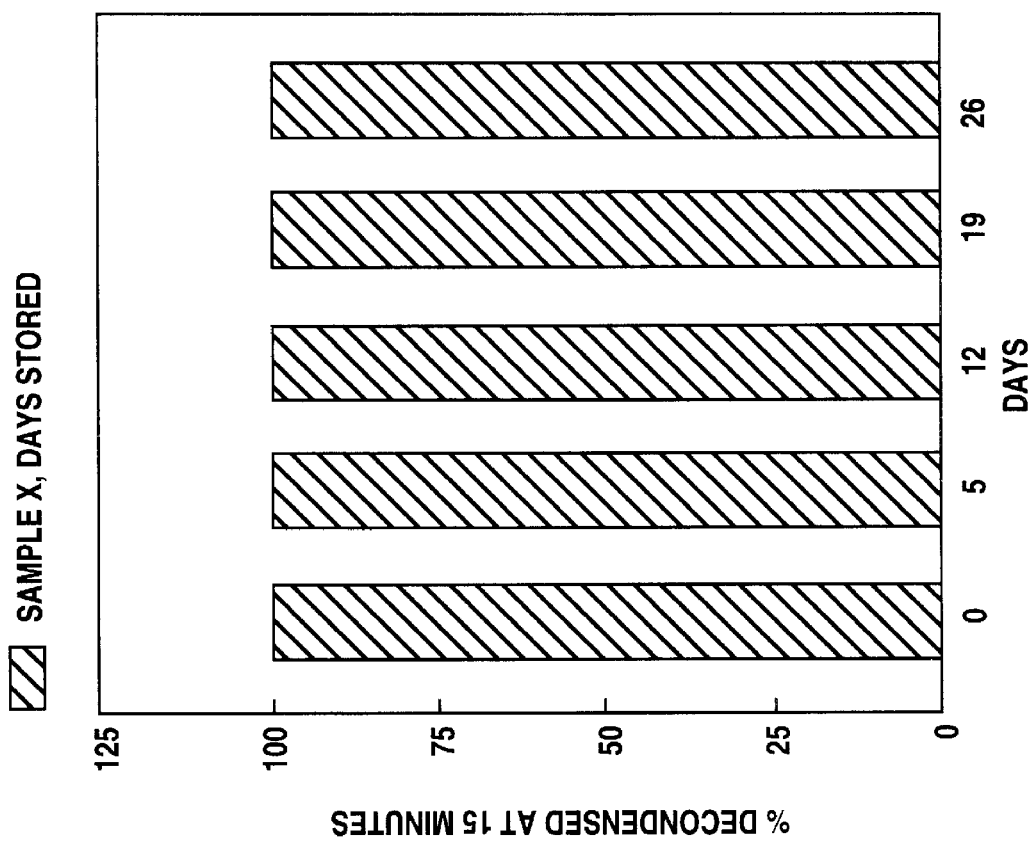
FIGS. 16A and 16B. Four ejaculates were collected from a fertile male whose sample is routinely used as a normal control in the HSAA, over a 26 day interval. The ejaculates were stores as semen at 4° C. On day 26, a fresh ejaculate was collected. All 5 semen samples were permeabilized and prepared for analysis in the HSAA as described in Example 2. The HSAA was performed as described in Example 9 for the control sample. (16A) 15 minutes. All sperm had fully decondensed (100%) after a 15 minute incubation in the frog egg extract. (16B) 2 hours. All sperm were labelled (100%) after a 2 hour incubation in the frog egg extract. Note: we were unable to obtain the data for the 19 day sample as the slide prepared for autoradiography was not interpretable for technical reasons (very high background) that we are unable to sort out. We are repeating the autoradiography of this sample's 2 hour cytoprep and will forward the information as soon as we finish the experiment.
Figure 16A:
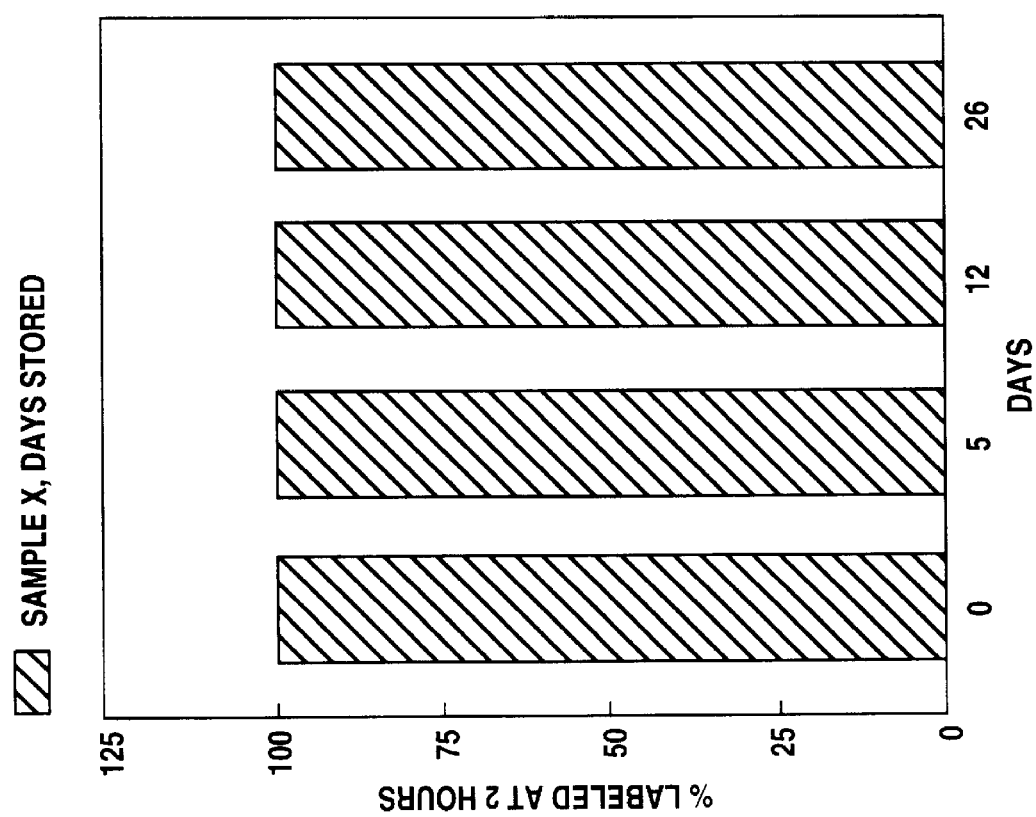
Figure 17A:
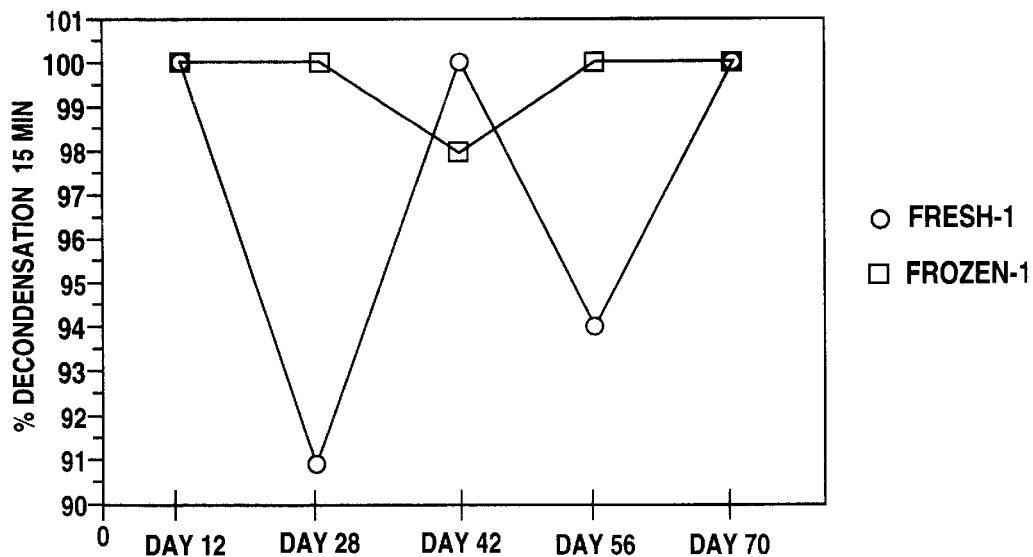
FIG. 17A. Percentage of sperm from a fertile male that decondensed during a 15 minute incubation in thawed extract that had been stored in liquid nitrogen for 12, 28, 42, 56 and 70 days. A fresh extract was prepared on each of the assay days and sperm from the same permeabilized control sample were analyzed in both the thawed and fresh extracts.
Figure 17B:
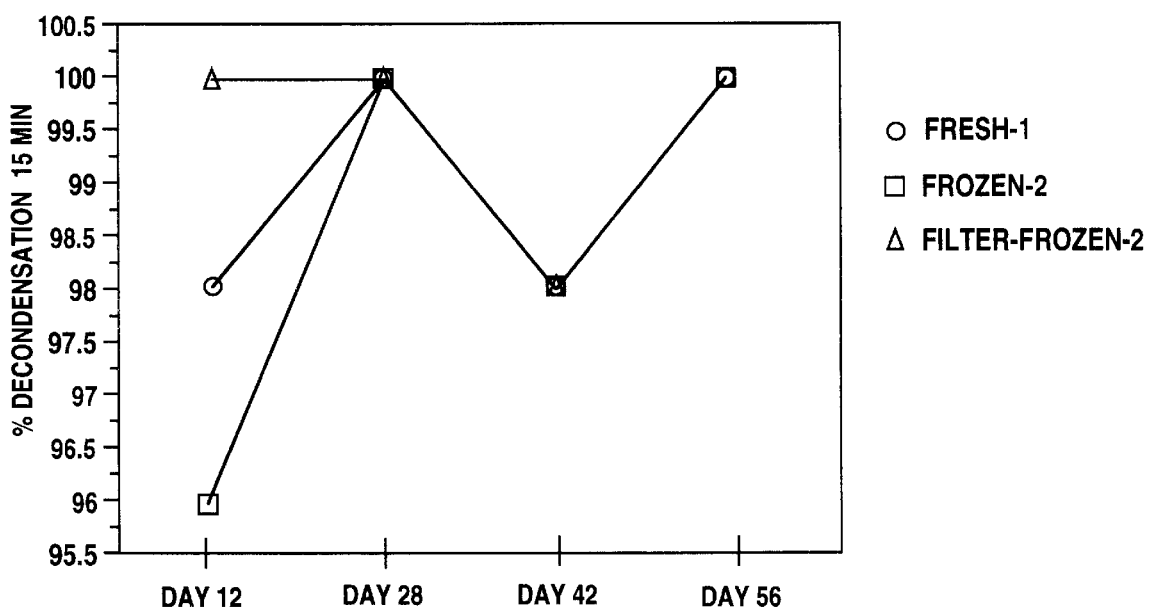
FIG. 17B. Percentage of sperm from a fertile male that decondensed during a 15 minute incubation in thawed extract and thawed filtered extract that had been stored in liquid nitrogen for 12, 28, 42 and 56 days. A fresh extract was prepared on each of the assay days and sperm from the same permeabilized control sample were analyzed in both the thawed and fresh extracts.

The present example is provided to demonstrate the micro-freeze technique for the egg extract used in the present assay. The FIGS. 17A–17B and 18A–18B illustrate the freeze thaw data. FIGS. 16A–16B demonstrates the reproducibility of the assay using human sperm stored at 4° C. for up to 26 days using the HSAA assay.

EXAMPLE 25

Screening of Human Sperm with Low Sperm Number Application to Intracytoplasmic Sperm Injection Regimens (ICSI)

The present example is provided to demonstrate the utility of the present invention in analyzing human sperm in the present methods with a small number of sperm. Hence, the presently disclosed methods may be conducted along with other fertility assessing techniques without the necessity of obtaining additional sperm sample from the patient. In addition, the scaled down amount of sperm necessary in the present application of the assay to samples where only very small amount of sperm are available from the patient. This is the case, for example, where sperm is removed surgically to obtain epididymal sperm, or in patients who have very low sperm counts.

Papers that describe the general protocol for ICSI include Atiee et al (1995) (Fertility and Sterility, 63:3), which reference is specifically incorporated herein by reference for this purpose. This article describes an injection apparatus and method for performing intracytoplasmic sperm injection in a clinical IVF program. The presently described assay may thus be used to screen a small portion of a human semen sample for ability to support sperm activation events, while bypassing all sperm function defects.

The assay to monitor sperm activation events may be conducted with a human sperm sample containing less than about 20 million, such as about 400,000 to about 5 million, or about 400,000 to about 800,000 sperm. This is a significantly lower number of sperm needed for most other forms of sperm fertility testing. This application of the assay is shown to be effective for monitoring the sperm activation events of chromatin decondensation, DNA synthesis, and chromatin recondensation. The protocol used was similar to that described infra, with the following recommended modifications that were found at least in some cases to improve assay results.

1. Avoid use of a standard pipette to resuspend the human sperm sample. For example, the use of a vortexer would allow suspension of the sperm sample without potential loss of sperm.

2. Filtering of the egg extract prior to using with the human sperm sample. For example, the egg extract, such as the frog extract discussed above, should be filtered, such as with a 0.45 micron filter, before using the assay. The egg extract should be filtered before any freezing of the extract, or any other storage or processing of the egg extract.

3. Optionally, the human sperm sample 1 may also be filtered. For example, such may be included as a step where an epididymal sperm sample is being analyzed. A large-pore size filter (e.g., one layer sterile gauze) may for example separate epididymal sperm from the biopsy debrie.

The procedure used in Example 9 will be used in the presently proposed screening protocol, with the noted exceptions outlined above.

EXAMPLE 26

Regimen for Testing Unexpicably Infertile Couples with HSAA

Although other tests of human sperm function have been developed, the HSAA and the SPA directly assay sperm activation events. The SPA tests the capacity of sperm to bind and penetrate hamster zona-free ova. The SPA score is the percentage of penetrated ova, determined by counting the ova that contain decondensed or activated sperm nuclei (pronuclei). Although both assays score activated sperm, the SPA cannot be used to study the efficiency of the decondensation process. During the SPA, the hamster ova routinely become bound with a large number of sperm that do not penetrate and thus do not decondense. Nondecondensed sperm bound to the ova cannot be differentiated from sperm that have penetrated ova and not decondensed as a result of not responding to activation signals in the ova. Interestingly, a zero SPA score may in some cases reflect the sperm's inability to decondense instead of its penetration capabilities.

In a study analyzing the sperm samples from 443 men having 0% SPA scores, and 0–3 abnormal sperm parameters, 16.3% of these males had no readily detectable sperm abnormalities, i.e., unexplained infertility[72]. It is not known whether the 0% SPA scores were a result of the sperm not penetrating ova, not decondensing in penetrated ova, or a combination of both. As for the possibility of using penetrated hamster ova to monitor DNA synthesis and recondensation, the labor and expense that would be required to obtain enough ova to analyze one patient would prohibit this approach as a routine clinical procedure.

The HSAA allows routine comparison of hundreds of a patient's activated sperm nuclei with those from a normal, fertile male, and easily detects any abnormal response, and so is the clear assay of choice for assaying sperm activation. However, the HSAA cannot detect male infertility that is caused by the sperm's inability to penetrate the egg. The combined use of the HSAA and assays of the fertilization events occurring before sperm activation (e.g. the SPA, tests of the acrosome reaction, acrosin activity, and zona-binding) will identify a greater percentage of infertile males than any one assay alone.

Of the 16 abnormal responders in the HSAA to date, 10 also had their sperm analyzed in the SPA. Five of the patients had penetration scores of less than 10% (considered abnormal, 18; all scored 0%), and 5 had scores greater than 10%. SPA scores were also determined for 34 of the 58 unexplained infertility patients whose sperm responded normally in the HSAA. Nine of the 34 samples assayed had abnormal SPA scores of less than 10% (three 0% scores). These data are summarized in Table 3.

TABLE 3

Comparison of HSAA and SPA Results

| Patient No. | Abnormal Response in the HSAA | SPA Score |
|---|---|---|
| 1 | Decondensation | 60% |
| 2 | Decondensation/DNA Synthesis | 0% |
| 3 | Decondensation | 16% |
| 4 | Decondensation/DNA Synthesis | 69% |
| 5 | Decondensation | 0% |
| 6 | DNA Synthesis | 64% |
| 7 | Decondensation | 28% |
| 8 | Decondensation | 0% |
| 9 | Decondensation | 0% |
| 10 | Decondensation | 0% |

| Patient Nos. | Normal Response in the HSAA | SPAScores |
|---|---|---|
| 11–44 | YES | 0%, 15%,15%, 0%, 30%, 0%,20%,30%, 24%, 40%, 4%, 5%, 18%, 20%,27%, 8%, 59%, 52%,23%,20%, 70%, 8%,70%, 8%, 53%, 8%,33%,30%, 14%, 14%,58%,67%, 34%, 17% |

In this study, a portion of the semen sample that was not used in attempts at pregnancy via ARTs, including superovulation and timed IUI with precapacitated sperm, GIFT, or IVF-ET, was used. No false positive results were observed where the patient's sperm responded abnormally in the HSAA but resulted in a successful pregnancy when used in an ART attempt. Two of the idiopathic infertile male patients who produced sperm that initially responded abnormally in the HSAA have at a later time provided sperm that have responded normally in the HSAA, and when used in ART attempts resulted in pregnancies. One of these patients provided a sample 4 months after the initial HSAA test date that responded normally in the HSAA (52% of the Control Decondensation Score in initial assay, 100% of the Control Decondensation Score in a later assay). This later sample resulted in a pregnancy when used in the IVF-ET procedure; however, the pregnancy ended with a spontaneous miscarriage at six weeks of pregnancy. The other patient provided a sample (just 18 days after the initial HSAA test) that responded normally in the HSAA (17% of the Control Decondensation Score in initial assay, SPA score of 0%; 111% of the Control in later assay, SPA score of 11%). Again the second sample resulted in a pregnancy when used in the GIFT procedure; the pregnancy went to term, with delivery of a normal child. Seven inexplicably infertile couples were removed from this study when sperm from the male was used in ARTs and pregnancy resulted, i.e., they were no longer inexplicably infertile. All 7 of these samples responded normally in the HSAA (80% or greater DNA synthesis, chromatin decondensation and chromatin recondensation relative to known fertile male. These data support the contention that the HSAA can be used to determine a sperm sample's efficacy for fertilization. Further confirmation of this will be obtained in further studies to correlate HSAA with IVF fertilization rates.

Of the 74 fertile males whose sperm have been analyzed in the HSAA (n=15, Example; n=59, Example 9), only one produced sperm that responded abnormally in the HSAA. This particular case is discussed at Example 21.

The average age of both the fertile and infertile males was 35, with a range of 22–52 years and 23–50 years, respectively. The average age of the abnormal responders was 34. Thus, there was no correlation between age and an abnormal response in the HSAA. (See Example 12).

EXAMPLE 27

HSAA in Detection of Chemical Damage of Human Spermatozoa

The human sperm activation assay (HSAA) involves incubating lysolecithin-permeabilized sperm in *Xenopus laevis* ova cytoplasmic extract as well as other egg extracts that are capable of supporting human sperm activation events, chromatin decondensation, DNA synthesis and/or chromatin recondensation. Factors in the egg extract are contemplated to activate sperm nuclei.

The present study demonstrates the utility of the invention methods for detecting chemical sperm damage, as it shows that human sperm chemically damaged by treatment with a reversible crosslinker, ethylene glycolbis (sulfosuccinimidylsuccinate; SEGS), display abnormal chromatin decondensation when analyzed in the HSAA. Less than 20% of SEGS-treated sperm fully decondensed, versus 97% of control sperm. Chemical reversal of the crosslinks by treatment with 5 $\mu$M hydroxylamine restored full decondensation in 76% of treated sperm.

These results demonstrate that chemically damaged sperm respond abnormally in the HSAA, and that chemical damage to sperm nuclei can be detected using the HSAA. Thus, the HSAA can be used to detect chemical alterations of sperm nuclei from men exposed for example, to environmental toxicants.

Using the HSAA, 21.6% of unexplained infertility patients tested have been diagnosed with abnormal post-penetration sperm activity, including attenuated or incomplete chromatin decondensation and/or reduced levels of DNA synthesis. Furthermore, all idiopathic infertile males' semen samples which responded abnormally in the HSAA were also unsuccessful in Assisted Reproductive Technology (ART) attempts, including superovulation and timed intrauterine insemination with precapacitated sperm, gamete-intrafallopian transfer (GIFT), and in vitro fertilization-embryo transfer (IVF-ET). A 100% correlation between a normal HSAA response and IVF-ET success has also been shown.

The existence of male reproductive system toxicants, some of which have the potential to interfere directly with sperm-nuclear activation, led to the herein described use of the Human Sperm Activation Assay for detecting chemically damaged sperm nuclei.

A reversible, homo-bifunctional crosslinking agent, ethylene glycolbis[sulfosuccinimidylsuccinate] (SEGS) was used in the present study to introduce chemical damage into human sperm nuclei in vitro. This agent is representative of any number of chemical agents that are also crosslinking agents, such as cyclophasphamide and MeCCNU (these agents are typical chemotherapy agents, and are used to kill cycling cells and/or generally to effect the cell cycle), or other compositions that may include agents that interfere with sperm nuclear activation. Detection of this damage using the HSAA is shown. Human sperm treated in vitro with SEGS did not decondense. The decondensation block was shown to be due to covalent cross-links because treatment of crosslinked sperm with hydroxylamine (NH$_2$OH), which specifically cleaves SEGS cross-links, restored decondensation. These results demonstrate that the HSAA may be a useful tool for detecting sperm chemically damaged in vivo by toxicant exposure.

Materials and Methods

Semen Collection: Human sperm were obtained from a fertile donor via masturbation. All semen samples were used within 60 minutes of ejaculation. Solutions: A 5 mM SEGS solution was made by dissolving 3.3 mg SEGS (Pierce, Rockford, Ill.) in 1 ml Phosphate Buffered Saline (PBS; pH=7.5). A 5 mM stock hydroxylamine (NH$_2$OH) solution was made by dissolving 1.7 mg hydroxylamine hydrochloride (NH$_2$OH.HCl; Pierce) in 5 ml PBS and adjusting the pH to 8.5 with 10N NaOH. A 5 $\mu$M NH$_2$OH solution was then prepared by serially diluting the stock solution with PBS (pH=8.5).

Frog Egg Extract and Semen Sample Preparation

Frog egg extract from Xenopus laevis was prepared as described in Example 2. Semen samples were prepared as described in Example 2, with the following modifications: Twenty million sperm were incubated in 10 ml of a 0.05% lysolecithin solution for 5 minutes to permeabilize the sperm membranes. Sperm were pelleted from the permeabilization solution by centrifugation (400 g for 10 minutes), resuspended in 1 ml 3% Bovine Serum Albumin-Nuclear Isolation Medium (BSA-NIM; NIM: 17.1 g sucrose, 0.145 g maleic acid, 0.395 g Tris HCl, 0.12 g MgCl$_2$, 2.5 ml penicillin (10,000 u/ml)-streptomycin(10 mg/ml), water to 250 ml), and transferred to a 1.5 ml Eppendorf tube. The sperm suspension was centrifuged*, the pellet washed with 1 ml 0.4% BSA-NIM, pelleted again*, and resuspended in 1.05 ml 0.4% BSA-NIM. An aliquot (50 $\mu$l) of this suspension was diluted with 50 $\mu$l 0.4% BSA-NIM, and the sperm counted in an Improved Neubauer hemocytometer. The remainder of the sperm were pelleted by centrifugation* and resuspended in PBS (pH=7.5) to a concentration of 25,000 sperm/$\mu$l. Aliquots (800,000 sperm in 32 $\mu$l) were transferred to each of four 1.5 ml Eppendorf tubes, labeled 1–4. To tubes 1 (dual control) and 3 (crosslinker control) were added 68 $\mu$l PBS (pH=7.5). To tubes 2 (hydroxylamine control) and 4 (dual treatment) were added 68 $\mu$l of the 5 mM SEGS solution (final [SEGS]=3.4 mM). After a 30 minute incubation, all tubes (1–4) were centrifuged* to pellet the sperm, and each pellet washed with 100 $\mu$l PBS (pH=8.5). Sperm were again pelleted by centrifugation*. The pellets in tubes 1 and 2 were resuspended in 200 $\mu$l PBS (pH=8.5). The pellets in tubes 3 and 4 were resuspended in 200 $\mu$l of the 5 $\mu$M NH$_2$OH solution (pH=8.5). After a 5 hour incubation, all tubes (1–4) were centrifuged* to pellet the sperm. Each pellet was resuspended in 50 $\mu$l XEIM (Xenopus Extract Isolation Medium: 0.03 g MgCl$_2$, 0.12 g Tris HCl, 0.75 g KCl, 0.76 g dithiothreitol (DTT), 1 ml penicillin(10,000 u/ml)-streptomycin(10 mg/ml), in 100 ml water, pH to 7.6), and a count was taken. The sperm were pelleted by centrifugation*, resuspended in XEIM to a concentration of <25,000 sperm/$\mu$l, and placed on ice for 1 hour. The HSAA was performed on each sample (tubes 1–4) as described below. The study is summarized in Table 4.

TABLE 4

| | Sequential Treatment | |
|---|---|---|
| Tube | 30 minutes, pH = 7.5 | 5 hours, pH = 8.5 |
| 1. Dual Control | PBS | PBS |
| 2. SEGS Control | 3.4 mM SEGS | 5 $\mu$M NG$_2$OH |
| 3. NH$_2$OH Control | PBS | 5 $\mu$M NG$_2$OH |
| 4. Experimental | 3.4 mM SEGS | |

An aliquot (100 $\mu$l) of the extract was added to each sample in tubes 1–4, designated as time=0. Each mixture will be referred to as a Sperm-Extract Mix (SEM). All SEMs were treated identically thereafter. At 10 minutes, 5 $\mu$l of the SEM was removed, placed on a slide, coverslipped, and visualized using a Leitz phase-contrast microscope. 50 sperm heads were counted and scored as fully decondensed or non-decondensed (including partials). At 15 minutes, the above step was repeated, and photographs taken of representative examples of sperm heads (FIG. 15). At 20 minutes, 25 $\mu$l of the SEM was removed and placed in a 1.5 ml Eppendorf containing 75 $\mu$l PBS (pH=7.5). Cytopreps were then made by placing 50 $\mu$l into each of two cytoprep assemblies which were centrifuged (Shandon cytocentrifuge) at 2000 rpm for 3 minutes (high acceleration setting).

Results

Figure 12:
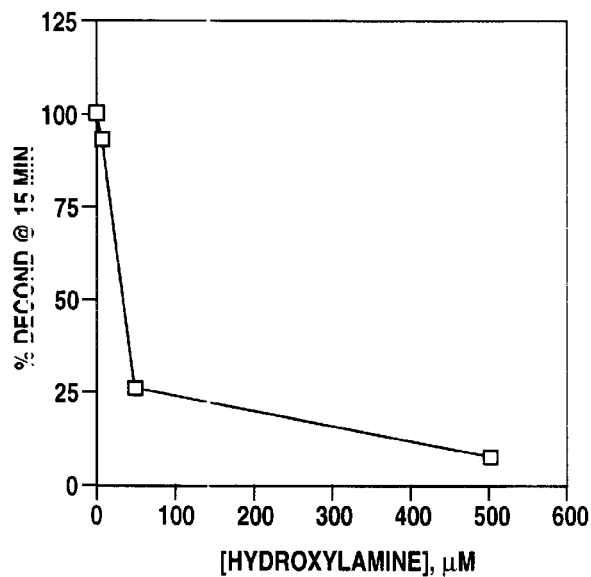
FIG. 12. Dose-response curve for the effect of hydroxylamine on sperm nuclear decondensation. X-axis is hydroxylamine concentration; Y-axis is % of sperm that fully decondensed after 15 minutes in the extract (n=50 sperm scored for each data point). 800,000 sperm were treated with the indicated hydroxylamine concentrations for 5 hours.
Figure 13:
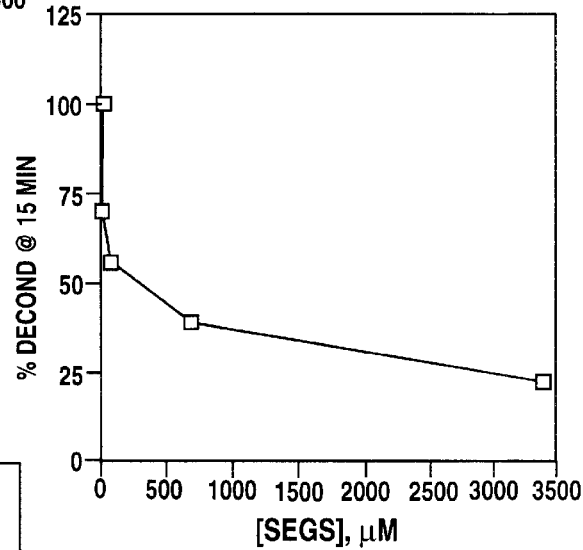
FIG. 13. Dose-response curve for the effect of SEGS on sperm nuclear decondensation. X-axis is SEGS concentration; Y-axis is % of sperm that fully decondensed after 15 minutes in the extract (n=50 sperm scored for each data point). 800,000 sperm were treated with the indicated SEGS concentrations for 30 minutes.

The design of this study allowed us to introduce chemical damage into the sperm nucleus, assess functional alterations induced by the chemical, and reverse the damage to establish the mechanism of injury. Dose-response data for NH$_2$OH and SEGS are shown in FIGS. 12 and 13, respectively. These experiments were performed to establish appropriate concentrations of each reagent to be used in these experiments. Hydroxylamine concentrations higher than 5 $\mu$M had an adverse effect on decondensation. Obviously, these concentrations were inappropriate to use for the crosslink reversal experiments. 5 $\mu$M hydroxylamine had no effect on decondensation, but was able to remove the crosslinker (at the concentration of SEGS used). Decondensation was consistently prevented in more than 75% of the sperm treated with 3.4 mM SEGS. Also, we wanted to use as low a SEGS concentration as possible to facilitate the easiest reversal possible with hydroxylamine, i.e., at the lowest hydroxylamine concentration possible. Thus, the SEGS/NH$_2$OH ratio was optimized to facilitate adequate crosslinking while retaining the ability to remove the cross-links.

Figure 14:
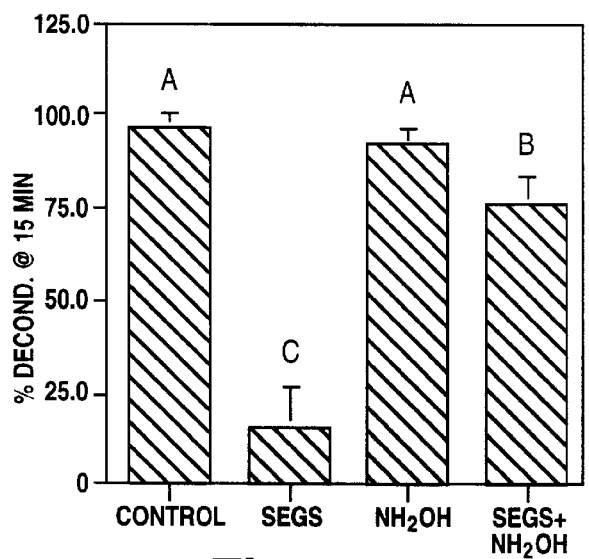
FIG. 14. Comparison of sperm nuclear decondensation in the different treatment groups described in the text. Each bar value is mean ± S.D. of three experiments per treatment group. Values are % of sperm fully decondensed after 15 minutes in the extract (n=50 sperm scored in each experiment).

As can be seen in FIG. 14, 16.0±9.1% of the SEGS-treated sperm decondensed versus 97.3±2.5% of the control. Hydroxylamine had no effect when given alone (92.0±2.8% decondensed at 15 minutes), yet it was able to reverse most of the crosslinks; 76.0±5.9% of the sperm that were crosslinked, and then treated with hydroxylamine, were able to decondense. These data suggest that the failure to decondense observed was due to the crosslinks (FIG. 14).

Figure 15A:
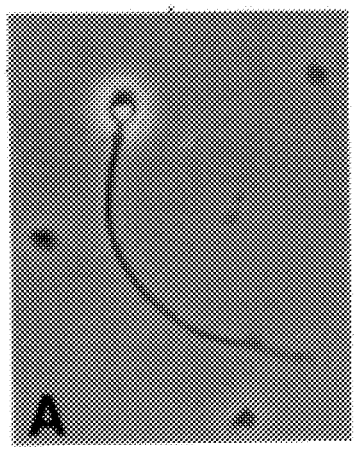
FIGS. 15A–15G. Phase contrast photographs of sperm heads showing normal (control) and abnormal (chemical-treated) responses. (A) Time=0, condensed head of a permeabilized sperm before addition of extract. (B) Typical example of a permeabilized, dual control sperm after 15 minutes in the extract displaying normal decondensation. (C, D, E) Typical example of a permeabilized, SEGS-treated sperm after 15 minutes in the extract showing a range of abnormal decondensation responses seen, from severe (C) to mild (E). (F) Typical example of a permeabilized, hydroxylamine-treated sperm after 15 minutes in the extract showing normal decondensation at the dose of hydroxylamine used (5 μM). (G) Typical example of a permeabilized, dual-treated sperm (SEGS, then hydroxylamine, as described in the text and in Table 1) after 15 minutes in the extract showing restored, normal decondensation. Scale bar=10 μM.
Figure 15B:
Figure 15C:
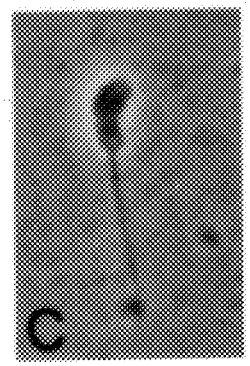
Figure 15D:
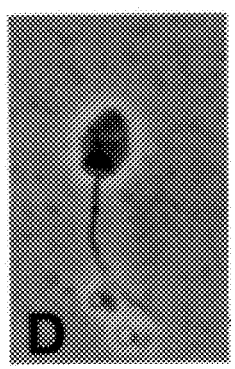
Figure 15E:
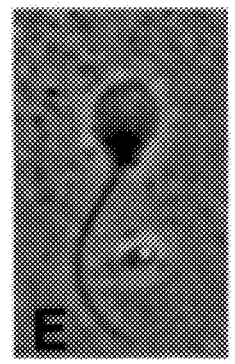
Figure 15F:
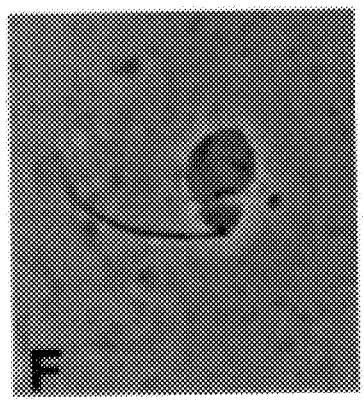
Figure 15G:
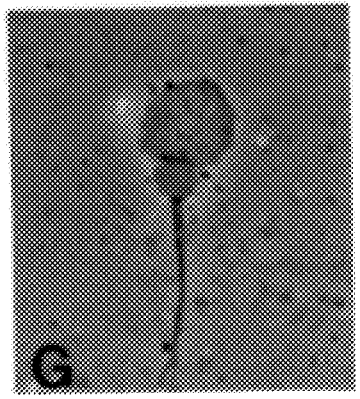

FIG. 15A–15G shows photomicrographs of sperm treated as described in the figure legend. Panel A is a dual control sperm at time=0, showing a normal, condensed head before nucleus activation. Notice that the sperm head is small and phase-dark. After addition of the frog egg extract, the sperm are activated, and undergo decondensation as described above. FIG. 15B shows a dual control sperm after a 15 minute incubation in frog egg extract. The head swells to 7× its original size, becoming phase-light, indicating that the chromatin is dispersing. In contrast to dual control sperm, less than 20% of the SEGS-treated sperm fully decondense (16.0±9.1%). FIG. 15C, FIG. 15D, and FIG. 15E (FIGS. 15C, D and E) are photomicrographs representative of SEGS-treated sperm heads, showing the range of effects on decondensation seen. Some sperm heads remain condensed (FIG. 15C), while others partially or fully decondense (FIG. 15D and FIG. 15E). As described in the Methods section, only fully decondensed sperm heads (typified by FIG. 15B, FIG. 15E, FIG. 15F, and FIG. 15G) were scored as "decondensed". Partials (e.g., FIG. 15D) were scored as non-decondensed; the rationale for this scoring system is that any degree of non-decondensation indicates chemical damage, i.e. only chromatin that remained "untouched" by the crosslinking agent would fully decondense. This data shows that the chemical damage results in abnormal human sperm decondensation. Partials represent an abnormal response when compared to controls; thus, they were scored as non-decondensed. These differences in the degree of decondensation likely arise as a result of nonideal behavior of the chemical and sperm heads in solution, and/or nonquantitative crosslinking of sperm chromatin macromolecules. FIG. 15F is a sperm treated with 5 $\mu$M NH$_2$OH; the sperm head is fully decondensed (as dual control sperm) indicating this concentration of hydroxylamine had no effect, qualitatively (FIG. 15F) or quantitatively (FIG. 14), on decondensation. FIG. 15G shows a sperm from the dual treatment group, i.e., treated with SEGS, then hydroxylamine. As can be seen, many of these sperm decondensed (76%, FIG. 14), indicating that the decondensation block was due specifically to the covalent crosslinks induced by treatment with SEGS.

These studies were undertaken to demonstrate that chemically damaged sperm respond abnormally in the Human Sperm Activation Assay. Human sperm chemically damaged by a reversible crosslinking agent, SEGS, do not decondense. Thus, the HSAA is a useful tool for screening known and potential toxicants for their ability to interfere with sperm nuclear activation, and/or, to detect exposure to reproductive toxicants. The rationale that led to use a crosslinking agent for these studies was the observation that prior to fertilization, decondensation is prevented by disulfide crosslinks in the nucleoprotamine structure of the sperm chromatin[67,124]. SEGS is known as an N-hydroxy succinimide ester which specifically reacts with primary amino groups (Pierce, manufacturer's instructions). While not intending to be limited to any particular mechanism of action or class of chemicals that cause sperm abnormality, it is contemplated that taking place is a crosslinking of either protamine primary amino groups, arginine side chain amino groups, or both. Protamines are known to be arginine-rich[124]. Because SEGS is reversible, a way is provided to show that the chemical damage was specifically due to the covalent crosslinks.

In summary, these results demonstrate that human sperm chemically damaged in vitro respond abnormally in the HSAA; sperm treated with the crosslinking agent do not decondense. The damage was shown to be due to covalent crosslinks, as hydroxylamine treatment reversed the damage. These results demonstrate that the HSAA is a useful tool for detecting sperm chemically damaged in vivo by toxicant exposure.

EXAMPLE 28

Frozen Egg Extract in HSAA Analysis

The present example is provided to demonstrate the micro-freeze technique for the egg extract that may be used in the practise of the present invention.

Protocol for Freezing, Storing, Thawing and Testing Frog Egg Extract Activity

1. Egg extract lots 1 and 2 were prepared as described in Example 2. Extract lot 2 was divided into two tubes. One tube containing non-filtered lot 2 extract, the other tube containing lot 2 extract that was filtered using a low protein binding 0.45 micron filter (Uniflo-25, 02340, Schleicher and Schuell, Kene, N.H. 03431).

2. Filtered and non-filtered extract was "snap frozen" by pipetting 15 $\mu$l drops into stirred liquid nitrogen. Seven to nine frozen beads (enough for 1 assay) were transferred into cryovials containing liquid nitrogen. These vials were then placed in storage canes that were inserted into the liquid nitrogen storage vessel. On days 12, 28, 42, 56 and 70, cryovials containing filtered and non-filtered extract were rapidly thawed in a 37° C. water bath, removing vials from the water bath as soon as the beads melted, and storing on ice until performing the HSAA as described in Example 9. However, only control sperm from a fertile male (prepared as described in Example 2) was analyzed in the assay as we are comparing extract activities as regards the % of sperm nuclei that decondensed within 15 minutes, the % of labelled nuclei at 2 hours that had synthesized their DNA and the % of nuclei that had recondensed at 3 hours. On each of the testing days, a fresh extract was also prepared (as described in Example 2) and parallel assays run.

Results

Figure 18A:
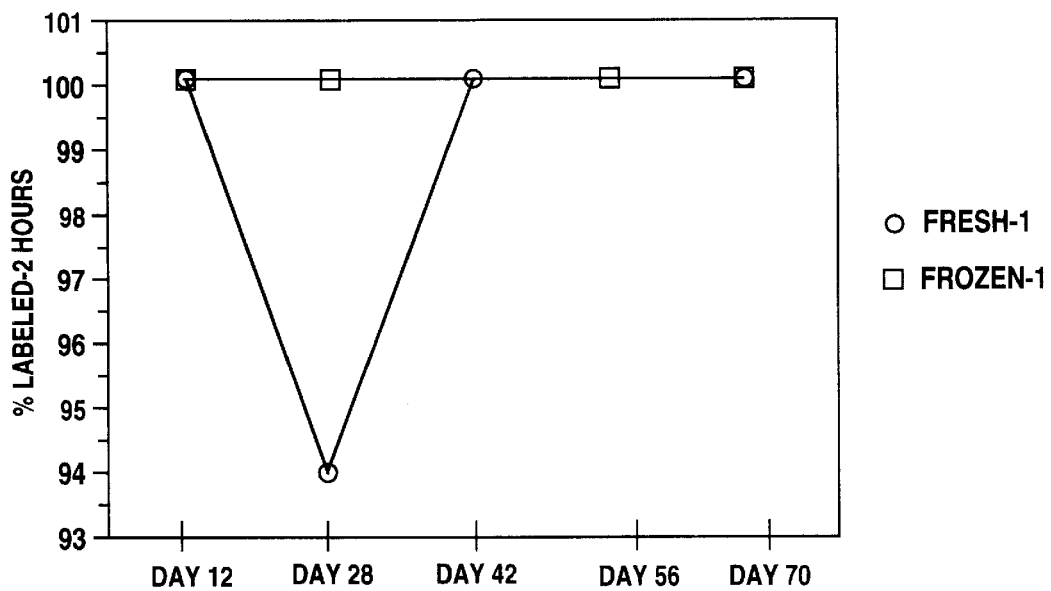
FIG. 18A. Percentage of sperm from a fertile male that synthesized DNA during a 2 hour incubation in thawed extract that had been stored in liquid nitrogen for 12, 28, 42, 56 and 70 days. A fresh extract was prepared on each of the assay days and sperm from the same permeabilized control sample were analyzed in both the thawed and fresh extract.
Figure 18B:
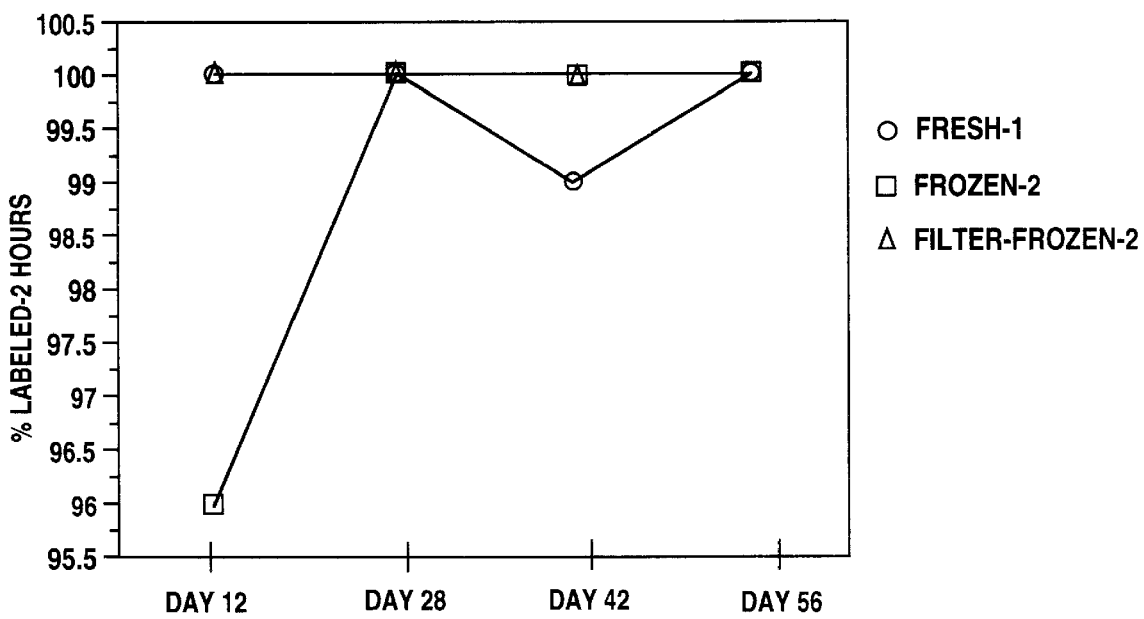
FIG. 18B. Percentage of sperm from a fertile male that synthesized DNA during a 2 hour incubation in thawed extract and thawed filtered extract that had been stored in liquid nitrogen for 12, 28, 42 and 56 days. A fresh extract was prepared on each of the assay days and sperm from the same permeabilized control sample were analyzed in both the thawed and fresh extract.

The data was plotted for both decondensation (FIG. 17A–17B) and DNA synthesis (FIGS. 18A–18B). The recondensation was 100% in all assays and was not plotted. Both the lot 1 and lot 3 frozen samples were shown to have retained full sperm activation activities following thawing, after up to 70 days of storage in liquid nitrogen. The main variability in extract activity was observed in the fresh samples. When using filtered extract in performing the HSAA, it was found that the scoring of decondensed nuclei was much easier to perform, without affecting sperm activation activities.

The filtered-frozen extract may also be used in the kit. Thawed extract is expected to be useful to identify abnormal responders at the same frequency as has already been shown when using fresh egg extract. The studies described in Example 27 will further verify that the thawed extract can be used to detect chemically damaged sperm as previously demonstrated using fresh egg extract.

As part of the preparation of the frozen egg extract, the dropwise addition of the extract can be made in some embodiments by either stirring the liquid nitrogen, or other liquid capable of snap-freezing an egg extract, or simply swirling the liquid around such that the extract drop is immersed completely at one time. The egg extract is to be prepared essentially as described in example 2, and then frozen according to the above method.

EXAMPLE 29

Use of HSAA to Detect Defective Human Sperm Chromatin

Presently, there is no explanation for why some individuals' sperm do not activate normally in the HSAA. Sperm may have abnormal spermiogenesis resulting in defective chromatin. During human spermiogenesis, the chromatin containing nucleosomal histones is converted to chromatin packaged mainly by three different protamine molecules (reviewed in 116). A chromatin defect involving aberrant protamine ratios has been suggested as a possible explanation for some known and recognized cases of male infertility[116-117]. Further evidence linking defective chromatin and male infertility is provided in studies where: cytometric analysis of acridine orange-stained heated sperm from humans of low fertility and from fertile males revealed a significant decrease in resistance to in situ denaturation of the sperm from the subfertile males[111]; acridine orange-stained human sperm from nonfertile donors were shown to have significantly fewer intact nuclei containing double-stranded DNA than did sperm from fertile donors[118]; and in vitro nuclear chromatin decondensation and quantitative nuclear ultramorphology analysis of human sperm from males who had failed in vitro fertilization of the ova from their wives revealed a significant decrease in sperm chromatin stability and an increase in hypoelongated sperm-heads from the infertile male group, vs. sperm from fertile males[119].

The chromatin of sperm that respond abnormally in the HSAA will be further analyzed to determine if the abnormal response is linked to defective chromatin. Understanding sperm activation events at the molecular level of this sort will also provide information useful for the development of new therapies in male infertility.

The present example is provided to demonstrate the reliability and reproduceability of the HSAA in males diagnosed as having an unexplained cause of infertility, and not having been examined for abnormal protamine ratios.

While those of skill in the art will be able to practice the present invention with the aid of the disclosure provided here, the following references may facilitate practice or enhanced understanding of certain aspects. Inclusion of a reference in this list is not intended to and does not constitute an admission that the reference constitutes prior art with respect to the present invention.

The following references are specifically incorporated herein in pertinent part for the particular purposes indicated insofar as they supplement the specific information described herein.

BIBLIOGRAPHY

1. Lohka, M. and Y. Masui. Formation in vitro of Sperm Pronuclei and Mitotic Chromosomes Induced by Amphibian Ooplasmic Components. Science, 220 (1983) 719–721.
2. Collins J. A., Crosignani P. G. Unexplained infertility: a review of diagnosis, prognosis, treatment efficacy and management. Int J. Gynecol Obstet 1992; 39:267–75.
3. Brown D. B., Nagamani M (1990); *J. Cell Biol.*, 111:115a.
4. World Health Organization: Appendix 1.A, Normal values of semen variables. In WHO laboratory manual for the examination of human semen and semen-cervical mucus interaction. New York: Cambridge University Press, 1987, p.27
5. Kasinsky H. E., Huang S. Y., Mann M., Roca J., Subirana J. A. (1985); *J. Exp. Zool.*, 234:33–45.
6. Kasinsky H. E. (1989). Specificity and distribution of sperm basic proteins. In Histones and Other Basic-Nuclear Proteins. Edited by L. S. Hnilica, G. S. Stein and J. L. Stein. Florida, CRC Press Inc. (1989), pp. 73–163.
7. Wolf D. P., Sokoloski J. E., (1982) *J. Androl.*, 3:445–451.
8. Johnson, L. (1990), Spermatogenesis (Animal Species and Humans). In Gamete Physiology. Edited by R. H. Asch, J. P. Balmaceda and I. Johnston. Norwell, Massachusetts, Serono Symposia, USA, 1990, pp. 3–18.
9. Laskey, R. A., Fairman, M. P., and Blow, J. J. (1989), Science, 246:609–614.
10. Lohka, M. J. (1989), J. of Cell Science, 92:131–135.
11. Fang, F., Newport, J. W. (1991), Cell, 66:731–742.
12. Longo, F. J. Fertilization: A Comparative Ultrastructural Review. Biol. Reprod., 9 (1973) 149–215.
13. Royere et al., Freezing and Thawing Alter Chromatin Stability of Ejaculated Human Spermatozoa; Fluorescence Acridine Orange Staining and Feulgen-DNA Cytophotometric Studies. Gamete Res. 21 (1988) 51–57.
14. Longo, F. J. and M. Kunkle. Transformations of Sperm Nuclei Upon Insemination. Curr. Top. Dev. Biol., 12 (1978) 149–184.
15. Gordon et al., Soc. for Developmental Biology, 43rd Annual Symposium-Molecular Developmental Biology, Columbia University, New York, N.Y., Jun. 18–20, 1984, Abstract 63.
16. Gordon et al., In Vitro Activation of Human Sperm Induced by Amphibian Egg Extract. Exp. Cell Resl, 157 (1985) 409–418.
17. Brown et al., In vitro activation of human sperm nuclei using *Xenopus laevis* egg extract, *J. Cell Biol.*, 99 (1984) 396a.
18. Brown et al., The In Vitro Activation of Human Sperm Nuclei Using *Xenopus laevis* Egg Extract is Inhibited by Alkaline Phosphatase. J. Cell Biol., 101 (1985) 263a.
19. Brown et al., Chromatin Decondensation and DNA Synthesis in Human Sperm Activated In Vitro by Using *Xenopus laevis* Egg extracts. J. Exp. Zool., 242 (1987) 215–231.
20. Aitken, R. J. Assessment of Sperm Function for IVE Human Reprod., 3 (1988) 89–95.
21. Sher G. et al., In vitro sperm capacitation and transcervical intrauterine insemination for the treatment of refractory infertility. Fertil. Steril., 41 (1984) 260–264.
22. Asch et al., Pregnancy After Translaparoscopic Gametes Intrafallopian Transfer. Lancet 2 (1984) 1034–35.
23. Asch et al., Gamete Intra-Fallopian Transfer (GIFT): A New Treatment for Infertility. Int. J. Fertil., 30 (1985) 41–45.
24. Steptoe, P. C. and R. G. Edwards. Birth After the Reimplantation of a Human Embryo. Lancet 2 (1978) 366.
25. Trounson et al., The Investigation of Idiopathic Infertility By In Vitro Fertilization. Fertil. Steril., 34 (1980) 431–438.
26. U.S. DHHS publication No. (PHS)91–50213, Healthy People 2000: National Health Promotion and Disease Prevention Objectives.
27. Keel, B. A. The Semen Analysis. In: CRC Handbook for the Laboratory Diagnosis and Treatment of Infertility. B.

A. Keel and B. W. Webster, eds., CRC Press, Boca Raton, Ann Arbor and Boston, (1990) 29–66.
28. Liu, D. Y. and H. W. G. Baker. Tests of human sperm function and fertilization in vitro. Fertil. Steril., 58 (1992) 465–483.
29. Baker et al., Preparation and analysis of semen for IVF/GIFT. A. Trounson and D. K. Gardner, eds., CRC Press, Boca Raton, Ann Arbor and Boston, (1993) 33–57.
30. Liu et al., Spermatozoal nuclear chromatin decondensation in vitro a test for sperm immaturity. Comparison with results of human in vitro fertilization. Clin. Reprod. Fertil., 5 (1987) 191–201.
31. Kirschner et al., The timing of early developmental events in Xenopus. Trends in Genetics, Feb. (1985) 41.
32. Moghissi, K. S. and E. E. Wallach. Unexplained Infertility. Fertil. Steril., 39 (1983) 5–21.
33. Burslem, R. W. and J. C. Osborn. Unexplained Infertility. Br. Med. J., 292 (1986) 576–577.
34. Navot et al., The value of in vitro fertilization for the treatment of unexplained infertility. Fertil. Steril. 49 (1988) 854–857.
35. Blasco, L. Clinical Approach to the Evaluation of Sperm-Cervical Mucus Interactions. Fertil. Steril., 28 (1977) 1133–1145.
36. Rosenfeld et al., Diagnosis of Luteal Phase Inadequacy. Obstet. Gynecol., 56 (1980) 193–196.
37. Cary, W. H. Note On Determination of Patency of Fallopian Tubes By the Use of Collargol and X-Ray Shadow. Am. J. Obstet. Dis. Women Child, 69 (1914) 462–464.
38. Peterson, E. P. and Sh. J. Behrman. Laparoscopy of the Infertile Patient. Obstet. Gynecol., 36 (1970) 363–367.
39. Rogers et al., Analysis of Human Spermatozoal Fertilizing Ability Using Zona-Free Ova. Fertil. Steril., 32 (1979) 664–670.
40. Barros et al., Human Sperm Penetration into Zona-Free Hamster Oocytes as a test to Evaluate the Sperm Fertilizing Ability. Andrologia II (1979) 197–210.
41. Overstreet et al., Penetration of Human Spermatozoa into the Human Zona Pellucida and the Zona-Free Hamster Egg: A study of Fertile Donors and Infertile Patients. Fertil. Steril., 33 (1980) 534–542.
42. Dobson et al., Superovulation with intrauterine insemination in the treatment if infertility; a possible alternative to gamete intrafallopian transfer and in vitro fertilization. Fertil. Sterile, 48 (1987) 441–445.
43. Fleiss, J. L., Statistical Methods for Rates and Proportions, 2nd. Ed.N.Y.: John Wiley & Sons, Inc., 1981, pp. 13–15.
44. Wolgemuth, D. J., In: Mechanism and Control of Animal Fertilization. J. F. Hartmann, ed. Academic Press, Inc., New York, (1983) pp. 415–452.
45. Zirkin et al., In Vitro and In Vivo Studies of mammalian Sperm Nuclear Decondensation. Gamete Res., 11 (1985) 349–365.
46. Benbow, R. B. and C. C. Ford. Cytoplasmic Control of Nuclear DNA Synthesis During Early Development of Xenopus laevis: A Cell-Free Assay. Proc. Natl. Acad. Sci. USA, 72 (1975).
47. Zierler et al., Stockpiling of DNA Polymerases during Oogenesis and Embryogenesis in the Frog, Xenopus laevis. J. Biol. Chem., 260 (1975) 974–981.
48. Miake-Lye, R. And M. Kirschner. Induction of Early Mitotic Events in a Cell-Free System. Cell, 41 (1985) 165–175.
49. Newport, J. Nuclear Reconstitution In Vitro: Stages of Assembly around Protein-Free DNA. Cell, 48 (1987) 205.
50. Dilworth et al., Two Complexes That Contain Histones Are Required for Nucleosome Assembly In Vitro: Role of Nucleoplasmin and N1 in Xenopus Egg Extracts. Cell. 51 (1987) 1009–1018.
51. Steeno et al., Prevention of fertility disorders by detection and treatment of varicocele at school and college age. Andrologia 8 (1976) 47.
52. Gard, D. L. and M. W. Kirschner. Microtubule Assembly in Cytoplasmic Extracts of Xenopus Oocytes and Eggs. J. Cell Biol., 105 (1987) 2191–2201.
53. Gard, D. L. and M. W. Kirschner. A Microtubule-associated Protein from Xenopus Eggs That Specifically Promotes Assembly at the Plus-End. J. Cell Bio., 105 (1987) 2203.
54. Newport, J. and T. Spann. Disassembly of the Nucleus in Mitotic Extracts: Membrane Vesicularization, Lamin Disassembly, and Chromosome Condensation Are Independent Processes. Cell, 48 (1987) 219–230.
55. Blow, J. J. and R. A. Laskey. Initiation of DNA Replication in Nuclei and Purified DNA by a Cell-Free Extract of Xenopus Eggs. Cell, 47 (1986) 577–587.
56. Blow, J. J. and J. V. Watson. Nuclei act as independent and integrated units of replication in a Xenopus cell-free DNA replication system. EMBO, 6 (1987) 1997–2002.
57. Sheehan et al., Steps in the Assembly of Replication-Competent Nuclei in a Cell-Free System from Xenopus Eggs. J. Cell Biol., 106 (1988) 1–12.
58. Kirschner et al., The Timing of Early Developmental Events in Xenopus. TIG, Feb. (1985) 41–47.
59. Laskey et al., In: Genetic Engineering, Principles and Methods, Vol. 7, J. K. Setlow and A. Hollaender, editors, (1985) 135.
60. Kaiserman et al., Regulation of Xenopus laevis DNA Topolsomerase I Activity by Phosphorylation in Vitro . Biochemistry, 27 (1988) 3216–3222.
61. Lohka et al., Purification of Maturation-Promoting Factor, an Intracellular Regulator of Early Mitotic Events. Proc. Natl. Acad. Sci. USA, 85 (1988) 3009–3013.
62. Dunphy et al., The Xenopus cdc2 Protein is a Component of MPF, a Cytoplasmic Regulator of Mitosis. Cell, 54 (1988) 423–431.
63. Damjanov, I. Pathology of Infertility. Mosby-Year Book, Inc., St. Louis, Mo. (1993).
64. Pryor, J. L. and S. S. Howards. Varicocele. Urol. Clin. North Am., 14 (1987) 499.
65. Brown et al., Partial Purification of Human SpermChromatin Decondensation Protein(s) Isolated from *Xenopus laevis* Egg Extract. J. Cell Biol., 105 (1987) 169a.
66. Takihara et al., The pathophysiology of varicocele in male infertility. Fert. Steril. 55 (1991) 861–868.
67. Perreault et al., The role of disulfide bond reduction during mammalian sperm nuclear decondensation in vivo. Dev. Biol., 101 (1984) 160–167.
68. Coelingh, J. P. and R. H. Rozijn, In: The Biology of the Male Gamete. J. G. Duckett and P. A. Racey, eds., Academic Press, Inc., London, (1975) 245.
69. Comhaire, F. H. In Barrat CLR, Cooke, I. D. (Eds). Advances in Clinical Andrology. Lancaster, UK, MTP Press, Kluwer Academic, 1988.
70. Dubin, L. and R. D. Amelar. Etiologic factors in 1294 consecutive cases of male infertility. Fertil. Steril., 22 (1971) 469–740.
71. Rogers et al., Monitoring of suspected infertile men with varicocele by the sperm penetration assay. Fertil. Steril. 44 (1985) 800–805.
72. Rogers, B. J. The sperm penetration assay: its usefulness reevaluated. Fertil. Steril., 43 (1985) 821–840.

73. Johnson et al., Flow Cytometry of X and Y Chromosome-Bearing Sperm for DNA Using an Improved Preparation Method and Staining With Hoechst 33342., Gamete Res., 17 (1987) 203–212.
74. Mygatt et al., In vitro fertilization rates after varicocele repair. J. Ruol, 127 (1982) 1103.
75. Marks et al., Predictive parameters of successful varicocele repair. J. Urol, 136 (1986) 609–612.
76. Marmar et al., Insemination data on men with varicoceles. Fert. Steril., 57 (1991) 1084–1090.
77. Singer et al., Andrological Parameters in men with high sperm counts and possible correlation with age. Arch. of Androl. 24 (1990) 107–111.
78. Farkas, A. and M. Setchell. Fertility and Infertility. The Practitioner. 236 (1992) 633–639.
79. Tennekoon, K. H. and E. H. Karunanayake. Serum FSH, LH, and Testosterone Concentrations in Presumably Fertile Men: Effect of Age. Int. J. Fertil. 38 (1993) 108–112.
80. Slott, V. L. and S. D. Perreault. Computer-Assisted Sperm Analysis of Rodent Epididymal Sperm Motility Using the Hamilton-Thorn Motility Analyzer. Meth. Toxicol., 3A (1993) 319–333.
81. Kruger et al., Sperm morphologic features as a prognostic factor in in vitro fertilization. Fertil. Steril., 46 (1986) 1118–1123.
82. Kaiserman, H. B. and R. M. Benbow. Characterization of a Stable, Major DNA Polymerase Alpha Species Devoid of DNA Primase Activity. Nucl. Acid Res., 15 (1987) 10249–10265.
83. Yanagimachi et al., The use of Zona-Free Animal Ova as a Test-System for the Assessment of the Fertilizing Capacity of Human Spermatozoa. Biol. Reprod., 15 (1976) 471–476.
84. Kruger et al., A new computerized method of reading sperm morphology (strict criteria) is as efficient as technician reading. Fert. Steril., 59 (1993) 202–209.
85. Otto et al., Histochemistry 61 (1970) 249–254.
86. Webster et al., The Infertility Evaluation. In: CRC Handbook of the Laboratory Diagnosis and Treatment of Infertility. B. A. Keel and B. W. Webster, eds., CRC Press, Boca Raton, Ann Arbor and Boston, (1990) 1–9.
87. Elmer-Dewitt, P. Making Babies. Time, Sept. 30 (1991) 56–63.
88. U.S. Congress, Office of Technology Assessment, Infertility: Medical and Social Choices. OTA-BA 358, U.S. Government Printing Office, Washington, D.C., May 1988.
89. Brown et al., Partial Purification of *Xenopus laevis* Egg Extract Factors That Induce Swelling in Permeabilizing Human Sperm. J. Exp. Zool., 258 (1991) 263–272.
90. Krishan, A. Rapid DNA Content Analysis by the Propidium Iodide-Hypotonic Citrate Method. Meth. Cell Biol, 33 (1990) 121–125.
91. Wilchek, M. and E. A. Bayer. Introduction to Avidin-Biotin Technology. Meth. Enzymol., 184 (1990) 5–13.
92. Mortimer, D. Objective Analysis of Sperm Motility and Kinematics. In: CRC Handbook of the Laboratory Diagnosis and Treatment of Infertility. B. A. Keel and B. W. Webster, eds., CRC Press, Boca Raton, Ann Arbor and Boston, (1990) 99–131.
93. Gordon, J. W. Current Unresolved Controversies in Micromanipulation-Assisted Fertilization. J. Assist. Reprod. & Genet., 9 (1992) 184–189.
94. Coetzee et al., Usefulness of sperm penetration assay in fertility predictions. Arch. Androl., 23 (1989) 207–212.
95. Brandriff, B. F. and L. A. Gordon. Analysis of the First Cell Cycle in the Cross Between Hamster Eggs and Human Sperm. Gam. Res., 23 (1989) 299–308.
96. Trounson et al., Effect of delayed insemination on in vitro fertilization, culture and transfer of human embryos. J. Reprod. Fertil., 64 (1982) 285–294.
97. Liu et al., The use of in vitro fertilization to evaluate putative tests of human sperm function. Fertil. Steril. 49 (1988) 272–277.
98. Mallidis et al., Variation of semen quality in normal men. Int. J. Androl, 14 (1991) 99–107.
99. Otto, F. DAPI Staining of Fixed Cells for High-Resolution Flow Cytometry of Nuclear DNA. Meth. Cell Biol., 33 (1990) 105–110.
100. Yanagisawa et al., Cell Cycle Analysis Using Numerical Simulation of Bivariate DNA/Bromodeoxyuridine Distributions. Cytometry 6 (1985) 550–562.
101. Ikegami et al., Aphidicolin prevents mitotic cell division by interfering with the activity of DNA polymerase alpha. Nature 275 (1978) 458–460.
102. Brown, D. B. and M. Nagamani. Use of *Xenopus laevis* Frog Egg Extract in Diagnosing Human Male Unexplained Infertility. Yale J. Biol. Med. 65 (1992) 29–38.
103. Pines, J. Cell proliferation and control. Curr. Opin. in Cell Biol. 4 (1992) 144–148.
104. Rost, F. W. D., Quantitative Fluorescence Microscopy. Cambridge University Press, Cambridge, England (1991).
105. Vanderlaan et al., Improved High-Affinity Monoclonal Antibody to Iododeoxyuridine. Cytometry 7 (1986) 499–507.
106. Dolbeare et al., Using Monoclonal Antibodies in Bromodeoxyuridine-DNA Analysis. Meth. Cell Biol. 33 (1990) 207–216.
107. Lohka, M. J. and J. L. Mailer. Induction of Metaphase Chromosome Condensation in Human Sperm by Xenopus egg extracts. Experimental Cell Research, 179 (1988) 303–309.
108. Working, P. K. and G. J. Chellman. The Testis, Spermatogenesis, and the Excurrent Duct System. In: *Reproductive Toxicology and Fertility*. A. R. Scialli and M. J. Zinaman, Eds. McGraw-Hill, Inc., New York, 1993, 55–57.
109. Bartoov B., Eltes F., Weissenberg R., Lunenfeld B. Morphological characterization of abnormal human spermatozoa using transmission electron microcopy. Arch Androl 1980;5:305–22.
110. Bedford J. M., Bent M. J., Calvin H. I. Variations in the structural character and stability of the nuclear chromatin in morphologically normal human spermatozoan. J Reprod Fertil 1973;33: 19–29.
111. Evenson D. P., Darzynkiewiccz Z., Melamed M. R. Relation of mammalian sperm chromatin heterogeneity to fertility. Science 1980;210:1131–3.
112. Wolgemuth D. J. Synthetic activities of the mammalian early embryo: molecular and genetic alterations following fertilization. In: Hartmann J. F., editor. Mechanism and control of animal fertilization. New York: Academic Press, 1983:415–52.
113. Philpott A., Leno G. H., Laskey R. A. Sperm decondensation in Xenopus egg cytoplasm is mediated by nucleoplasmin. Cell 1991;65:569–78.
114. Brown D. B., Nagamani M. Use of *Xenopus laevis* frog egg extract in diagnosing human male unexplained infertility. Yale J Biol Med 1992; 65:29–38.
115. Yanagimachi R., Yanagimachi H., Rogers B. J. The use of zona-free animal ova as a test system for the assessment of the fertilizing capacity of human spermatozoa. Biol Reprod 1976;15:471–6.
116. Balhorn R., Reed S., Tanphaichitr N. Aberrant protamine 1/protamine 2 ratios in sperm of infertile human males. Experientia 1988;44:52–5.

117. Belokopytovak I. A., Kostyleva E. I., Tomilin A. N., Vorob'ev VI. Human male infertility may be due to a decrease of the protamine P2 content in sperm chromatin. Mol Reprod Devel 1993;34:53–7.
118. Peluso J. J., Luciano A. A., Nulsen J. C. The relationship between alterations in spermatozoal deoxyribonucleic acid, heparin binding sites, and semen quality. Fertil Steril 1992; 57:665–70.
119. Lipitz S., Bartoov B., Rajuan C., Reichart M., Kedem P., Mashiach S., Dor J. Sperm head ultramorphology and chromatin stability of males with unexplained infertility who fail to fertilize normal human ova in vitro. Andrologia 1992; 24:261–9.
120. Palermo G., Joris H., Devroey P., Van Steirteghem AC. Pregnancies after intracytoplasmic injection of single spermatozoon into an oocyte. Lancet 1992; 340:17–18.
121. Carlsen E., Giwercman A., Keiding N., Skakkebaek, N. Evidence for decreasing quality of semen during the past 50 years. Br Med J. 1989;305:609–613.
122. Perreault SD. Importance of sperm chromatin packaging and unpackaging for reproductive success. In: Whitcomb R. W., Zirkin B. R., eds. Understanding male infertility: basic and clinical approaches. Serono Symposia Publications Vol. 98. New York: Raven Press; 1993:267–280.
123. Rogers B. J. Examination of data from programs of in vitro fertilization in relation to sperm integrity and reproductive success. In: Burger E. J., Tardiff R. G., Scialli A. R., Zenick H., eds. Progress in clinical and biomedical research, vol. 302, sperm measures and reproductive success. Institute for health policy analysis forum on science, health, and environmental risk assessment. New York: Alan R. Liss, Inc.; 69–93.
124. Oliva R., Dixon G. H. Vertebrate protamine genes and the histone-to-protamine replacement reaction. Prog Nuc Acid Res Mol Biol. 1991;40:25–94.
125. Linder R., Hess R. Testicular toxicity and infertility in male rats treated with 1,3-dinitrobenzene. J. Toxicol Environ Health. 1986; 19:477–489.
126. Trasler J. M., Hales B. F, Robaire B. Paternal cyclophosphamide treatment of rats causes fetal loss and malformations without affecting male fertility. Nature. 1985; 316:144–146.
127. Hales B. F., Smith S., Robaire B. Cyclophosphamide in the seminal fluid of treated males: transmission to females by mating and effect on pregnancy outcome. Toxicol Appl Pharmacol. 1986; 84:423–430.
128. Hales B. F., Robaire B. Reversibility of the effects of chronic paternal exposure to cyclophosphamide on pregnancy outcome in rats. Mutat Res. 1990: 229:129–134.
129. Qiu J., Hales B. F., Robaire B. Adverse effects of cyclophosphamide on progeny can be mediated through post-testicular mechanisms in the rat. Biol Reprod. 1992; 46:926–931.
130. Hales B. F., Robaire B. Paternally mediated effects on progeny outcome. In: Whitcomb R. W., Zirkin B. R. eds. Understanding male infertility: basic and clinical approaches. Serono Symposia Publications Vol. 98. New York: Raven Press.
131. Royere, et al. (1981) Gamete Research, 21:51–57.
132. Atiee et al. (1995), Fertility and Sterility 61(3):652–655
133. Palermo et al. (1992), The Lancet, 340:17–18.
134. Palermo et al. (1995), Fertility and Sterility, 63(6):1231–1240.

What is claimed is:

1. An in vitro method for screening for abnormal human sperm as part of a regimen for assessing human sperm fertilizing capacity comprising:

obtaining a human sperm sample and isolating a number of sperm therefrom to provide a test sample;

incubating the test sample in a non-mammalian egg extract capable of supporting human sperm decondensation, DNA synthesis or sperm recondensation;

monitoring the test sample for sperm decondensation; and comparing test sperm decondensation of the sample to sperm decondensation of a sperm sample from a proven fertile male in the non-mammalian egg extract, wherein a test sample demonstrating less than 80% decondensed sperm relative to the control sample identifies abnormal human sperm.

2. A method for diagnosing infertility in a human male of unexplained infertility comprising:

isolating a number of sperm from the human male of unexplained infertility to provide a test sample;

incubating the test sample in a non-mammalian egg extract capable of supporting human sperm decondensation, DNA synthesis and chromatin recondensation; and comparing the amount of chromatin decondensation of the test sample to the amount of chromatin decondensation of a control sample from a human male of known fertility, wherein a sperm test sample demonstrating less than 80% decondensed sperm nuclei as compared to the sperm control sample is diagnostic of infertility in the human male of unexplained infertility.

3. The method of claim 1 or 2 wherein the non-mammalian egg extract is an amphibian egg extract, and the steps of incubating the test sample in the egg extract comprises the steps of:

permeabilizing a number of the sperm in the test sample in a lysolecithin-containing medium to provide a permeabilized test sperm;

chemically reducing a number of the permeabilized test sperm in an amount of the egg extract containing dithiothreitol to provide reduced sperm nuclei;

incubating an amount of the reduced sperm nuclei in a volume of the egg extract which includes a detectable labeling compound for about 15 minutes; and comparing the decondensation of the test sperm as a percentage to a percentage of condensed nuclei from sperm of a human male of proven fertility incubated in the egg extract for about 15 minutes.

4. The method of claim 1 or 2 wherein the non-mammalian egg extract is *Xenopus laevis* frog egg extract.

5. The method of claim 1 or 2 wherein the number of sperm in the test sample is about 200,000.

6. The method of claim 1 or 2 wherein sperm decondensation is monitored for about 10 minutes.

7. The method of claim 1 or 2 wherein the sperm test sample is permeabilized in a medium containing about 0.05% lysolecithin and about 1 $\mu$g/ml soybean trypsin inhibitor for about 5 minutes at about 22° C.

8. A method for screening human sperm as part of a regimen for selecting prospective fertile human sperm donors for in vitro fertilization of a human egg comprising:

incubating a test sperm sample from a prospective human sperm donor in a non-mammalian egg extract containing a detectable labeling compound;

monitoring sperm decondensation of the test sample; and selecting a test sperm sample that demonstrates an amount of sperm chromatin decondensation of at least about 80% of control sperm chromatin decondensation from a human male of proven fertility as prospective donor sperm for in vitro fertilization of a human egg.

9. The method of claim 8 wherein the non-mammalian egg extract is a frog egg extract.

10. The method of claim 8 wherein sperm chromatin decondensation is monitored for at least about 15 minutes.

11. The method of clam 9 wherein the frog egg extract is a *Xenopus laevis* or *Rana pipiens* frog egg extract.

12. The method of claim 11 wherein the frog egg extract is *Xenopus laevis* frog egg extract and the incubation of the test sperm sample in frog egg extract comprises the steps of:
   permeabilizing a number of test sample sperm in a medium containing lysolecithin and a protease inhibitor to provide permeabilized human test sperm;
   reducing a number of the permeabilized test sperm in a XEIM containing about 50 mM dithiothreitol for about 45 minutes at about 0° C. to about 4° C.; and
   incubating the reduced sperm in the frog egg extract for a period of time sufficient to allow chromatin decondensation to occur.

13. The method of claim 8 wherein the detectable labeling compound is $^3$H-TTP or tritiated thymidine.

14. A screen for detecting human sperm damage from a cross-linking chemical agent comprising:
   obtaining a sample of human sperm from a patient suspected of having been exposed to a cross-linking chemical agent to provide a test sperm sample;
   preparing the test sperm sample for analysis of sperm decondensation in a non-mammalian egg extract; and
   determining the percent of decondensed nuclei in the test sample present at a time point where at least 80% of sperm nuclei in a control fertile human sperm sample have decondensed in the non-mammalian egg extract, wherein a percentage of test sperm decondensation less than 80% of the percentage of a fertile human sperm sample decondensation identifies human sperm damage from a cross-linking chemical agent in the test sample.

15. The method of claim 14 wherein the non-mammalian egg extract is a *Xenopus laevis* frog egg extract.

16. The method of claim 14 wherein a percentage of test sperm decondensation less than 80% of fertile human sperm decondensation identifies sperm damage in the test sample.

17. The method of claim 14 wherein the cross-linking chemical agent is a sulfur cross-linking agent.

18. A method for screening human sperm for use in intracytoplasmic sperm injection fertilization comprising:
   obtaining a human sperm sample containing at least about 400,000 sperm to provide a test sperm sample;
   permeabilizing said test sperm sample;
   adding about 100,00 permeabilized sperm to a non-mammalian egg extract containing a detectable labeling compound;
   monitoring sperm activation events of DNA synthesis and chromatin decondensation of the test sperm sample; and
   selecting for intracytoplasmic sperm injection a test sperm sample demonstrating at least 80% DNA synthesis and chromatin decondensation relative to a control sperm sample from a proven fertile male.

19. A method for assessing human sperm activation events from a sperm sample having a low sperm count comprising:
   obtaining a human sperm sample containing at least about 400,000 sperm to provide a test sperm sample;
   monitoring chromatin decondensation in the test sperm sample; and
   comparing the test sperm sample chromatin decondensation to chromatin decondensation of a human sperm sample from a human male of proven fertility;
   wherein a test sperm sample chromatin decondensation of less than 80% as compared to chromatin decondensation of the human sperm sample from a human male of proved fertility provides a method for assessing human sperm activation events of a sperm sample having a low sperm count.

20. A method for screening human sperm for use in intracytoplasmic sperm injection fertilization comprising:
   obtaining a human sperm sample to provide a test sample;
   incubating the test sperm sample in a non-mammalian egg extract containing a detectable labeling compound;
   monitoring sperm chromatin decondensation in the sample test sample;
   comparing the test sperm chromatin decondensation to sperm chromatin decondensation of a control sperm sample from a proven fertile male; and
   selecting for intracytoplasmic sperm injection a sperm sample from a human male having a test sperm sample demonstrating about 80% or greater chromatin decondensation relative to the control sperm chromatin decondensation.

21. A frozen *Xenopus laevis* frog egg extract, said extract prepared by a process of:
   collecting mature *Xenopus laevis* frog eggs,
   treating the collected eggs to provide dejellied eggs,
   lysing the dejellied eggs,
   collecting the middle layer of the lysed dejellied eggs to provide an extract,
   selecting the extract which support the human sperm activation events of DNA synthesis, chromatin decondensation or chromatin recondensation,
   adding the selected extract dropwise to a volume of liquid nitrogen to provide a frozen *Xenopus laevis* frog egg extract.

22. The frozen *Xenopus laevis* frog egg extract of claim 21 wherein the detectable labeling compound is bromodeoxyuridine.

23. The frozen *Xenopus laevis* frog egg extract of claim 21 wherein bromodeoxyuridine is added to the dejellied eggs.

24. An in vitro human sperm infertility screening method comprising:
   isolating a number of sperm from the human male to provide a test sample;
   incubating the test sample in a non-mammalian egg extract capable of supporting DNA synthesis;
   labeling newly synthesized DNA with a halogenated nucleoside to provide labeled newly synthesized DNA;
   exposing the labeled newly synthesized DNA to a first monoclonal antibody specific for the halogenated nucleoside;
   staining the labeled newly synthesized DNA with a detectable secondary antibody specific for the first antibody to provide detectably labeled newly synthesized DNA; and
   quantitating the detectably labeled newly synthesized DNA of the test sample to provide a test sample DNA synthesis amount; and
   comparing the amount of test sample DNA synthesis to an amount of DNA synthesis of a control sperm sample of a fertile male to provide an in vitro human male infertility screening method.

25. The method of claim 24 wherein the halogenated nucleoside is bromodeoxyuridine.

26. The method of claim 25 wherein the first antibody is anti-Brd Urd monoclonal mouse IgG and the second antibody is an anti-mouse antibody that is conjugated to a detectable base.

27. A diagnostic kit for screening human males for infertility comprising:

a carrier means adapted to receive container means therein, a first container means containing a volume of dithiothreitol, a second carrier means containing a volume of lysolecithin, a third container means containing a non-mammalian egg extract capable of supporting fertile human sperm chromatin decondensation, and a container means suitable for including therein a human sperm sample.

28. The kit of claim 27 wherein the non-mammalian egg extract In a *Xenopus laevis* egg extract.

29. The kit of claim 27 comprising a container means containing a volume of bovine serum albumin.

30. The kit of claim 28 wherein in the *Xenopus laevis* egg extract is a frozen egg extract, said extract prepared by a process comprising the steps of:

collecting mature *Xenopus laevis* frog eggs, treating the collected eggs to provide dejellied eggs, lysing the dejellied eggs, collecting the middle layer of the lysed dejellied eggs to provide an extract, selecting the extract which support the human sperm activation events of DNA synthesis, chromatin decondensation or chromatin recondensation, adding the selected extract dropwise to a volume of liquid nitrogen to provide a frozen *Xenopus laevis* frog egg extract.

31. The kit of claim 30 wherein the extract is filtered prior to the selecting step.

32. The frozen *Xenopus laevis* frog egg extract of claim 21 wherein the extract is filtered prior to the selecting step.

\* \* \* \* \*